United States Patent
Laal et al.

(10) Patent No.: US 9,335,325 B2
(45) Date of Patent: May 10, 2016

(54) **IMMUNODOMINANT *MYCOBACTERIUM TUBERCULOSIS* PEPTIDES FROM CELL WALL PROTEINS FOR EARLY DIAGNOSIS AND IMMUNIZATION**

(75) Inventors: Suman Laal, Cortlandt Manor, NY (US); Susan Zolla-Pazner, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 1090 days.

(21) Appl. No.: 12/988,595

(22) PCT Filed: Apr. 20, 2009

(86) PCT No.: PCT/US2009/041077
§ 371 (c)(1),
(2), (4) Date: Jan. 10, 2011

(87) PCT Pub. No.: WO2009/129521
PCT Pub. Date: Oct. 22, 2009

(65) Prior Publication Data
US 2011/0104194 A1 May 5, 2011

Related U.S. Application Data

(60) Provisional application No. 61/046,405, filed on Apr. 19, 2008.

(51) Int. Cl.
*A61K 39/04* (2006.01)
*A61K 39/00* (2006.01)
*A61K 39/02* (2006.01)
*G01N 33/569* (2006.01)
*C07K 14/35* (2006.01)

(52) U.S. Cl.
CPC ............ *G01N 33/5695* (2013.01); *C07K 14/35* (2013.01); *G01N 2333/35* (2013.01); *G01N 2469/20* (2013.01)

(58) Field of Classification Search
USPC .................. 424/9.1, 9.2, 184.1, 185.1, 234.1, 424/248.1, 130.1, 139.1, 164.1; 435/4, 7.1, 435/7.2
See application file for complete search history.

(56) References Cited

U.S. PATENT DOCUMENTS

2005/0084904 A1    4/2005   Laal et al.

FOREIGN PATENT DOCUMENTS

| WO | 03/012395 A2 | 2/2003 | |
|---|---|---|---|
| WO | WO03073101 | * 4/2003 | ............ G01N 33/554 |

OTHER PUBLICATIONS

Singh, K.K. et al., Antigens of *Mycobacterium tuberculosis* Expressed during Preclinical Tuberculosis: Serological Immunodominance of Proteins with Repetitive Amino Acid Sequences, Infection & Immunity. 69:4185-4191 (2001).

* cited by examiner

*Primary Examiner* — Rodney P Swartz
(74) *Attorney, Agent, or Firm* — Browdy and Neiamrk, PLLC

(57) ABSTRACT

A number of peptide epitopes and fragments from three *Mycobacterium tuberculosis* (Mtb) cell wall proteins have been identified as early antigens that induce antibodies early during Mtb infection in humans. The proteins are Proline-Threonine Repetitive Protein (PTRP), PE-PGRS51, and LipC. These peptides, alone or in mixtures, or as parts of fusion polypeptides or peptide multimers, are useful as antigens for serological detection of early in infection by detecting the presence of early antibodies against these proteins, thereby permitting earlier diagnosis of Mtb infection than was heretofore possible by conventional means. The above peptides and other peptide-based compositions are also used as immunogens for inclusion in TB vaccines. Also provided are methods for early diagnosis of Mtb infection and for immunizing a subject to prevent or treat Mtb infections and tuberculosis.

28 Claims, 15 Drawing Sheets

Fig.1
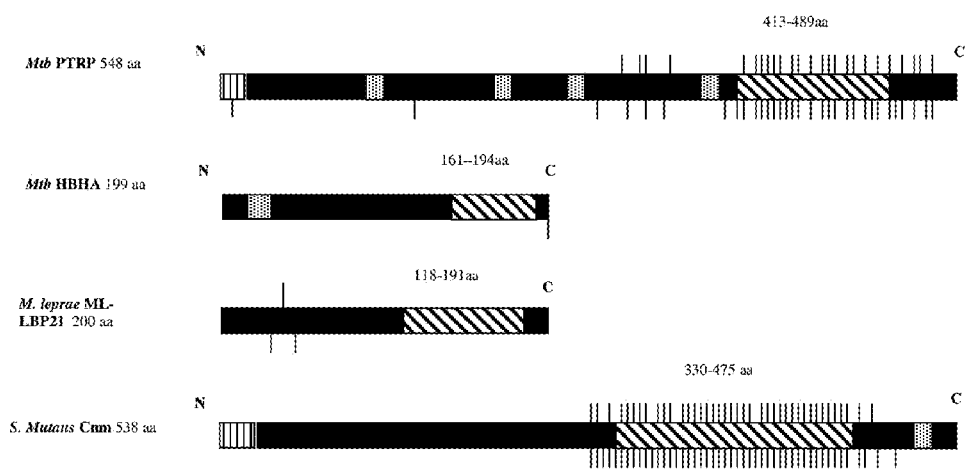
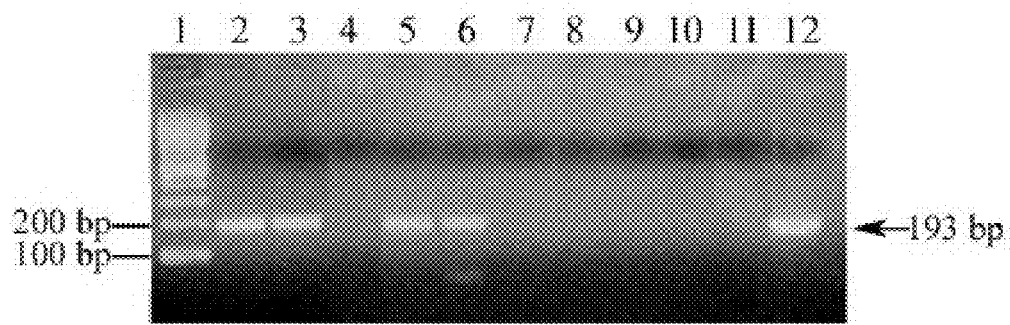
Fig. 2

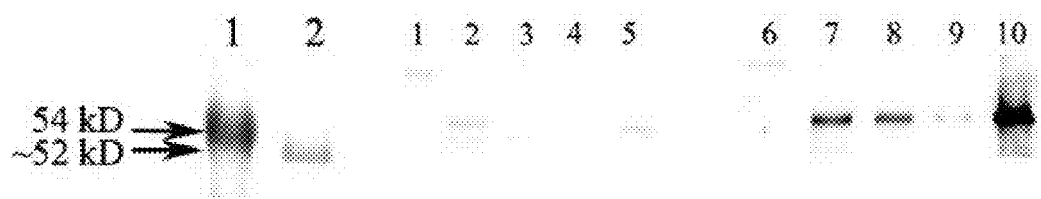
Fig. 4A            Fig. 4B
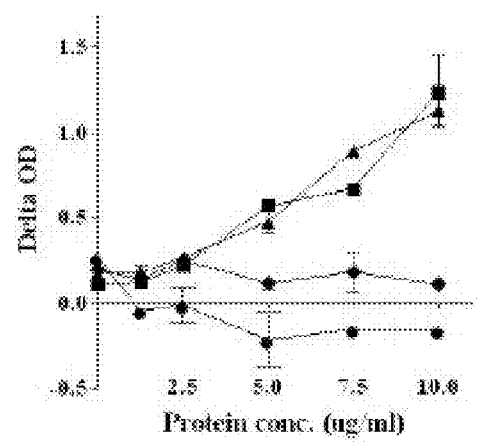 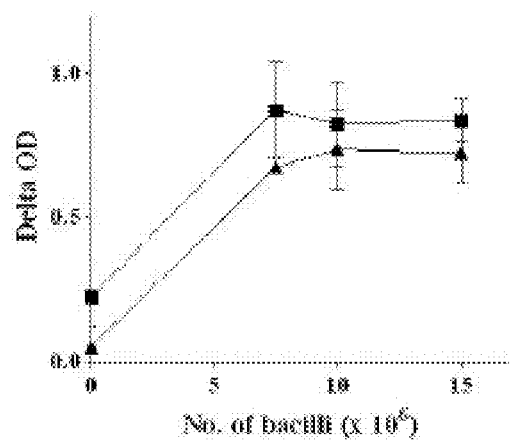
Fig. 4C            Fig. 4D

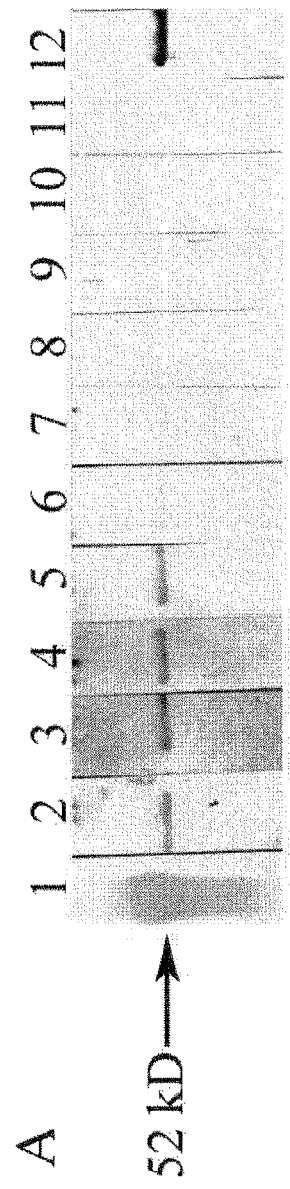

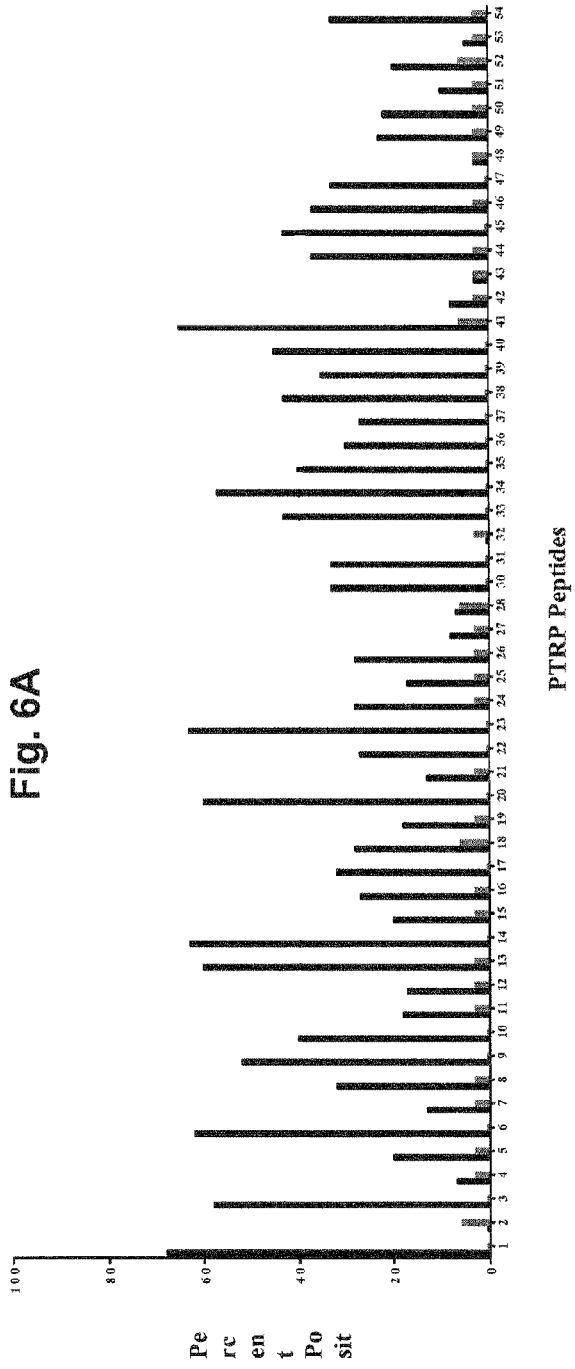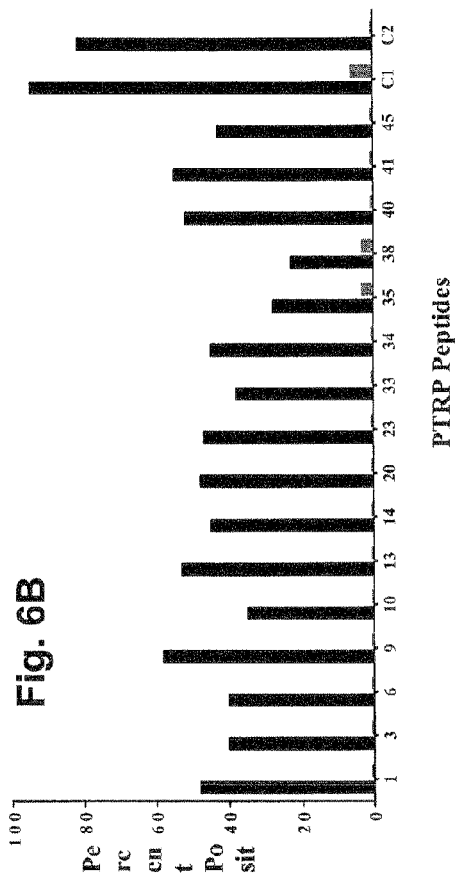
Fig. 6A
Fig. 6B

FIG. 9

PTRP Nucleic Acid and Protein

Nucleotide sequence is SEQ ID NO:1          Amino acid sequence is SEQ ID NO:2

```
   1 atggacgtcgctttggggggttgcggtcacggatcgggtcgcgcgtctggcgctggtcgac
     M   D   V   A   L   G   V   A   V   T   D   R   V   A   R   L   A   L   V   D      20
  61 tcggctgcgcccggcgcaccgtgatcgaccagttcgtgctcgatgtggcggagcacccggtc
     S   A   A   P   G   T   V   I   D   Q   F   V   L   D   V   A   E   H   P   V      40
 121 gaggtgttaaccgagaccgtggtgggcacggatcggtcattggccggcgaaaaccaccgg
     E   V   L   T   E   T   V   V   G   T   D   R   S   L   A   G   E   N   H   R      60
 181 ctggtcgctacccggctgtgttggccggatcaggccaaagctgacgagctgcagcacgca
     L   V   A   T   R   L   C   W   P   D   Q   A   K   A   D   E   L   Q   H   A      80
 241 ctgcaggactccggggtccacgacgttgccgtgatatccgaggcgcaggccgccacggcg
     L   Q   D   S   G   V   H   D   V   A   V   I   S   E   A   Q   A   A   T   A     100
 301 ctggtcggggcggcacatgccggctctgccgtgctgttggtgggtgatgagacggcaacc
     L   V   G   A   A   H   A   G   S   A   V   L   L   V   G   D   E   T   A   T     120
 361 ttatcggtggttggtgacccggacgcgccgccgacgatggtggccgtcgcgccggtggcg
     L   S   V   V   G   D   P   D   A   P   P   T   M   V   A   V   A   P   V   A     140
 421 ggcgccgacgccacatcgaccgtcgatacccctgatggcccggctcggcgaccaggccctc
     G   A   D   A   T   S   T   V   D   T   L   M   A   R   L   G   D   Q   A   L     160
 481 gccccggggggatgtcttcctggtgggtaggtccgccgagcacaccacggttcttgccgac
     A   P   G   D   V   F   L   V   G   R   S   A   E   H   T   T   V   L   A   D     180
 541 cagctgcgcgcggcgtcgacgatgcgcgtgcagactcccgacgaccccacgttcgcgctg
     Q   L   R   A   A   S   T   M   R   V   Q   T   P   D   D   P   T   F   A   L     200
 601 gcccgtggcgcggcgatggcggccggcgccgctacgatggcgcacccggccctggtcgcg
     A   R   G   A   A   M   A   A   G   A   A   T   M   A   H   P   A   L   V   A     220
 661 gatcgaccacttcgctcccccgggccgaggcggggcaatcgggttctgaaggcgagcag
     D   A   T   T   S   L   P   R   A   E   A   G   Q   S   G   S   E   G   E   Q     240
 721 ctggcgtactcgcaggccagcgattacgagctgcttccggtcgacgaatatgaggaacac
     L   A   Y   S   Q   A   S   D   Y   E   L   L   P   V   D   E   Y   E   E   H     260
 781 gacgaatacggggcagccgcggatcgctcggcgccgttgagccgacggtcgctgctgatc
     D   E   Y   G   A   A   A   D   R   S   A   P   L   S   R   R   S   L   L   I     280
 841 ggcaacgctgtcgtggccttttgcgtgatcggtttcgcctcgctggcggtggcggtggcg
     G   N   A   V   V   A   F   A   V   I   G   F   A   S   L   A   V   A   V   A     300
 901 gtcaccatccgaccgaccgcggcctcaaaaccggtagagggacaccaaaacgcccagcca
     V   T   I   R   P   T   A   A   S   K   P   V   E   G   H   Q   N   A   Q   P     320
 961 gggaagttcatgccgttgttgccgacgcaacagcaggcgccggtcccgccg↓cctccgccc
     G   K   F   M   P   L   L   P   T   Q   Q   Q   A   P   V   P   P       P   P     340
1021 gatgatcccaccgctggattccagggcggcaccattccggctgtacagaacgtggtgccg
     D   D   P   T   A   G   F   Q   G   G   T   I   P   A   V   Q   N   V   V   P     360
1081 cggccgggtaccctcacccggggtgggtgggacgccggcttcgcctgcgccggaagcgccg
     R   P   G   T   S   P   G   V   G   G   T   P   A   S   P   A   P   E   A   P     380
1141 gccgtgccggtgttgtgcctgccccggtgccaatcccggtcccgatcatcattccccg
     A   V   P   G   V   V   P   A   P   V   P   I   P   V   P   I   I   I   P   P     400
1201 ttcccggggttggcagcctggaatgccgaccatccccaccgcaccgccgacgacgccggtg
     F   P   G   W   Q   P   G   M   P   T   I   P   T   A   |P   P   T   T|   |P   V|  420
1261 accacgtcggcgacgacgccgccgaccacgccgaccacgccggtgaccacgccgcca
     |T   T|   |S   A   T   T|   |P   P   T   T|   |P   P   T   T|   |P   V   T   T|   |P   P|   440
1321 acgacgccgccgaccacgccggtgaccacgccgccaacgacgccgccgaccacgccggtg
     |T   T|   |P   P   T   T|   |P   V   T   T|   |P   P   T   T|   |P   P   T   T|   |P   V|   460
1381 accacgccaccaacgaccgtcgccccgacgaccgtcgccccgacgacggtcgctccgacc
     |T   T|   |P   P   T   T|   |V   A   P   T|   |V   A   P   T|   480
1441 accgtcgccccgaccacggtcgctccagccaccgccacgccgacgaccgtcgctccgcag
     |T|   V   |A   P   T   T|   V   |A   P   A   T|   |T   P   T   T|   V   A   P   |Q|   500
1501 ccgacgcagcagcccacgcaacaaccaacccaacagatgccaacccagcagcagaccgtg
     |P   T   Q|   |Q   P   T   Q|   |Q   P   T   Q|   Q   |M   P   T   Q|   Q   Q   T   V     520
1561 gccccgcagacggtggcgccggctccgcagccgccgtccggtggccgcaacggcagcggc
     A   P   Q   T   V   A   P   A   P   Q   P   P   S   G   G   R   N   G   S   G     540
1621 gggggcgacttattcggcgggttctga
     G   G   D   L   F   G   G   F   *                                                 548
```

FIG. 10
PE PGRS51 Nucleic Acd and Protein

Nucleotide sequence is SEQ ID NO:3  Amino acid sequence is SEQ ID NO:4

```
   1 atgtcgtttgtcgtagcagtcccggaggcattggcggcggccgcgtcggatgtggcgaac
     M  S  F  V  V  A  V  P  E  A  L  A  A  A  A  S  D  V  A  N    20
  61 atcggttctgcgctaagtgccgcgaatgcagcggcagccgccggcacaacggggctactg
     I  G  S  A  L  S  A  A  N  A  A  A  A  A  G  T  T  G  L  L    40
 121 gcagccggtgccgacgaggtctcggccgccctggcgtcgctgttttccgggcacgctgtg
     A  A  G  A  D  E  V  S  A  A  L  A  S  L  F  S  G  H  A  V    60
 181 agctaccaacaggtcgcggcccaggcgacggcgttacacgatcagtttgtccaggccttg
     S  Y  Q  Q  V  A  A  Q  A  T  A  L  H  D  Q  F  V  Q  A  L    80
 241 accggtgccggcggatcgtacgccctcaccgaggccgccaacgtccagcagaatctgctg
     T  G  A  G  G  S  Y  A  L  T  E  A  A  N  V  Q  Q  N  L  L   100
 301 aacgcaattaacgcgcccactcaggcgctgttggggcgcccgttaattggcgacggggct
     N  A  I  N  A  P  T  Q  A  L  L  G  R  P  L  I  G  D  G  A   120
 361 gtcggcaccgccagcagccccgacgggcaagatggcggtctgctgttcggcaacggggc
     V  G  T  A  S  S  P  D  G  Q  D  G  G  L  L  F  G  N  G  G   140
 421 gccggctacaacagcgccgccacgcccggaatggccggcggcaacggcggcaacgccgga
     A  G  Y  N  S  A  A  T  P  G  M  A  G  G  N  G  G  N  A  G   160
 481 ttgatcggcaacggcggtactggcgggtcgggcggtgccggcgcggccggtggcgccggc
     L  I  G  N  G  G  T  G  G  S  G  G  A  G  A  A  G  G  A  G   180
 541 ggcagcggcggctggttgtacggcaacggcggaaacggcggcatcggcgggaatgcgatc
     G  S  G  G  W  L  Y  G  N  G  G  N  G  G  I  G  G  N  A  I   200
 601 gtcgcggcggtgccggcggcaatggggcgctggcggcgccgccggattgtgggcagt
     V  A  G  G  A  G  G  N  G  G  A  G  G  A  A  G  L  W  G  S   220
 661 ggcggcagcggcggccaaggcggcaacggtctgaccggcaacgacggcgtgaatccgcc
     G  G  S  G  G  Q  G  G  N  G  L  T  G  N  D  G  V  N  P  A   240
 721 cccgtcacaaacccgcgctaaatggcgccggcgacagcaatatcgagccgcaaacc
     P  V  T  N  P  A  L  N  G  A  A  G  D  S  N  I  E  P  Q  T   260
 781 agcgtcctgatcggcacccaaggcggtgacggcacgcccggggggtgctggcgtcaacggc
     S  V  L  I  G  T  Q  G  G  D  G  T  P  G  G  A  G  V  N  G   280
 841 ggcaacggtggcgcggcggagacgccaatggcaaccccgcaaacacctcgatcgccaac
     G  N  G  G  A  G  G  D  A  N  G  P  A  N  T  S  I  A  N   300
 901 gcaggcgccggcgggaacggcgccgccggcggtgacggcggtgccaatggcggtgcgggc
     A  G  A  G  G  N  G  A  A  G  G  D  G  G  A  N  G  G  A  G   320
 961 ggcgccggcgggcaggccgcgtccgccggtagttccgtcggcggtgacggcggcaacggc
     G  A  G  G  Q  A  A  S  A  G  S  S  V  G  G  D  G  G  N  G   340
1021 ggtgccggcggtacgggcacgaacgggcacgccggcggcgggcggcgccggcggtgcc
     G  A  G  G  T  G  T  N  G  H  A  G  G  A  G  G  A  G  G  A   360
1081 ggtggtcgcggcgggtggctggtcggcaacggtggcaacggtggcaacggtgccgccggc
     G  G  P  G  G  W  L  V  G  N  G  G  N  G  G  N  G  A  A  G   380
1141 ggcaacggcgccatcggcggtaccggtggtgccggcggcgtccccgccaaccagggcggt
     G  N  G  A  I  G  G  T  G  G  A  G  G  V  P  A  N  Q  G  G   400
1201 aacagcgccctaggcacccagccggtcggcggcgacggcggcgacggcggcaacggggc
     N  S  A  L  G  T  Q  P  V  G  G  D  G  G  D  G  G  N  G  G   420
1261 accggaggcaccggcgggcgtggcggcgacggcggatccggcggcgcgggcggcgcgagc
     T  G  G  T  G  G  R  G  G  D  G  G  S  G  G  A  G  G  A  S   440
1321 ggttggttgatgggcaacggcggcaacggcggcaacggcggcaccggcggctcaggcggt
     G  W  L  M  G  N  G  G  N  G  G  N  G  G  T  G  G  S  G  G   460
1381 gtcggcggcaatggcggcatcggcggtgacggcgccggcggcggaaacgccacgagcacg
     V  G  G  N  G  G  I  G  G  D  G  A  G  G  N  A  T  S  T   480
1441 cgagcatccccttcgacgcccacggggggtaacggcggcgctggtggcgacgctggtcac
     S  S  I  P  F  D  A  H  G  G  N  G  G  D  A  G  H   500
1501 ggcggaacgggcggcgacggcggtgacgggggcatgccggcaccggtggacgtggcggg
     G  G  T  G  G  D  G  G  D  G  G  H  A  G  T  G  G  R  G  G   520
1561 ttactggccggccagcacgcgcaactccggcaatggcggtggcggcggtaccggcggtgcc
     L  L  A  G  Q  H  A  N  S  G  N  G  G  G  G  T  G  G  A   540
1621 gggggcacccatggcaccccggcagcggcaacgcaggcggcaccggcaccggtaacgct
     G  G  T  H  G  P  G  S  G  N  A  G  G  T  G  T  G  N  A   560
1681 gacagcacaaacggcgggccaggcagcgacggcctcggcggggacgcgtttaacggcagt
     D  S  T  N  G  P  G  S  D  G  L  G  G  D  A  F  N  G  S   580
1741 cgcggcaccgacggcaaccccggctaa
     R  G  T  D  G  N  P  G  *                                     588
```

FIG. 16

LipC Nucleic Acd and Protein

Nucleotide sequence is SEQ ID NO:5     Amino acid sequence is SEQ ID NO:6

```
        atgaaccagcgacgcgccgccgggtcaaccggtgtggcctacatcagatggttgctacgt    60
1       M  N  Q  R  R  A  A  G  S  T  G  V  A  Y  I  R  W  L  L  R
        gcccgtcccgctgactatatgctggccttgagtgtcgccggggggttcgctaccggtggtg   120
21      A  R  P  A  D  Y  M  L  A  L  S  V  A  G  G  S  L  P  V  V
        ggtaagcacctcaagccgctcggcggcgttactgccatcggcgtctgggcgcccggcac     180
41      G  K  H  L  K  P  L  G  G  V  T  A  I  G  V  W  G  A  R  H
        gcatccgatttcttgtccgcgacggcgaaggatttactgaccccggtatcaacgaggtt     240
61      A  S  D  F  L  S  A  T  A  K  D  L  L  T  P  G  I  N  E  V
        cgccgtcgagatcgtgccagcacgcaggaggtttccgtcgcggccttacgcggcatcgtt    300
81      R  R  R  D  R  A  S  T  Q  E  V  S  V  A  A  L  R  G  I  V
        tcgcccgacgaccttgccgtcgaatggccggcgccggagcgcacgccgccggtctgcggg   360
101     S  P  D  D  L  A  V  E  W  P  A  P  E  R  T  P  P  V  C  G
        gcgctgcgccaccgccgttacgtccaccgccgtcgcgtcctctacggcgacgacccggcc   420
121     A  L  R  H  R  R  Y  V  H  R  R  R  V  L  Y  G  D  D  P  A
        cagttgctcgacgtatggcgccgcaaagatatgcccaccaaacccgcgccggtgttgatc   480
141     Q  L  L  D  V  W  R  R  K  D  M  P  T  K  P  A  P  V  L  I
        ttcgtcccaggcggtgcctgggtgcacggcagtcgcgccatccaggggtatgcggtgctg   540
161     F  V  P  G  G  A  W  V  H  G  S  R  A  I  Q  G  Y  A  V  L
        tctcggctggccgcacaggggtgggtgtgcctatcgatcgactacgggtcgcaccgcat   600
181     S  R  L  A  A  Q  G  W  V  C  L  S  I  D  Y  R  V  A  P  H
        caccgctggccacgacacatcctggatgtcaagaccgccatcgcgtgggcacgggccaat   660
201     H  R  W  P  R  H  I  L  D  V  K  T  A  I  A  W  A  R  A  N
        gtcgacaaattcggcggtgaccgcaatttcattgcggtggctggttgttcggccggcggc   720
221     V  D  K  F  G  G  D  R  N  F  I  A  V  A  G  C  S  A  G  G
        cacttgtccgcgctggccgggctcaccgccaacgacccgcaatatcaggccgagctgcca   780
241     H  L  S  A  L  A  G  L  T  A  N  D  P  Q  Y  Q  A  E  L  P
        gagggctccgacacgtcggtcgacgcggtggtggggatttacggccgctacgactgggag   840
261     E  G  S  D  T  S  V  D  A  V  V  G  I  Y  G  R  Y  D  W  E
        gaccgctccaccccggaacgtgcccggttcgtcgattttctggagcgggtagtggttcag   900
281     D  R  S  T  P  E  R  A  R  F  V  D  F  L  E  R  V  V  V  Q
        cgcacgattgatcgtcaccccgaagtgttccgtgacgcgtcgccgatccaacgagtcacc   960
301     R  T  I  D  R  H  P  E  V  F  R  D  A  S  P  I  Q  R  V  T
        agaaatgcaccgccattcctggtgattcatggcagccgtgactgtgtcatcccggttgag  1020
321     R  N  A  P  P  F  L  V  I  H  G  S  R  D  C  V  I  P  V  E
        caggcgcggagctttgtcgagcggttacgagcggtctcccgctcacaggttggctacctg  1080
341     Q  A  R  S  F  V  E  R  L  R  A  V  S  R  S  Q  V  G  Y  L
        gagctgcccggtgcgggccacggcttcgacctgctagacggcgctcgcaccggcccgacg  1140
361     E  L  P  G  A  H  G  F  D  L  L  D  G  A  R  T  G  P  T
        gcacacgcgatcgcgctgtttctcaaccaggttcatcgcagccgggcacagttcgcgaaa  1200
381     A  H  A  I  A  L  F  L  N  Q  V  H  R  S  R  A  Q  F  A  K
        gaggtcatctaa                                                  1212
401     E  V  I  *
```

IMMUNODOMINANT *MYCOBACTERIUM TUBERCULOSIS* PEPTIDES FROM CELL WALL PROTEINS FOR EARLY DIAGNOSIS AND IMMUNIZATION

BACKGROUND OF THE INVENTION

1. Field of the Invention

The invention in the fields of microbiology and medicine relates to methods for rapid early detection of mycobacterial disease in humans, particularly tuberculosis (TB) based on the presence of antibodies to particular "early" mycobacterial antigens in the form of peptide epitopes which have not been previously recognized for this purpose. Assay for such antibodies using these early peptide epitopes permits diagnosis of TB earlier than has been heretofore possible. The invention is also directed to vaccine compositions and methods useful for preventing or treating TB by immunizing with such peptide-based antigens.

2. Description of the Background Art

Globally, TB kills ~3 million and infects ~9 million new individuals every year. The HIV-epidemic has exacerbated the TB epidemic in TB-endemic countries and has led to TB becoming the leading cause of morbidity and mortality in this highly vulnerable population. The development of new drugs, vaccines and diagnostic tests for TB is a major priority and towards this goal, the genomes of *Mycobacterium tuberculosis* (Mtb) H37Rv, and subsequently several clinical isolates of Mtb, and some non-tuberculous pathogenic and non-pathogenic mycobacteria have been, or are being currently sequenced (7, 13, 23, 52) (See also, the WWW URL ncbi.nlm.nih.gov/sutils/genom_table.cgi). The availability of these resources has accelerated the pace of research aimed at devising rational strategies for TB control.

It is well established that Mtb adapts to the changing environmental conditions during the course of progression of infection to clinical disease by differential gene expression (6, 38, 41, 48, 49, 53, 54). In the quest to understand the host-pathogen interactions that lead to establishment of Mtb infection, the present inventors and colleagues had used sera from Mtb aerosol-infected rabbits for immuno-screening a λgt11 expression library of Mtb genomic DNA (49) and published patent applications. These sera identified several Mtb proteins that contain tandem repeats of unique amino acid motifs in their sequence, and were either known or predicted to be surface/secreted proteins (49).

One of these repetitive proteins was a Proline-Threonine Repetitive Protein (PTRP; Rv0538) that is annotated as a hypothetical cell-membrane protein and classified to the functional category of cell-wall and cell processes in the Mtb H37Rv genome (7, 49). Although there is no sequence similarity, the domain organization of PTRP is reminiscent of the heparin-binding hemagglutinin (HBHA; Rv0475) of Mtb and the laminin-binding protein (ML-LBP21; ML1683) of *M. leprae*, in that all three proteins have repeats of specific amino-acid motifs clustered towards the C-terminus (29, 46, 49).

Another Mtb cell wall protein, PE-PGRS51 (Rv3367) has multiple tandem repeats of unique amino-acid sequences, and characteristics of surface or secreted proteins.

A third protein, LipC (originally identified as Rv0220) is a 403 amino acid, 44 kDa protein, annotated as a probable esterase in the Mtb database based on a putative carboxy-lesterases type-B serine active site. It is a member of a family of 24 proteins, two of which (LipY and LipH) have been shown to be induced during starvation and under acidic conditions.

There is a need in the art to identify constituents of Mtb, primarily proteins, or fragments thereof with B cell epitopes that can serve as (a) antigens in immunoassays for early detection of mycobacterial disease and/or (b) a basis for immunogens or vaccines to induce anti-mycobacterial antibody responses that are prophylactic or therapeutic. The present invention is directed to three such proteins and particular immunodominant peptide fragments thereof.

No proteomic studies of Mtb culture filtrates, cytosol, cell-wall or membrane fraction have identified PTRP although ptrp transcripts are reported to be downregulated in Mtb sigma factor sigF mutant strain compared to wild type Mtb in broth culture, suggesting that ptrp is expressed during growth in broth culture and its expression is regulated by sigF (2, 15, 17, 20, 25-27, 40, 44, 50, 51, 55). Similarly, there is no information available as to the expression of PE-PGRS51 or LipC as above. The present inventors have identified these proteins and specific peptides thereof as useful antigens for early detection or immunization.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

The studies leading to the present invention demonstrated that the PTRP (the coding sequence for which is SEQ ID NO:1, and the amino acid sequence of which is SEQ ID NO:2) is a Mtb complex-specific cell-wall protein expressed by Mtb growing extracellularly in broth culture, intracellularly in vitro in human macrophages derived from peripheral blood mononuclear cells (PBMC) and in vivo during active infection with Mtb. Moreover, PTRP is a highly immunogenic protein that elicits antibodies in TB patients. The amino acid sequence of PTRP has been screened to identify immunogenic regions that can be used to devise diagnostic markers for TB as well as vaccine candidates. Like several other repetitive proteins of gram positive bacteria, PTRP binds to a number of human extracellular matrix (ECM) proteins, including thrombospondin, laminin and fibronectin.

Two additional Mtb proteins, PE-PGRS51 and LipC have been identified as immunoreactive with TB patient sera, The PTRP (proline-threonine repetitive protein; Rv 0538) of *Mycobacterium tuberculosis* (Mtb) is annotated as a hypothetical membrane protein and assigned to the category of cell-wall proteins in the Mtb genome database. As noted above, the present inventors and colleagues reported the presence of anti-PTRP antibodies in sera of rabbits infected with aerosolized Mtb (49, WO 03/073101 and US Pat. Publ. 2005/084904.)

The present invention demonstrates that ptrp is Mtb complex-specific and is present in all clinical isolates tested. The presence of PTRP in Mtb cell-wall preparations and on the surface of intact bacilli confirms that PTRP is a cell-wall protein. The presence of anti-PTRP antibodies in sera from HIV$^-$TB$^+$ and HIV+TB$^+$ patients demonstrates that PTRP is immunogenic in humans.

Four immunodominant regions of the protein that detect ~80% of the smear positive TB patients have been delineated. Moreover, this surface-exposed cell-wall protein is also serves as an adhesin, which may contribute to bacterial adherence to alveolar macrophages and/or to pulmonary epithelial and endothelial cells by its ability to bind to thrombospondin, laminin and fibronectin.

Thus, PTRP is a highly immunogenic cell-wall protein of Mtb that may contribute to the establishment of Mtb infection, and peptide thereof are useful as diagnostic reagents for early detection of Mtb infection.

The present invention provides an antigenic composition useful for early detection of *M. tuberculosis* disease or infection or for immunizing a subject against *M. tuberculosis* infection, comprising
(a) a peptide selected from the group consisting of:

| PT-1  | MDVALGVAVTDRVARLALVD | (SEQ ID NO: 7)   |
|-------|----------------------|------------------|
| PT-3  | SAAPGTVIDQFVLDVAEHPV | (SEQ ID NO: 9)   |
| PT-6  | DRSLAGENHRLVATRLCWPD | (SEQ ID NO: 12)  |
| PT-9  | LQDSGVHDVAVISEAQAATA | (SEQ ID NO: 15)  |
| PT-13 | LSVVGDPDAPPTMVAVAPVA | (SEQ ID NO: 19)  |
| PT-14 | PTMVAVAPVAGADATSTVDT | (SEQ ID NO: 20)  |
| PT-20 | QTPDDPTFALARGAAMAAGA | (SEQ ID NO: 26)  |
| PT-23 | DATTSLPRAEAGQSGSEGEQ | (SEQ ID NO: 29)  |
| PT-34 | QQAPVPPPPPDDPTAGFQGG | (SEQ ID NO: 40)  |
| PT-40 | PIPVPIIIPPFPGWQPGMPT | (SEQ ID NO: 46)  |
| PT-41 | FPGWQPGMPTIPTAPPTTPV | (SEQ ID NO: 47)  |
| PT-45 | TTPPTTPVTTPPTTPPTTPV | (SEQ ID NO: 51)  |
| PG-2  | LAAAASDVANIGSALSAANA | (SEQ ID NO: 62)  |
| PG-9  | TGAGGSYALTEAANVQQNLL | (SEQ ID NO: 69)  |
| PG-14 | DGGLLFGNGGAGYNSAATPG | (SEQ ID NO: 74)  |
| PG-16 | MAGGNGGNAGLIGNGGTGGS | (SEQ ID NO: 76)  |
| PG-24 | LTGNDGVNPAPVTNPALNGA | (SEQ ID NO: 84)  |
| PG-28 | GTPGGAGVNGGNGGAGGDAN | (SEQ ID NO: 88)  |
| PG-29 | GNGGAGGDANGNPANTSIAN | (SEQ ID NO: 89)  |
| PG-31 | AGAGGNGAAGGDGGANGGAG | (SEQ ID NO: 91)  |
| PG-50 | NGGAGGDAGHGGTGGDGGDG | (SEQ ID NO: 110) |
| PG-51 | GGTGGDGGDGGHAGTGGRGG | (SEQ ID NO: 111) |
| PG-52 | GHAGTGGRGGLLAGQHANSG | (SEQ ID NO: 112) |
| PG-53 | LLAGQHANSGNGGGGGTGGA | (SEQ ID NO: 113) |
| PG-55 | GGTHGTPGSGNAGGTGTGNA | (SEQ ID NO: 115) |
| Lp-3  | ARPADYMLALSVAGGSLPVV | (SEQ ID NO: 121) |
| Lp-4  | SVAGGSLPVVGKHLKPLGGV | (SEQ ID NO: 122) |
| Lp-6  | TAIGVWGARHASDFLSATAK | (SEQ ID NO: 124) |
| Lp-24 | IAVAGCSAGGHLSALAGLTA | (SEQ ID NO: 142) |
| Lp-26 | NDPQYQAELPEGSDTSVDAV | (SEQ ID NO: 144) |
| Lp-34 | GSRDCVIPVEQARSFVERLR | (SEQ ID NO: 152) |
| Lp-39 | AHAIALFLNQVHRSRAQFAK | (SEQ ID NO: 157) | wherein The PT-# proteins are fragments of the Mtb protein PTRP (SEQ ID NO:2), the PG-# peptides are fragments of the Mtb protein PE-PGRS51 (SEQ ID NO:4), and the Lp-# peptides are fragments of the Mtb protein LipC with the proviso that the composition is not the full length protein PTRP having the sequence SEQ ID NO:2, PE-PGRS51 having the sequence SEQ ID NO:4 or LipC having the sequence SEQ ID NO:6;

(b) a fragment, preferably of at least 10 residues, a variant, preferably a conservative amino acid substitution variant, or a functional derivative of the peptide of (a) which fragment, variant or derivative is an Mtb antigen in that it binds to an antibody specific for the respective protein PTRP, PE-PGRS51 or LipC; or (c) a combination of two or more of any of the peptides of (a) or the fragments, variants or functional derivatives of (b), which combination may be a mixture or a fusion peptide or polypeptide.

The fusion polypeptide may combine any two of more peptides units that are derived from a single of the above Mtb proteins or from two or more of the distinct Mtb proteins.

In the above an antigenic composition may be in the form of a fusion polypeptide that comprises:

(a) a fusion partner that is one or more of the peptides of (a) or the fragments or variants thereof, linked to (b) a fusion partner polypeptide that is an early Mtb antigen, wherein the fusion polypeptide includes an optional linker or linkers linking any two or more of the fusion partners. Any peptide linker known in the art maybe used, including those cleavable by any of a number of proteolytic enzymes.

Also provided is an antigenic composition as above which is:

(a) a peptide multimer having the formula $P^1{}_n$ wherein $P^1$ is any of the above peptides or the fragment or substitution variant thereof, and n=2-8, (b) a peptide multimer having the formula $(P^1\text{-}X_m)_n\text{-}P^2$ wherein $P^1$ and $P^2$ are any of the above peptides or the fragments or substitution variants thereof, and wherein (i) $P^1$ and $P^2$ may be the same or different and each occurrence of $P^1$ in the $P^1$-$X_m$ structure may be a different peptide, fragment or variant from its adjacent neighbor; and (ii) X is (A) $C_1$-$C_5$ alkyl, $C_1$-$C_5$ alkenyl, $C_1$-$C_5$ alkynyl, $C_1$-$C_5$ polyether containing up to 4 oxygen atoms, wherein m=0 or 1, and, n=1-7; or (B) $Gly_z$ wherein m=0 or 1, and, z=1-6, and wherein the peptide multimer reacts with an antibody specific for the Mtb protein of which any included peptide is a fragment.

In another embodiment, the antigenic composition is a recombinant peptide multimer having the formula:

$(P^1\text{-}Gly_z)_n\text{-}P^2$ wherein $P^1$ and $P^2$ are any of the above peptides or the fragment or substitution variant thereof, and wherein (a) $P^1$ and $P^2$ may be the same or different and each occurrence of $P^1$ in the $P^1$-$Gly_n$ structure may be a different peptide or variant from its adjacent neighbor;

(b) n=1-100 and z=0-6, and wherein the peptide multimer reacts with an antibody specific for the Mtb protein of which any included peptide is a fragment.

An antigenic composition useful for early detection of *M. tuberculosis* disease or infection may also comprise one or more peptides in a mixture or linked in a peptide multimer or fusion protein, which one or more peptides are derived from, or have a sequence corresponding to, a segment/fragment of an early *M. tuberculosis* antigen that is a cell wall protein; such an Mtb early antigen is characterized as being
  (i) reactive with antibodies found in tuberculosis patients who are in a stage of disease prior to the onset of sputum smear-positivity and cavitary pulmonary lesions, and
  (ii) non-reactive with sera from healthy control subjects or healthy subjects with latent inactive tuberculosis, the composition being substantially free of other *M. tuberculosis* proteins which are not early *M. tuberculosis* antigens as characterized above.

The present invention is also directed to a method for the early detection of mycobacterial disease or infection in a subject comprising assaying a biological fluid sample, including serum, urine or saliva, from a subject suspected of having active TB for the presence of antibodies specific for the above antigenic composition, wherein the presence of the antibodies is indicative of the presence of the disease or infection.

In the method, the biological fluid sample is preferably taken from a subject having symptoms of active tuberculosis, but before the onset of symptoms identifiable as advanced tuberculosis that is distinguished by (a) smear positivity of sputum or other pulmonary associated fluid for acid-fast bacilli, (b) cavitary pulmonary lesions, or both (a) and (b).

The above method may comprise, prior to the assaying step, removing from the sample antibodies specific for cross-reactive epitopes or antigens shared by proteins present in *M. tuberculosis* with proteins of other bacterial genera. This is done, for example, by immunoadsorption of the sample with *E. coli* bacteria or antigen preparations therefrom.

The method may further comprise assaying the sample for the presence of antibodies specific for one or more additional early *M. tuberculosis* antigens selected from the group consisting of:
  (a) Mtb protein GlcB encoded by Mtb gene Rv1837c;
  (b) Mtb protein MPT51 encoded by Mtb gene Rv3803c;
  (c) Mtb protein PE-PGRS36 encoded by Mtb gene Rv2098c;
  (d) Mtb protein PirG encoded by Mtb gene Rv3810;
  (e) Mtb protein Mtr encoded by Mtb gene Rv3246c;
  (f) Mtb protein known as Mtb antigen 85C;
  (g) Mtb glycoprotein known as Mtb antigen MPT32; and
  (h) a fusion protein comprising one or more of (a)-(g).

The subject in the above method is preferably a human, such as a subject infected with HIV-1 or is at high risk for tuberculosis.

The method may further include performance of a test that detects mycobacterial bacilli in a sample of sputum or other body fluid of the subject—a conventional procedure in the art.

Provided herein is a kit useful for early detection of *M. tuberculosis* disease comprising:
  (a) an antigenic composition as above, in combination with
  (b) reagents necessary for detection of antibodies which bind to the peptides.
The kit may further comprise one or more early antigens of *M. tuberculosis*, preferably. one or more early antigens is selected from:
  (a) Mtb protein GlcB encoded by Mtb gene Rv1837c;
  (b) Mtb protein MPT51 encoded by Mtb gene Rv3803c;
  (c) Mtb protein PE-PGRS36 encoded by Mtb gene Rv2098c;
  (d) Mtb protein PirG encoded by Mtb gene Rv3810;
  (e) Mtb protein Mtr encoded by Mtb gene Rv3246c;
  (f) Mtb protein characterized as Mtb antigen 85C;
  (g) Mtb glycoprotein characterized as Mtb antigen MPT32; and
  (h) a fusion protein comprising one or more of (a)-(g).

The present invention is also directed to the use of a peptide, fragment, variant or functional derivative as defined above for the manufacture of a medicament for early detection of *M. tuberculosis* disease or infection or for immunizing a subject against *M. tuberculosis* infection.

BRIEF DESCRIPTION OF THE DRAWINGS

FIG. 1 is a set of schematic diagram of primary and secondary structure of PTRP. In the top panel, representing the primary structure, the striped area and amino acid (aa) numbers above area indicate location of the repetitive region. The repeating motifs are: 3 repeats of TT/APPTTPP/VTTP/SV/A (SEQ ID NO:159) and 2 repeats of T V/T A/P PTTVAP T/-(SEQ ID NO:175). The vertical lines indicate O-glycosylation sites; the dotted regions show location of predicted transmembrane helices and the boxed regions with vertical stripes denote signal peptide.

FIG. 2 is a southern blot showing expression of the ptrp gene by Mtb organisms residing in human PBMC-derived macrophages (MDM). RT-PCR was performed with total RNA isolated from Mtb grown in Middlebrook 7H9 media (lanes 2-4) or in MDM (lanes 5-7) or from uninfected MDM (lanes 8-10). The amplified products were electrophoresed on a 1% agarose gel and stained with ethidium bromide. Lanes 2, 5 and 8 contain products amplified from cDNA diluted 1:10; lanes 3, 6 and 9 from cDNA diluted 1:100 and 4, 7 and 10 contain respective no reverse transcriptase controls. Lanes 11 and 12 contain no DNA (negative) and Mtb H37Rv genomic DNA (positive) controls respectively. Lane 1 shows DNA markers. The arrow indicates position of the amplified ptrp.

FIG. 3A is a southern blot prepared from Xho I digested genomic DNA of mycobacterial species was probed with DIG-labeled ptrp (1645 bp). Lanes are the following:

| 1. Mtb H37Rv | 7. *M. microti* | 13. *M. vaccae* |
| 2. Mtb Erdman | 8. *M. africanum* | 14. *M. intracellulare* |
| 3. Mtb CDC1551 | 9. *M. avium* | 15. *M. phlei* |
| 4. Mtb H37Ra | 10. *M. xenopia* | 16 *M. fotuitum* |
| 5. *M. bovis* | 11. *M. kansassi* | 17. *M. smegmatis* MC$_2$ 155 |
| 6. *M. bovis* BCG | 12. *M. scrofulaceum* | 18.. *M. chelonae* |

Figure 3A:
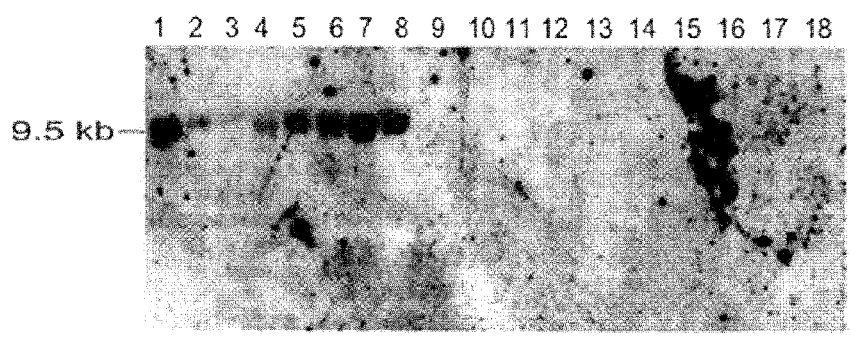
FIGS. 3A-3C are southern blots showing distribution of ptrp in various mycobacterial species.
Figure 3B:
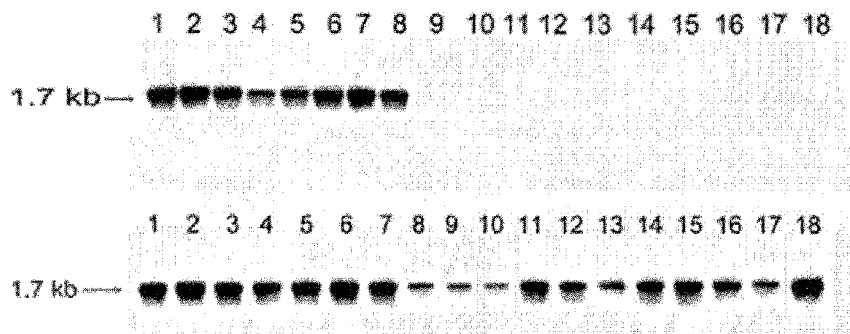

FIGS. 3B and #C were prepared from ptrp amplified from genomic DNA of mycobacterial species and Mtb clinical isolates were probed with DIG-labeled ptrp (1697 bp) amplified from Mtb H37Rv genomic DNA. Lanes in FIG. 2C are:

| 1. Mtb H37Rv | 7. Mtb CSU26 | 13. Mtb AI46 (TN11533) |
| 2. Mtb CSU11 | 8. Mtb CSU 27 | 14. Mtb 11159 (BE) |
| 3. Mtb CSU17 | 9. Mtb 10738 (W200) | 15. Mtb 11164 (H17) |
| 4. Mtb CSU19 | 10. Mtb 10591 (W187) | 16. Mtb 11165 (MB2) |
| 5. Mtb CSU22 | 11. Mtb 10813 (W148) | 17. Mtb 11168 (001) |
| 6. Mtb CSU25 | 12. Mtb AI10 (TN10692) | 18. Mtb 11177 (001). |

Arrows indicate position of the hybridizing fragments.

FIG. 4A-4D are a series of blot or graphs showing expression of rPTRP and localization of PTRP in Mtb. FIG. 4A: Purified rPTRP was fractionated on SDS-PA gel and stained with Coomassie blue. Molecular weight markers (lane 1); rPTRP (lane 2). FIG. 4B is a western blot of Mtb subcellular protein fractions probed with pre-immune IgG (lanes 1-5) and anti-PTRP IgG (lanes 6-10). Culture filtrate (lanes 1 and 6); SDS extracted cell-wall proteins (lanes 2 and 7); total cell-wall (lanes 3 and 8); whole cell lysates (lanes 4 and 9) and rPTRP (lanes 5 & 10). FIG. 4C is a graph showing detection of PTRP by ELISA in Mtb total cell-wall (squares), SDS extracted cell-wall (triangles), whole cell lysate (diamonds) and culture filtrate protein (circles) preparations. The results are plotted as the mean absorbance (=optical density or OD) difference, or ΔOD±SD (std. deviation), where ΔOD is the OD measured with anti-PTRP IgG minus the OD with pre-immune IgG at various concentrations of the subcellular preparations. FIG. 4D is a graph showing the presence of PTRP on the surface of Mtb H37Rv (squares) and Mtb CDC1551 (triangles) bacilli by bacterial ELISA. The mean Delta OD±SD, defined as above was determined with different numbers of bacilli.

FIGS. 5A and 5B are western blots showing reactivity of rPTRP with sera from TB patients and healthy control individuals. FIG. 5A: western blots of rPTRP were probed with sera from 6 HIV$^-$TB$^+$ patients (lanes 2-7) and 4 PPD$^+$ healthy controls (lanes 8-11) and anti-PTRP IgG (lane 12). Lane 1 contains molecular weight markers. FIG. 5B: blots of rPTRP were probed with sera from 6 HIV$^+$TB$^+$ patients (lanes 2-7) and 6 HIV$^+$TB$^-$ patients (lanes 8-13), 6 PPD$^-$ healthy subjects (lanes 14-19) and 6 PPD$^+$ healthy subjects (lanes 20-25). Anti-PTRP IgG was used to probe lane 26. Lane 1 contains molecular weight markers.

FIG. 6A-6B is a set of graphs showing reactivity of overlapping peptides of PTRP with sera from TB patients and healthy controls. See also Table 1, below. FIG. 6A: PTRP peptides were probed with sera from 60 HIV$^-$TB$^+$ patients and 36 PPD$^+$/PPD$^-$ healthy controls. The cut off value for positive reactivity was mean OD at 405 nm obtained with sera from PPD$^+$/PPD$^-$ plus 3 SD. Results are shown as percent positivity (=percent of positive sera) from HIV$^-$TB$^+$ patient sera (black bars) and from PPD$^+$/PPD$^-$ healthy controls (gray bars) with each PTRP peptide. The horizontal line indicates cut-off used for selecting immunodominant peptides. FIG. 6B: PTRP peptides showing reactivity with sera from 40% or more HIV$^-$TB$^+$ patients (shown in FIG. 6A) were tested two more times with sera from the same patients and healthy controls. The same criteria for cut off as above was used. Results show percent of sera from HIV$^-$TB$^+$ patients (black bars) and sera from and PPD$^+$/PPD$^-$ healthy controls (gray bars) exhibiting positive reactivity in 2 of 3 or 3 of 3 replications with each PTRP peptide. The bar designated as C1 is the reactivity (additive) of all 16 immunodominant peptides. The additive reactivity of the 4 most highly immunodominant peptides (peptide 9, 13, 40 and 41) are shown in the bar labeled as C2.

FIG. 7A-7D is a group of four graphs showing reactivity of highly immunodominant peptides of PTRP with sera of TB patients and healthy controls. Antibodies to PTRP peptide 9 (FIG. 7A), peptide 13 (FIG. 7B), peptide 40 (FIG. 7C) and peptide 41 (FIG. 7D) in sera from HIV$^-$TB$^+$ patients and PPD$^+$ and PPD$^-$ controls were determined by ELISA. The cut off for positivity is as shown for the above Figures (Mean OD plus 3 SD). Results are shown as Delta OD representing the OD obtained with any serum specimen minus the cut off for every specimen with each peptide. The peptides are listed in Table 1, below.

Figure 8A:
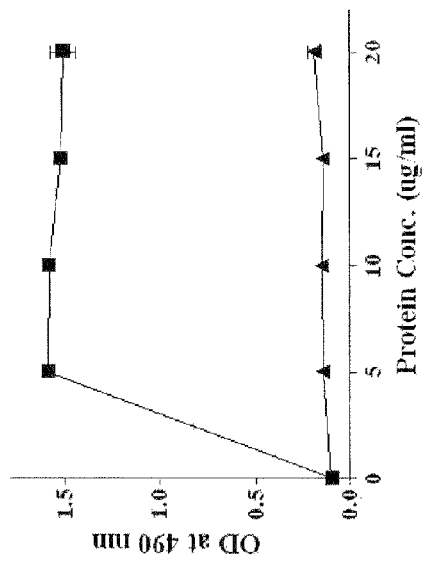

FIG. 8A-8D is a western blot and graphs showing binding of rPTRP to extracellular matrix (ECM) proteins. FIG. 8A: Western blots of rPTRP were incubated with laminin (lane 2), fibronectin (lane 4) and thrombospondin (lane 6). Blots incubated with PBS served as negative controls (lanes 3, 5 and 7). All strips were probed with the appropriate antibodies to the three ECM proteins to detect binding. Binding of rPTRP to ECM proteins (squares) thrombospondin (FIG. 8B), laminin (FIG. 8C) and fibronectin (FIG. 8D) was determined by ELISA. BSA (bovine serum albumin) a control, non-ECM protein (triangles) was used as negative control. Mean OD (490 nm)±SD values obtained from triplicates at various concentration of rPTRP in one representative experiment are shown.

FIG. 9 shows an annotated nucleotide and deduced amino acid sequence of the PTRP gene (originally designated as Rv0538) and PTRP protein. The nucleotide sequence is SEQ ID NO:1. The amino acid sequence is SEQ ID NO:2. Repetitive motifs are shown in boxes. Arrow indicates the initiation of fusion with β-gal in clone AD10. The transmembrane helices sequences are shown in bold. The asterisk indicates the stop codon.

FIG. 10 shows an annotated nucleotide and deduced amino acid sequence of the: the PE-PGRS51 gene (originally designated as Rv3367). The nucleotide sequence is SEQ ID NO:3. The amino acid sequence is SEQ ID NO:4. The signal peptide sequence is shown in italics, hollow arrow between a.a. 44 & 45 indicates signal peptidase cleavage site. The repetitive sequences are shown in boxes. The motif PE is underlined. Solid arrow at a.a. 230 indicates the start of fusion with β-gal in clone AD9. The transmembrane helices sequences are shown in bold. The asterisk indicates the termination codon.

Figure 11:
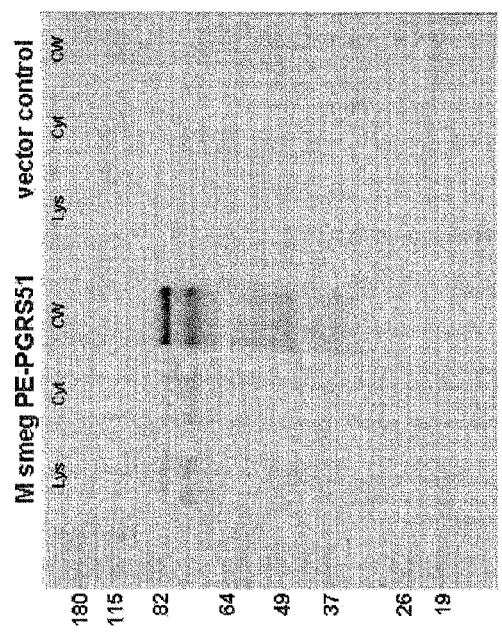

FIG. 11 is a series of western blots showing that PE-PGRS51 expressed in *M. smegmatis* localizes to the cell-wall fraction.

Figure 12:
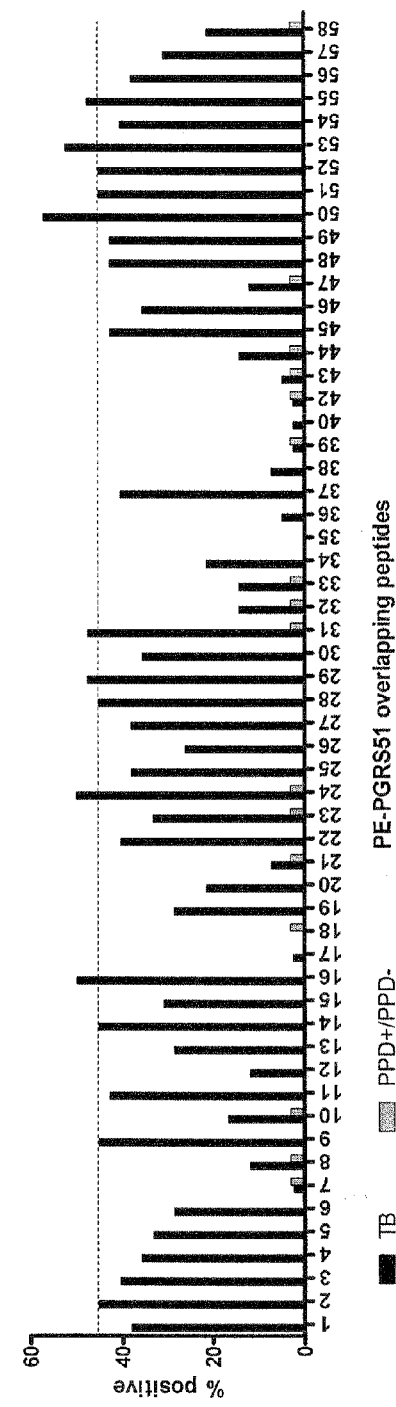

FIG. 12 is a graph showing the reactivity of overlapping peptides of PE-PGRS51 (see Table 2, below) with sera from 36 healthy control individuals and 42 TB patients determined using ELISA. The mean binding (expressed as absorbance or OD at 405 nm) of control sera form PPD$^+$ and PPD$^-$ control subjects was determined and +4 S.D. was set as the cut-off value to for positive reactivity. Peptides numbered 2, 9, 14, 16, 24, 28, 29, 31, 50, 51, 52, 53 and 55 reacting with at least 45% of TB patient sera (=sensitivity) were selected for further analysis.

Figure 13:
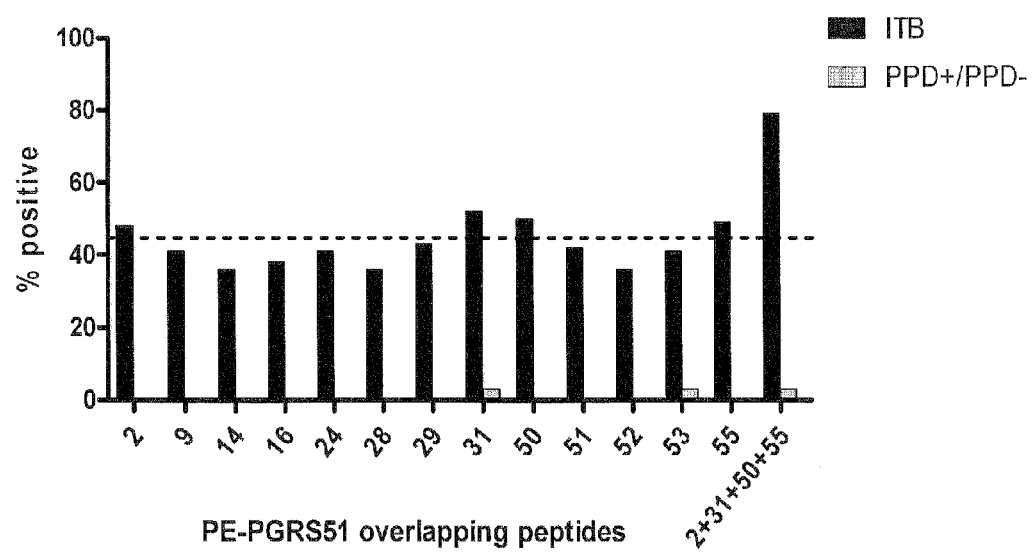

FIG. 13 is a graph showing reactivity of TB sera with the immunodominant epitopes of PE-PGRS51. Results are expressed as % positivity).

Figure 14:
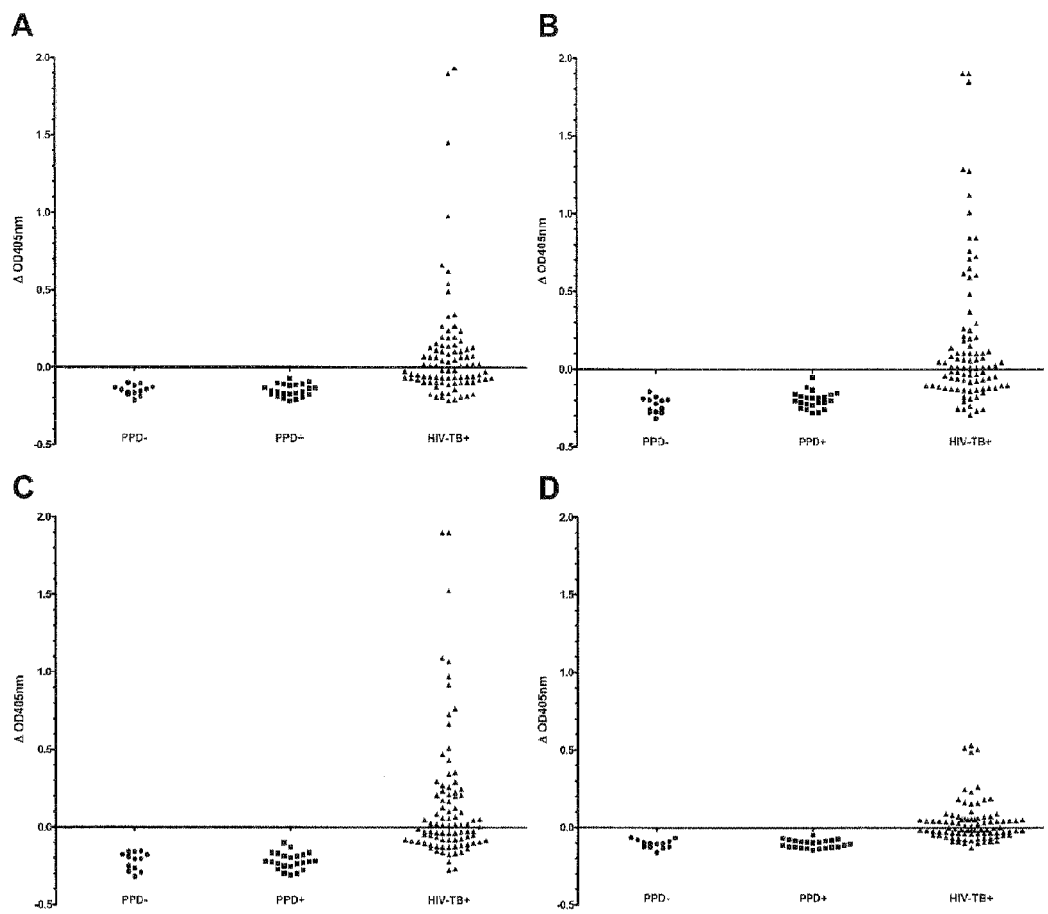

FIG. 14A-14D is a series of graphs comparing the reactivity of PPD$^-$, PPD$^+$ and HIV$^-$TB$^+$ patients with the four PE-PGRS51 peptides. Results shown are differences in absorbance (at 405 nm) of individual sera compared to background (no antisera). FIG. 14A: Peptide PG-2 (SEQ ID NO:62); FIG. 14B: Peptide PG-31 (SEQ ID NO:91); FIG. 14C: Peptide PG-50 (SEQ ID NO:110); and FIG. 14D: Peptide PG-55 (SEQ ID NO:115). See Table 2.

Figure 15:
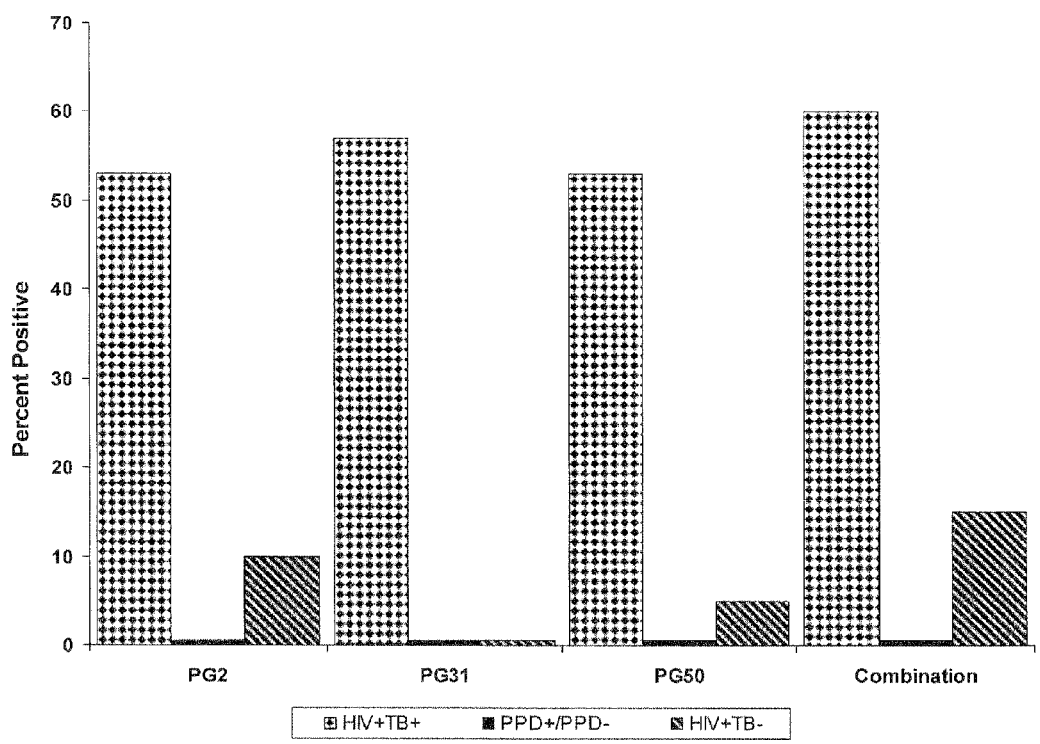

FIG. 15 is a graph showing recognition of peptides by serum antibodies from three groups of patients: HIV$^+$TB$^+$ patients (checkered columns), PPD$^+$ and PPD$^-$HIV$^-$ healthy subjects (black columns) and HIV$^+$TB$^-$ asymptomatic subjects (cross-hatched columns). Reactivity is shown against the following 3 PE-PGRS51 peptides: PG2, PG31 and PG50, as well as a mixture ("combination") of all three peptides.

FIG. 16 shows the nucleotide coding sequence (SEQ ID NO:5) and deduced amino acid sequence (SEQ ID NO:6) of the LipC gene and LipC protein (originally designated as Rv0220). The stop codon is underscored. The sequences are available, for example in EMBL-EBI ID#ABQ71945.

Figure 17:
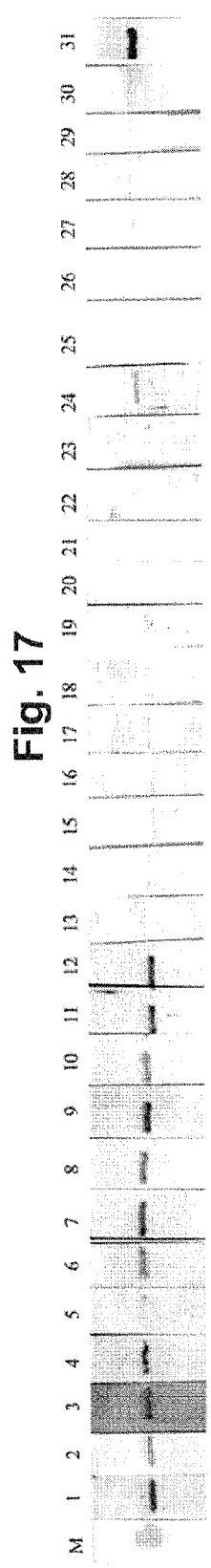

FIG. 17 is a series of western blots showing reactivity of purified His-tagged LipC with sera from smear-positive HIV$^-$TB$^+$ patients (lanes 1-6), Smear positive HIV+TB$^+$ patients (lanes 7-12), HIV+TB− subjects (lanes 13-18), HIV−PPD+ subjects (lanes 19-24) and HIV−PPD− subjects (lanes 25-30). Lane 31 shows reactivity of His-tagged LipC with anti-His antibodies. The lane labeled M shows molecular weight markers. Sera from 11/12 TB patients showed strong reactivity with the LipC protein, and some control sera show background cross-reactivity with the His-LipC.

Figure 18:

FIG. 18: Reactivity of anti-His antibodies with His-LipC. Lane 1: total lysate from parental *M. smegmatis*; lane 2: cytosolic proteins, lane 3: cell-wall proteins, lane 4: cytosolic proteins and lane 5: culture filtrate proteins from recombinant *M. smegmatis* expressing His-LipC.

DESCRIPTION OF THE PREFERRED EMBODIMENTS

The present inventors and their colleagues previously identified several Mtb proteins (including GlcB, MPT51, PTRP and PE-PGRS51 that act as "early" antigens in Mtb infections, and permit earlier diagnosis of infection than was previously available by detection of serum antibodies to these proteins in infected subjects. These proteins are also useful in immunogenic/vaccine compositions to induce immunity to Mtb. See, for example U.S. Pat. Nos. 6,245,331 and 6,506,384, and published patent applications WO 03/073101 and US 2005/084904.

Thereafter, specific, immunodominant peptides of the GlcB secreted protein and one peptide of the MPT51 secreted protein were identified by the present inventors and colleagues and found to be useful for early detection assays and as immunogenic moieties (PCT Publication WO2003/12395)

The present inventors have now identified new peptides of three additional Mtb proteins, PTRP, PE-PGRS51 and LipC, that are strongly reactive with TB sera and are therefore useful as antigens for early serological detection of TB disease and as useful epitopes for constructing prophylactic or therapeutic vaccines for TB.

The present invention therefore provides novel compositions and methods of their use.

The nucleotide and amino acid sequence of the PTRP coding sequence (SEQ ID NO:1) and the full length PTRP protein (SEQ ID NO:2) are shown in FIG. 9.

The nucleotide and amino acid sequence of the PE-PGRS51 coding sequence (SEQ ID NO:3) and the full length PE-PGRS51 protein (SEQ ID NO:4) are shown in FIG. 10.

The nucleotide and amino acid sequence of the LipC coding sequence (SEQ ID NO:5) and the full length LipC protein (SEQ ID NO:6) are shown in FIG. 16.

Standard reference works setting forth the general principles of immunology include W. E. Paul, *Fundamental Immunology*, Lippincott Williams & Wilkins; 5th ed. (2003); A. K. Abbas et al., *Cellular and Molecular Immunology* (5th Ed.), W.B. Saunders Co., Philadelphia, 2005; C. A. Janeway et al., *Immunobiology. The Immune System in Health and Disease*, Fourth ed., Garland Science, 2007; K. Murphy, *Janeway's Immunobiology*, 7th ed. (based on C. A. Janeway, et al., *Immunobiology. The Immune System in Health and Disease*); J. Klein, 2nd edition, Blackwell Scientific Publications, Inc., Cambridge, Mass., (1997); Klein, J., *Immunology*, Blackwell Scientific Publications, Inc., Cambridge, Mass., (1990); I. Roitt, et al., eds, *Immunology*, C.V. Mosby Co., St. Louis, Mo. (2001); I. Roitt, et al., eds., *Roitt's Essential Immunology*, Blackwell Scientific Publications, Oxford (2001). Monoclonal antibodies (mAbs) and methods for their production and use are described in Kohler and Milstein, *Nature* 256:495-497 (1975); U.S. Pat. No. 4,376,110; Harlow, E. et al., *Antibodies: A Laboratory Manual*, Cold Spring Harbor Laboratory Press, Cold Spring Harbor, N.Y., 1988); *Monoclonal Antibodies and Hybridomas: A New Dimension in Biological Analyses*, Plenum Press, New York, N.Y. (1980); H. Zola et al., in *Monoclonal Hybridoma Antibodies: Techniques and Applications*, CRC Press, 1982)). Immunoassay methods are also described in Coligan, J. E. et al., eds., *Current Protocols in Immunology*, Wiley-Interscience, New York 1991 (or current edition); Butt, W. R. (ed.) *Practical Immunoassay: The State of the Art*, Dekker, New York, 1984; Bizollon, Ch. A., ed., *Monoclonal Antibodies and New Trends in Immunoassays*, Elsevier, New York, 1984; Butler, J. E., ELISA (Chapter 29), In: van Oss, C. J. et al., (eds), *IMMUNOCHEMISTRY*, Marcel Dekker, Inc., New York, 1994, pp. 759-803; Butler, J. E. (ed.), *Immunochemistry of Solid-Phase Immunoassay*, CRC Press, Boca Raton, 1991; Weintraub, B., *Principles of Radioimmunoassays*, Seventh Training Course on Radioligand Assay Techniques, The Endocrine Society, March, 1986; Work, T. S. et al., *Laboratory Techniques and Biochemistry in Molecular Biology*, North Holland Publishing Company, NY, (1978) (Chapter by T. Chard).

The present invention provides a diagnostic immunoassay method to detect and/or quantitate antibodies specific for mycobacterial antigens, in particular, antibodies developing early in the progression of *M. tuberculosis* infection to disease and before clinical manifestations of that disease. On the basis of such an assay, it is possible to detect TB earlier than ever before and to institute appropriate therapy.

The immunoassay method is based upon the present inventors' discovery that certain Mtb antigens induce in humans an earlier response than do other antigens which elicit antibodies only after the disease is already clinically advanced. In HIV-infected subjects with dysfunctional immune systems, antibodies to some of these antigens are detectable long before TB is clinically manifest. A number of secreted proteins, including membrane-bound secreted proteins, and cell wall proteins have been identified as early antigens with diagnostic value. In particular a preferred early antigens are the proteins discussed above, and now, the immunoreactive peptides thereof. Proteins used in the present invention are preferably enriched or semipurified (at least 50% pure, preferably 70% pure, more preferably 80% pure) or highly purified (at least 95% pure, preferably at least 99% pure).

Also provided are epitope-bearing peptides from PTRP, PE-PGRS51 and LipC (disclosed above) that are reactive with TB sera and which are used in early diagnosis in the form of peptides (a single peptide or a mixture of different peptides), a fusion polypeptide and peptide multimers (synthetic or recombinant) comprising one or more different epitope-bearing peptides, or fusion polyproteins that comprise at least two full length early antigen proteins and may include additional early antigenic epitopes that are based on peptides of the same or other Mtb proteins.

The present methods evolved from the inventors' earlier conception of the importance of first removing antibodies specific for cross-reactive antigens, usually bacterial antigens which are not Mtb-specific prior to analyzing the antigenic reactivity and specificity of serum from patients infected with Mtb when testing on crude or semipurified antigenic preparations. However, once purified antigens, preferably synthetic peptides are provided, or epitope-specific competitive EIA's are established based on this invention (see, for example, Wilkins, E. et al., 1991, *Eur. J. Clin. Microbial. Infect. Dis.* 10:559-563), the need for or advantage of such prior absorption steps should be obviated.

As used herein, the terms "early" and "late" in reference to (1) Mtb infection or disease, or the subject having the infection or disease, (2) the antibody response to an Mtb antigen, (3) an Mtb antigen itself or (4) a diagnostic assay, are defined in terms of the stage of development of TB. Early and late (or advanced) TB are defined in the table below.

Thus, a subject with early TB is asymptomatic or, more typically, has one or more "constitutional symptoms" (e.g., fever, cough, weight loss). In early TB, Mtb bacilli are too few to be detectable as acid-fast bacilli in smears of sputum or other body fluid, primarily those fluids associated with the lungs (such as bronchial washings, bronchoalveolar lavage, pleural effusion). However, in these subjects, Mtb bacilli are present and culturable, i.e., can be grown in culture from the above body fluids. Finally, early TB subjects may have radiographically evident pulmonary lesions which may include infiltration but without cavitation. Any antibody present in such early stages is termed an "early antibody" and any Mtb antigen recognized by such antibodies is termed an "early antigen." The fact that an antibody is characterized as "early" does not mean that this antibody is absent in advanced TB. Rather, such antibodies are expected to persist across the progression of early TB to the advanced stage.

Accordingly, the term "late" or "advanced" is characterized in that the subject has frank clinical disease and more advanced cavitary lesions in the lungs. In late TB, Mtb bacilli are not only culturable from smears of sputum and/or the other body fluids noted above, but also present in sufficient numbers to be detectable as acid-fast bacilli in smears of these fluids. Again, "late TB" or "late mycobacterial disease" is used interchangeably with "advanced TB" or "advanced mycobacterial disease." An antibody that first appears after the onset of diagnostic clinical and other characterizing symptoms (including cavitary pulmonary lesions) is a late antibody, and an antigen recognized by a late antibody (but not by an early antibody) is a late antigen.

| Early TB | 1. | Smear of sputum, bronchial washing, bronchoalveolar lavage or pleural effusion is negative for acid fast *bacilli* |
| --- | --- | --- |
| | 2. | Direct culture of sputum, bronchial washing, bronchoalveolar lavage or pleural effusion is positive for acid fast *bacilli* |
| | 3. | Chest x-ray is normal or shows infiltration in the lungs |
| | 4. | Constitutional symptoms are present (fever, cough, appetite and weight loss) |
| Late/ Advanced TB | 1. | Smear of sputum, bronchial washing, bronchoalveolar lavage or pleural effusion is positive (with possible hemoptysis) |
| | 2. | Direct culture of sputum, bronchial washing, bronchoalveolar lavage or pleural effusion is positive |
| | 3. | Chest x-ray shows cavitary lesions in the lungs |
| | 4. | Constitutional symptoms are present (see above) |

To be useful in accordance with this invention, an early diagnostic assay must permit rapid diagnosis of Mtb disease at a stage earlier than that which could have been diagnosed by conventional clinical diagnostic methods, namely, by radiologic examination and bacterial smear and culture or by other laboratory methods available prior to this invention. (Culture positivity is the final confirmatory test but takes two weeks and more.)

The immunoassay used in the present invention typically comprises incubating a biological fluid, preferably serum or urine, from a subject suspected of having TB, in the presence of a *Mycobacterium tuberculosis* (also abbreviated "Mtb") antigen-containing reagent which includes one or more Mtb early antigens. The antigens in this reagent may be combined as mixtures or as polyproteins or peptide multimers based on units of epitope-bearing peptide. The binding of antibodies in the sample to the mycobacterial antigen(s) is then detected.

By the term "biological fluid" is intended any fluid derived from the body of a normal or diseased subject which may contain antibodies, such as blood, serum, plasma, lymph, urine, saliva, sputum, tears, cerebrospinal fluid, bronchioalveolar lavage fluid, pleural fluid, bile, ascites fluid, pus and the like. Also included within the meaning of this term as used herein is a tissue extract, or the culture fluid in which cells or tissue from the subject have been incubated.

Mycobacterial Antigenic Compositions

The mycobacterial antigenic composition or preparation of the present invention may be one or a combination of isolated proteins or peptides of a *M. tuberculosis* protein. As stated above, the combination may be produced as a mixture or as a fusion polypeptide/polyprotein or a peptide multimer.

The antigen composition may be a substantially purified or recombinantly produced preparation of one or more Mtb proteins or epitope-bearing peptides thereof. Alternatively, the antigen composition may be a partially purified or substantially pure preparation containing one or more Mtb epitopes which are capable of being bound by antibodies of a subject with TB. Such epitopes may be in the form of peptide fragments of the early antigen proteins or other "functional derivatives" of *M. tuberculosis* proteins or peptides as described below.

By "functional derivative" is meant a "fragment," "variant," "analogue," or "chemical derivative" of an early antigen protein, which terms are defined below. A functional derivative retains at least a portion of the function of the protein which permits its utility in accordance with the present invention—primarily the capacity to bind to an early antibody. A "fragment" refers to any subset of the molecule, that is, a shorter peptide. A "variant" refers to a molecule substantially similar to either the entire protein or fragment thereof. A variant peptide may be conveniently prepared by direct chemical synthesis or by recombinant means. A "chemical derivative" of the antigenic protein or peptide contains additional chemical moieties not normally part of the native protein (or of a peptide fragment). Covalent modifications of the peptide are included within the scope of this invention. Such modifications may be introduced into the molecule by reacting targeted amino acid residues of the peptide with an organic derivatizing agent that is capable of reacting with selected side chains or terminal residues.

The peptides of the present invention are fragments of one of three Mtb proteins, as disclosed above.

Production of Peptides and Derivatives

General Chemical Synthetic Procedures

The peptides of the invention may be prepared using recombinant DNA technology. However, some of the shorter peptides may be prepared using solid-phase synthesis, such as that generally described by Merrifield, *J. Amer. Chem. Soc.*, 85:2149-54 (1963), although other equivalent chemical syntheses known in the art are also useful. Solid-phase peptide synthesis may be initiated from the C-terminus of the peptide by coupling a protected α-amino acid to a suitable resin. Such a starting material can be prepared by attaching an α-amino-protected amino acid by an ester linkage to a chloromethylated resin or to a hydroxymethyl resin, or by an amide bond to a BHA resin or MBHA resin. Such methods, well-known in the art, are disclosed, for example, in U.S. Pat. No. 5,994,309 (issued Nov. 30, 1999) which is incorporated by reference in its entirety.

Amino Acid Substitution and Addition Variants

Also included in this invention are peptides in which at least one amino acid residue and preferably, only one, has been removed and a different residue inserted in its place compared to the native Mtb sequence. For a detailed description of protein chemistry and structure, see Schulz, G. E. et al., *Principles of Protein Structure*, Springer-Verlag, New York, 1979, and Creighton, T. E., *Proteins: Structure and Molecular Principles*, $2^{nd}$ ed., W.H. Freeman & Co., San Francisco, 1992, which are hereby incorporated by reference. The types of substitutions which may be made in the peptide molecule of the present invention are conservative substitutions, which are typically exchanges within one of the following groups:

1. Small aliphatic, nonpolar or slightly polar residues: e.g., Ala, Ser, Thr, Gly;
2. Polar, negatively charged residues and their amides: e.g., Asp, Asn, Glu, Gln;
3. Polar, positively charged residues: e.g., His, Arg, Lys;

Pro, because of its unusual geometry, tightly constrains the chain. Substantial changes in functional properties are made by selecting substitutions that are less conservative, such as between, rather than within, the above groups (or two other amino acid groups not shown above), which will differ more significantly in their effect on maintaining (a) the structure of the peptide backbone in the area of the substitution (b) the charge or hydrophobicity of the molecule at the target site, or (c) the bulk of the side chain. Preferred substitutions according to the present invention are those that do not produce radical changes in the characteristics of the peptide molecule. Even when it is difficult to predict the exact effect of a substitution in advance of doing so, one skilled in the art will appreciate that the effect can be evaluated by routine screening assays, preferably biological assays described herein, preferably serological assays using antisera, antisera pools, or monoclonal antibodies. Modifications of peptide properties including redox or thermal stability, hydrophobicity, susceptibility to proteolytic degradation or the tendency to aggregate with carriers (or into multimers) are assayed by methods well known to the ordinarily skilled artisan.

Addition variants of the present Mtb peptides preferably include from 1-4 amino acids, but may include as many as 10 amino acids, added either at the N-terminus, the C-terminus or both. Amino acids that are added to the basic peptide unit are ones that permit the peptide to maintain its biological reactivity in accordance with this invention, namely antigenicity (recognition by antibodies or T lymphocytes) or immunogenicity in the case of vaccine embodiments.

For use in a vaccine, preferred peptides or variants are those that have increased stability and/or immunogenicity. Conventional approaches of protein engineering are applied. In one embodiment, stability is increased by introducing one or more Cys residues into strategic positions, where the formation of disulfide bonds between two Cys residues (e.g., intrachain) increases stability. Another approach is based on introduction of residues that form a helices at sites that do not impede the peptide immunologic activity, for example at the N- and C-termini.

In a peptide or polypeptide having a total of n residues, as many as (n−5) amino acids may be substituted, provided that the characteristic immunoreactivity with the appropriate anti-Mtb antibodies is not lost.

Chemical derivatives of the peptides are also included. Lysinyl and amino terminal residues may be derivatized with succinic or other carboxylic acid anhydrides. Derivatization with a cyclic carboxylic anhydride has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Carboxyl side groups, aspartyl or glutamyl, may be selectively modified by reaction with carbodiimides (R—N═C═N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues can be converted to asparaginyl and glutaminyl residues by reaction with ammonia.

Other modifications include hydroxylation of proline and lysine, phosphorylation of hydroxyl groups of seryl or threonyl residues, methylation of the amino group of lysine (Creighton, supra), acetylation of the N-terminal amine, and amidation of the C-terminal carboxyl groups.

Multimeric Peptides and Fusion Proteins (Polyproteins)

The present invention also includes longer peptides or polypeptides in which a sequence of an Mtb early antigenic peptide or a substitution or addition variant thereof, or a chemical derivative thereof, is repeated from two to about 100 times, with or without intervening spacers or linkers. Such molecules are termed in the art, interchangeably, multimers, concatemers or multiepitope polyproteins and will be referred to herein primarily as peptide multimers. When produced recombinantly, they are also considered to be fusion polypeptides or fusion proteins.

A multimer of the peptide referred to symbolically in this section as "P" is shown by the following formula $$(P\text{-}X_m)_n\text{-}P$$

wherein m=0 or 1, n=1-100. X is a spacer group, consisting of 1-20 glycine residues or chemical cross-linking agents. Thus, when m=0, no spacer is added to the peptide. When n=1, the multimer is a dimer, etc.

These multimers may be built from any of the antigenic peptides or variants described herein. Moreover, a peptide multimer may comprise different combinations of peptide monomers (either from the native sequence or variants thereof). Thus a multimer may include several sequential repeats of a first peptide, followed by one or more repeats of a second peptide, etc. Such multimeric peptides can be made by chemical synthesis of individual peptides, recombinant DNA techniques or a combination, e.g., chemical linkage of recombinantly produced multimers.

When produced by chemical synthesis, the multimers preferably have from 2-12 repeats, more preferably 2-8 repeats of the core peptide sequence, and the total number of amino acids in the multimer should not exceed about 110 residues (or their equivalents, when including linkers or spacers).

A preferred synthetic chemical peptide multimer has the formula $$P^1_n$$

wherein $P^1$ is a native Mtb peptide or a fragment, substitution (preferably conservative) or addition variant of such a peptide, and n=2-8, and wherein the peptide alone or in multimeric form has the desired immunologic reactivity.

In another embodiment, a preferred synthetic chemical peptide multimer has the formula $$(P^1\text{-}X_m)_n\text{-}P^2$$

$P^1$ and $P^2$ are Mtb peptides or addition variants of these peptides, wherein (a) $P^1$ and $P^2$ may be the same or different; moreover, each occurrence of $P^1$ in the multimer may be a different peptide (or variant) from its adjacent neighbor;

(b) X may be $C_1$-$C_5$ alkyl, $C_1$-$C_5$ alkenyl, $C_1$-$C_5$ alkynyl, $C_1$-$C_5$ polyether containing up to 4 oxygen atoms, wherein m=0 or 1 and n=1-7; X may also be $Gly_z$ wherein, z=1-6, and wherein the peptide alone or in multimeric form has the immunological activity of reacting with anti-Mtb antibodies, preferably early antibodies.

When produced recombinantly, spacers are preferably $Gly_z$ as described above, where z=1-6, and the multimers may have as many repeats of the core peptide sequence as the expression system permits, for example from two to about 100 repeats. A preferred recombinantly produced peptide multimer has the formula:

$$(P^1\text{-}Gly_z)_n\text{-}P^2$$

wherein:

(a) $P^1$ and $P^2$ are Mtb peptides as described herein or fragments, substitution or addition variants of these peptides, wherein $P^1$ and $P^2$ may be the same or different; moreover, each occurrence of $P^1$ in the multimer may be different peptide (or variant) from its adjacent neighbor.

wherein n=1-100 and z=0-6 (when z=0 there is no Gly spacer);

and wherein the peptide alone or in multimeric form has the desired immunologic reactivity. In the foregoing peptide multimers, $P^1$ and $P^2$ is preferably selected from any one of the followings SEQ ID NO's: SEQ ID NO:7; SEQ ID NO:9; SEQ ID NO:12; SEQ ID NO:15; SEQ ID NO:19; SEQ ID NO:20; SEQ ID NO:26; SEQ ID NO:29; SEQ ID NO:40; SEQ ID NO:46; SEQ ID NO:47; SEQ ID NO:51; SEQ ID NO:62; SEQ ID NO:69; SEQ ID NO:74; SEQ ID NO:76; SEQ ID NO:84; SEQ ID NO:88; SEQ ID NO:89; SEQ ID NO:91); SEQ ID NO:110; SEQ ID NO:111; SEQ ID NO:112; SEQ ID D NO:113; SEQ ID NO:115; SEQ ID NO:121; SEQ ID NO:122; SEQ ID NO:124; SEQ ID NO:142; SEQ ID NO:144; SEQ ID NO:152; and SEQ ID NO:157.

The multimer is optionally capped at its N- and C-termini, It is understood that such multimers may be built from any of the peptides or variants described herein. Although it is preferred that the addition variant monomeric units of the multimer have the biological activity described above, that is not necessary as long as the multimer to which they contribute has the activity.

The present invention includes as fusion polypeptide which may comprise a linear multimer of two or more repeats of the above peptide monomers linked end to end, directly or with a linker sequences present between the monomer repeats and further fused to another polypeptide sequence which permits or enhances the activity of the antigenic peptides in accordance with this invention.

The present multimers and fusion polypeptides may therefore include more than one epitope from the same or different Mtb proteins that do not occur together, i.e., in a contiguous structure, in a native Mtb protein.

Also included herein are polyproteins or fusion proteins which combine longer polypeptides, even full length Mtb proteins such as those from which the peptides are derived, as well as other early antigens such as GlcB, MPT51 and other Mtb early antigens described herein in various combinations, such as a fusion of GlcB and MPT51 or these two with another one or more early antigenic protein. These full length proteins may be combined in polyproteins with shorter epitope-bearing Mtb peptides or variants thereof or with peptide multimers (homo- or hetero-multimers. Such fusion proteins optionally includes spacers or linkers between some or all of the individual protein or peptide units.

Peptides and multimers may be chemically conjugated to form multimers and larger aggregates. Preferred conjugated multimers include Cys and are made by forming disulfide bonds between the —SH groups of these residues, resulting in branched chains as well as straight chain peptides or polypeptides.

In addition to the linkers described above, the present multimers and fusion polypeptides may include linkers that are cleavable by an enzyme. Preferred enzymes are matrix metalloproteases, urokinases, cathepsins, plasmin or thrombin. One preferred linker is the peptide VPRGSD (SEQ ID NO:173) or DDKDWH (SEQ ID NO:174).

These peptides may be combined in the form of fusion polypeptides that comprise one or more repeats of a single peptide or mixtures of such peptides fused to other proteins, e.g., carrier molecules or other proteins which would enhance their immunogenicity when used as vaccine compositions.

Additional compositions within the scope of this invention are the foregoing peptides, multimers or fusion polypeptides immobilized to a solid support or carrier for use in immunoassays. By "solid phase support" is intended any support capable of binding antigen or antibodies. Well-known supports, or carriers, include glass, polystyrene, polypropylene, polyethylene, dextran, nylon, amylases, natural and modified celluloses, polyacrylamides, polyvinylidene difluoride, agaroses such as Sepharose®, and magnetic beads. The support material may have virtually any possible structural configuration so long as the immobilized peptide or polypeptide is capable of binding to its target molecule, e.g., antibody. Thus, the support configuration can include microparticles, beads, porous and impermeable strips and membranes, the interior surface of a reaction vessel such as a test tube or a microtiter plate, the external surface of a rod, and the like. Those skilled in the art will know many other suitable carriers for binding the peptides or will be able to ascertain these by routine experimentation.

The kits of the present invention described in more detail below may include one or more of the various peptide compositions described herein.

Immunoassays

In a preferred embodiment, the mycobacterial antigen composition is brought in contact with, and allowed to bind to, a solid support or carrier, such as nitrocellulose or polystyrene, allowing the antigen composition to adsorb and become immobilized to the solid support. This immobilized antigen is then allowed to interact with the biological fluid sample which is being tested for the presence of anti-Mtb antibodies, such that any antibodies in the sample will bind to the immobilized antigen. The support to which the antibody is now bound may then be washed with suitable buffers after which a detectably labeled binding partner for the antibody is introduced. The binding partner binds to the immobilized antibody. Detection of the label is a measure of the immobilized antibody.

A preferred binding partner for this assay is an anti-immunoglobulin antibody ("second antibody") produced in a different species. Thus to detect a human antibody, a detectably labeled goat anti-human immunoglobulin "second" antibody may be used. The solid phase support may then be washed with the buffer a second time to remove unbound antibody. The amount of bound label on the solid support may then be detected by conventional means appropriate to the type of label used (see below).

Such a "second antibody" may be specific for epitopes characteristic of a particular human immunoglobulin isotype, for example IgM, $IgG_1$, $IgG_{2a}$, IgA and the like, thus permitting identification of the isotype or isotypes of antibodies in the sample which are specific for the mycobacterial antigen. Alternatively, the second antibody may be specific for an idiotype of the ant-Mtb antibody of the sample.

As alternative binding partners for detection of the sample antibody, other known binding partners for human immunoglobulins may be used. Examples are the staphylococcal immunoglobulin binding proteins, the best know of which is protein A. Also intended is staphylococcal protein G, or a recombinant fusion protein between protein A and protein G. Protein G (of group G and group C streptococci) binds to the Fc portion of Ig molecules as well as to IgG Fab fragment at the $V_H3$ domain. Protein C of *Peptococcus magnus* binds to the Fab region of the immunoglobulin molecule. Any other microbial immunoglobulin binding proteins, for example from Streptococci, are also intended (for example, Langone, J. J., *Adv. Immunol.* 32:157, 1982.

In another embodiment of this invention, a biological fluid suspected of containing antibodies specific for a Mtb antigen may be brought into contact with a solid support or carrier which is capable of immobilizing soluble proteins. The support may then be washed with suitable buffers followed by treatment with a mycobacterial antigen reagent, which may be detectably labeled. Bound antigen is then measured by measuring the immobilized detectable label. If the mycobacterial antigen reagent is not directly detectably labeled, a second reagent comprising a detectably labeled binding partner for the Mtb antigen, generally a second anti-Mtb antibody such as a murine mAb, is allowed to bind to any immobilized antigen. The solid phase support may then be washed with buffer a second time to remove unbound antibody. The amount of bound label on said solid support may then be detected by conventional means.

By "solid phase support" is intended any support capable of binding a proteinaceous antigen or antibody molecules or other binding partners according to the present invention. Well-known supports, or carriers, include glass, polystyrene, polypropylene, polyethylene, polyvinylidene difluoride, dextran, nylon, magnetic beads, amylases, natural and modified celluloses, polyacrylamides, agaroses, and magnetite. The nature of the carrier can be either soluble to some extent or insoluble for the purposes of the present invention. The support material may have virtually any possible structural configuration so long as it is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads, 96-well polystyrene microplates and test strips, all well-known in the art. Those skilled in the art will know many other suitable carriers for binding antibody or antigen, or will be able to ascertain the same by use of routine experimentation.

Using any of the assays described herein, those skilled in the art will be able to determine operative and optimal assay conditions for each determination by employing routine experimentation. Furthermore, other steps as washing, stirring, shaking, filtering and the like may be added to the assays as is customary or necessary for the particular situation.

A preferred type of immunoassay to detect an antibody specific for a mycobacterial antigen according to the present invention is an enzyme-linked immunosorbent assay (ELISA) or more generically termed an enzyme immunoassay (EIA). In such assays, a detectable label bound to either an antibody-binding or antigen-binding reagent is an enzyme. When exposed to its substrate, this enzyme will react in such a manner as to produce a chemical moiety which can be detected, for example, by spectrophotometric, fluorometric or visual means. Enzymes which can be used to detectably label the reagents useful in the present invention include, but are not limited to, horseradish peroxidase, alkaline phosphatase, glucose oxidase, β-galactosidase, ribonuclease, urease, catalase, malate dehydrogenase, staphylococcal nuclease, asparaginase, Δ-5-steroid isomerase, yeast alcohol dehydrogenase, α-glycerophosphate dehydrogenase, triose phosphate isomerase, glucose-6-phosphate dehydrogenase, glucoamylase and acetylcholinesterase. For descriptions of EIA procedures, see Voller, A. et al., *J. Clin. Pathol.* 31:507-20 (1978); Butler, J. E., *Meth. Enzymol.* 73:482-523 (1981); Maggio, E. (ed.), *Enzyme Immunoassay*, CRC Press, Boca Raton, 1980; Butler, J E, In: *Structure of Antigens*, Vol. 1 (Van Regenmortel, M., CRC Press, Boca Raton, 1992, pp. 209-59; Butler, J. E., In: van Oss, C J et al., (eds), *Immunochemistry*, Marcel Dekker, Inc., New York, 1994, pp. 759-803; Butler, J. E. (ed.), *Immunochemistry of Solid-Phase Immunoassay*, CRC Press, Boca Raton, 1991).

In another embodiment, the detectable label may be a radiolabel, and the assay termed a radioimmunoassay (RIA), as is well known in the art. See, for example, Yalow, R. et al., Nature 184:1648 (1959); Work, T. S., et al., *Laboratory Techniques and Biochemistry in Molecular Biology*, North Holland Publishing Company, NY, 1978, incorporated by reference herein. The radioisotope can be detected by a gamma counter, a scintillation counter or by autoradiography. Isotopes which are particularly useful for the purpose of the present invention are $^{125}I$, $^{131}I$, $^{35}S$, $^{3}H$ and $^{14}C$.

It is also possible to label the antigen or antibody reagents with a fluorophore. When the fluorescently labeled antibody is exposed to light of the proper wave length, its presence can then be detected due to fluorescence of the fluorophore. Among the most commonly used fluorophores are fluorescein isothiocyanate, rhodamine, phycoerythrin, phycocyanin, allophycocyanin, o-phthaldehyde, fluorescamine or fluorescence-emitting metals such as $^{152}Eu$ or other lanthanides. These metals are attached to antibodies using metal chelators.

The antigen or antibody reagents useful in the present invention also can be detectably labeled by coupling to a chemiluminescent compound. The presence of a chemiluminescent-tagged antibody or antigen is then determined by detecting the luminescence that arises during the course of a chemical reaction. Examples of useful chemiluminescent labeling compounds are luminol, isoluminol, theromatic acridinium ester, imidazole, acridinium salt and oxalate ester. Likewise, a bioluminescent compound such as a bioluminescent protein may be used to label the antigen or antibody reagent useful in the present invention. Binding is measured by detecting the luminescence. Useful bioluminescent compounds include luciferin, luciferase and aequorin.

Detection of the detectably labeled reagent according to the present invention may be accomplished by a scintillation counter, for example, if the detectable label is a radioactive gamma emitter, or by a fluorometer, for example, if the label is a fluorophore. In the case of an enzyme label, the detection is accomplished by colorimetry to measure the colored product produced by conversion of a chromogenic substrate by the enzyme. Detection may also be accomplished by visual comparison of the colored product of the enzymatic reaction in comparison with appropriate standards or controls.

In addition to detection of antibodies, the present invention provides methods to detect and enumerate cells secreting an antibody specific for a mycobacterial antigen. Thus, for example, any of a number of plaque or spot assays may be used wherein a sample containing lymphocytes, such as peripheral blood lymphocytes, is mixed with a reagent containing the antigen of interest. As the antibody secreting cells of the sample secrete their antibodies, the antibodies react with the antigen, and the reaction is visualized in such a way that the number of antibody secreting cells (or plaque forming cells) may be determined. The antigen may be coupled to indicator particles, such as erythrocytes, preferably sheep erythrocytes, arranged in a layer. As antibodies are secreted from a single cell, they attach to the surrounding antigen-bearing erythrocytes. By adding complement components, lysis of the erythrocytes to which the antibodies have attached is achieved, resulting in a "hole" or "plaque" in the erythrocyte layer. Each plaque corresponds to a single antibody-secreting cell. In a different embodiment, the sample containing antibody-secreting cells is added to a surface coated with an antigen-bearing reagent, for example, a mycobacterial antigen alone or conjugated to bovine serum albumin, attached to polystyrene. After the cells are allowed to secrete the antibody which binds to the immobilized antigen, the cells are gently washed away. The presence of a colored "spot" of bound antibody, surrounding the site where the cell had been, can be revealed using modified EIA or other staining methods well-known in the art. (See, for example, Sedgwick, J D et al., *J. Immunol. Meth.* 57:301-9 (1983); Czerkinsky, C C et al., *J. Immunol. Meth.* 65:109-21 (1983); Logtenberg, T. et al., *Immunol. Lett.* 9:343-7 (1985); Walker, A. G. et al., *J. Immunol. Meth.* 104:281-3 (1987).

The present invention is also directed to a kit or reagent system useful for practicing the methods described herein. Such a kit will contain a reagent combination comprising the essential elements required to conduct an assay according to the disclosed methods. The reagent system is presented in a commercially packaged form, as a composition or admixture (where the compatibility of the reagents allow), in a test device configuration, or more typically as a test kit. A test kit is a packaged combination of one or more containers, devices, or the like holding the necessary reagents, and usually including written instructions for the performance of assays. The kit may include containers to hold the materials during storage, use or both. The kit of the present invention may include any configurations and compositions for performing the various assay formats described herein.

For example, a kit for determining the presence of anti-Mtb early antibodies may contain one or more early Mtb antigens, either in immobilizable form or already immobilized to a solid support, and a detectably labeled binding partner capable of recognizing the sample anti-Mtb early antibody to be detected, for example. a labeled anti-human Ig or anti-human Fab antibody. A kit for determining the presence of an early Mtb antigen may contain an immobilizable or immobilized "capture" antibody which reacts with one epitope of an early Mtb antigen, and a detectably labeled second ("detection") antibody which reacts with a different epitope of the Mtb antigen than that recognized by the (capture) antibody. Any conventional tag or detectable label may be part of the kit, such as a radioisotope, an enzyme, a chromophore or a fluorophore. The kit may also contain a reagent capable of precipitating immune complexes.

A kit according to the present invention can additionally include ancillary chemicals such as the buffers and components of the solution in which binding of antigen and antibody takes place.

The present invention provides an immunoassay for detecting the presence of an Mtb early antigen in a body fluid or in a bacterial culture grown from a body fluid of a subject suspected of being infected with Mtb. A sensitive immunoassay, such as a direct sandwich EIA or a competitive EIA can detect an Mtb protein (early antigen) in picogram amounts. A competitive assay allows detection of specific epitopes of the Mtb antigen without the necessity of starting with a purified antigen preparation. Such assays permits detection of Mtb in the patient sample at an earlier time than standard bacteriological analysis (i.e., appearance of colonies on agar). This method therefore provides a basis for clinical decisions to initiate therapy after several hours or days if the antigen can be detected in a body fluid. In any case, this is a major advantage over the conventional two to four (or more) weeks commonly needed to grow out Mtb organisms from a patient sample. The earlier the stage of the infection, the lower would be the titer of Mtb in a given body fluid, and the greater would be the advantage of the present assay over conventional diagnosis. A number of immunoassays for various Mtb antigens are known in the art and can be exploited here directly or as the basis for development of assays to detect early Mtb antigens (Wilkins et al., supra; Verbon, 1994, supra; Benjamin, R G et al., 1984, *J. Med. Micro.* 18:309-318; Yanez, M A et al., 1986, *J. Clin. Microbiol.* 23:822-825; Ma et al., supra; Daniel et al., 1986, 1987, supra; Watt, G et al., 1988, *J. Infec. Dis.* 158:681-686; Wadee, A A et al., 1990, *J. Clin. Microbiol.* 23:2786-2791). For an example of a competition EIA for Mtb antigens, see Jackett et al., supra).

In a preferred sandwich immunoassay, a human antisera (or pool) or a mAb, preferably murine, serving as the capture antibody, is immobilized to a solid phase, preferably a microplate. The test antigen preparation, for example an Mtb culture supernatant or extract is added to the immobilized antibody. After appropriate washing, a second "detection" antibody, such as a murine mAb specific for the same antigen or preferably for a different epitope of the same protein, allowed to bind in the presence of a fixed amount of a mAb, preferably of murine origin, specific for the epitope of interest. The detection mAb may be enzyme-conjugated. Alternatively, a second step reagent such as an enzyme-labeled antibody specific for murine immunoglobulin may be used for detection of antigen which has become immobilized.

The present invention permits isolation of an Mtb early antigen which is then used to produce one or more epitope-specific mAbs, preferably in mice. Screening of these putative early Mtb-specific mAbs is done using known patient sera which have been characterized for their reactivity with the early antigen of interest. The murine mAbs produced in this way are then employed in a highly sensitive epitope-specific competition immunoassay for early detection of TB. Thus, a patient sample is tested for the presence of antibody specific for an early epitope of Mtb by its ability to compete with a known mAb for binding to a purified early antigen. For such an assay, the mycobacterial preparation may be less than pure because, under the competitive assay conditions, the mAb provides the requisite specificity for detection of patient antibodies to the epitope of choice (for which the mAb is specific).

In addition to the detection of early Mtb antigens or early antibodies, the present invention provides a method to detect immune complexes containing early Mtb antigens in a subject using an EIA as described above. Circulating immune complexes have been suggested to be of diagnostic value in TB. (See, for example, Mehta, P K et al, 1989, *Med. Microbiol. Immunol.* 178:229-233; Radhakrishnan, V V et al., 1992, *J. Med. Microbiol.* 36:128-31). Methods for detection of immune complexes are well-known in the art. Complexes may be dissociated under acid conditions and the resultant antigens and antibodies detected by immunoassay. See, for example, Bollinger, R C et al, 1992, *J. Infec. Dis.* 165:913-16. Immune complexes may be precipitated for direct analysis or for dissociation using known methods such as polyethylene glycol precipitation.

Purified Mtb early antigens as described herein are preferably produced using recombinant methods. Conventional bacterial expression systems utilize Gram negative bacteria such as *E. coli* or *Salmonella* species. However, it is believed that such systems are not ideally suited for production of Mtb antigens (Burlein, J E, In: *Tuberculosis: Pathogenesis, Protection and Control*, B. Bloom, ed., Amer. Soc. Microbiol, Washington, D.C., 1994, pp. 239-252). Rather, it is preferred to utilize homologous mycobacterial hosts for recombinant production of early Mtb antigenic proteins or glycoproteins. Methods for such manipulation and gene expression are provided in Burlein, supra. Expression in mycobacterial hosts, in particular *M. bovis* (strain BCG) or *M. smegmatis* are well-known in the art. Two examples, one of mycobacterial genes (Rouse, D A et al., 1996, *Mol. Microbiol.* 22:583-592) and the other of non mycobacterial genes, such as HIV-1 genes (Winter, N et al., 1992, *Vaccines* 92, Cold Spring Harbor Press, pp. 373-378) expressed in mycobacterial hosts are cited herein as an example of the state of the art. The foregoing three references are hereby incorporated by reference in their entirety.

Urine-Based Antibody Assay

The present invention also provides a urine based diagnostic method for TB that can be used either as a stand-alone test, or as an adjunct to the serodiagnostic methods described herein. Such a method enables the practitioner to (1) determine the presence of anti-mycobacterial antibodies in urine from TB patients with early disease (non-cavitary, smear negative TB patients) and from HIV-infected TB patients; (2) determine the profile of specific mycobacterial antigens, such as those in the culture filtrate, that are consistently and strongly reactive with the urine antibodies; and (3) obtain the antigens that are recognized by the urine antibodies.

Smear positive (=late) cases constitute only about 50% of the TB cases, and patients with relatively early disease are generally defined as being smear negative. Moreover, as the HIV-epidemic spreads in developing countries, the numbers and proportions of HIV-infected TB patients increases.

Serum and urine samples from non-cavitary and/or smear negative, culture positive TB patients and from HIV-infected TB patients are obtained Cohorts comprising PPD-positive and PPD-negative healthy individuals, non-tuberculous HIV-infected individuals, or close contacts of TB patients can serve as negative controls.

The following description is of a preferred assay method and approach, and is not intended to be limiting to the particular steps (or their sequence), conditions, reagents and amounts of materials.

The reactivity of the urine samples with the various antigens is determined initially with undiluted urine samples as described above. For the urine ELISA, results obtained by the present inventors showed that the optimal concentration of the Mtb antigens (when using culture filtrate protein was 125 μl/well of 4 μg/ml suspension. This can be varied routinely depending on the antigen source (e.g., purified peptides, fusions, etc.). Also, the urine is left overnight in the antigen coated wells. However, if urine antibody titers of smear-negative and HIV-infected patients are lower than those observed in smear positive patients, it may be helpful or necessary to first concentrate the urine samples, e.g., using Amicon concentrators with a molecular weight cut off of 30 kDa. Concentrated urine samples are evaluated for the presence of antibodies to the antigens of the invention. Optimal conditions for these assays are readily as are the sensitivity and specificity of antibody detection by use of one or more of the present antigens, with the biological samples containing the antibodies.

The urine antibodies are directed against the same antigens that are recognized by the serum antibodies, although, the urine antibody titers have generally been found to be lower. A 2D map of the culture filtrate proteins was prepared on which several proteins have been identified on the basis of their reactivity with different anti-mycobacterial monoclonal antibodies, or by peptide sequencing (as described herein; see also Sonnenberg, M. G. et al., 1997, *Infec Immun* 65:4515-24)

Antigens, preferably the present peptides in the various forms that they are produced (see above) that are strongly recognized by the urine antibodies, as well as by serum antibodies, are candidates for inclusion in the preferred diagnostic assay and for testing and use in vaccines.

The nucleotide sequence of the gene (i.e., open reading frame or ORF) encoding that protein then becomes the basis for PCR amplification of the relevant DNA from genomic DNA, followed by cloning into an expression vector. See Examples.

Briefly, for cloning of the specific gene into the expression vector, PCR amplification of the target gene using primers that contain restriction sites to generate in-frame fusions is performed. The PCR product is purified, and digested with the appropriate restriction enzymes and purified again. The vector DNA is cut with the appropriate restriction enzymes and purified. The PCR product and the vector are ligated, electroporated into DH5α, and grown in the presence of hygromycin overnight. Several antibiotic-resistant colonies are grown in a small volume of medium, and the plasmid DNA isolated by miniprep. The size of the insert is checked in these colonies. Inserts from one or more colonies are sequenced.

For electroporation into *M. smegmatis*, the bacteria are grown shaking in 7H9 medium till they reach an absorbance of 0.8-1.0. The bacteria are harvested, washed twice with ice cold water, once with ice-cold 10% glycerol and suspended in the same. An aliquot of the cells are electroporated with the plasmid DNA from the colony whose insert was sequenced. The electroporated cells are grown for 3-4 hrs in 7H9, and plated on antibiotic containing plates. Several resistant colonies are grown in minimal media for 48-72 hrs. The *M. smegmatis* cell pellets are sonicated, the lysates fractionated by SDS-PAGE and the presence of the immunoreactive protein confirmed by reactivity with the antibody-containing urine samples. Colonies which express the desired protein are expanded, and the His-tagged recombinant protein is purified using of commercially available Nickel-agarose columns (Qiagen).

The reactivity of the recombinant protein with the entire cohort of urine samples is evaluated by ELISA as described herein. Combinations of antigens, preferably of individual epitopes, that provide the best sensitivity and specificity are delineated.

To summarize, a combination of the antigens or individual epitopes already defined by serological studies, and new antigens/epitopes identified and produced using methods known in the art, form the basis of a sensitive early diagnostic test for TB. If the sensitivity of antibody detection in urine samples is adequate, blood is no longer needed. If not, the combined serum+urine test provides a very sensitive diagnostic test. Use of the correct, well defined antigens on inexpensive formats (dip stick or flow through cassettes) provide a basis for an inexpensive, rapid diagnostic test for TB.

Vaccine/Immunogen Compositions

The foregoing disclosure and the Examples below prove that human subjects infected with Mtb indeed do make antibodies to the early antigens of this invention. Thus the antigens are available to the immune system and are immunogenic. Hence, the vaccine compositions (referred to also as immunogenic compositions) and methods are designed to augment this immunity, and preferably, to induce it a stage wherein the bacterial infection can be prevented or curtailed.

The vaccine compositions are particularly useful in preventing Mtb infection in subjects at high risk for such an infection, as discussed above. The vaccine compositions and methods are also applicable to veterinary uses using species of mycobacteria that infect animals.

Thus, this invention includes a vaccine composition for immunizing a subject against Mtb infection. An Mtb early antigen preferably one of the proteins, or compositions comprising the immunoreactive peptides described herein, is prepared as the active ingredient in a vaccine composition. The vaccine may also comprises one or more of the proteins described herein, peptides thereof or functional derivatives as described, or DNA encoding the protein, and a pharmaceutically acceptable vehicle or carrier.

Preferred peptides for use in a vaccine composition, alone, in combination, or in linear multimers, include the 32 peptides described herein in the context of diagnostic compositions. In one embodiment, the vaccine comprises a fusion protein or peptide multimer which includes an Mtb early antigen, e.g., a full length protein and/or one or more of the above peptides, as described above.

The vaccine composition may further comprise an adjuvant or other immune stimulating agent. For use in vaccines, the Mtb early antigen protein or epitope-bearing peptide thereof is preferably produced recombinantly, preferably in prokaryotic cells.

Full length proteins or longer, epitope-bearing fragments of the Mtb early antigen proteins, are preferred immunogens, in particular, those reactive with early antibodies. If a shorter epitope-bearing fragment, for example containing 20 amino acids or less, is the active ingredient of the vaccine, it is advantageous to couple the peptide to an immunogenic carrier to enhance its immunogenicity. Such coupling techniques are well known in the art, and include standard chemical coupling techniques using linker moieties such as those available from Pierce Chemical Company, Rockford, Ill. Suitable carriers are proteins such as keyhole limpet hemocyanin (KLH), *E. coli* pilin protein k99, BSA, or rotavirus VP6 protein.

Another vaccine embodiment is a peptide multimer or fusion protein which comprise the Mtb early antigen protein or an epitope-bearing peptide region fused linearly to an additional amino acid sequence. Because of the ease with which recombinant materials can be manipulated, multiple copies a selected epitope-bearing region may be included in a single fusion protein molecule. Alternatively, several different epitope-bearing regions can be "mixed and matched" in a single multimer or fusion protein.

The active ingredient such, preferably a recombinant product, is preferably administered as a protein or peptide vaccine. In another embodiment, the vaccine is in the form of a strain of bacteria (preferably a known "vaccine strain") which has been genetically transformed to express the protein or epitope-bearing peptide. Some known vaccine strains of *Salmonella* are described below. *Salmonella dublin* live vaccine strain SL5928 aroA148 fliC(i)::Tn10 and *S. typhimurium* LB5000 hsdSB121 leu-3121 (Newton S M et al., 1989, *Science* 244:70-2).

A *Salmonella* strain expressing an Mtb peptide or polypeptide of this invention may be constructed using known methods. Thus, a plasmid encoding the protein or peptide. The plasmid may first be selected in an appropriate host, e.g., *E. coli* strain MC1061. The purified plasmid is then introduced into *S. typhimurium* strain LB5000 so that the plasmid DNA is be properly modified for introduction into *Salmonella* vaccine strains. Plasmid DNA isolated from LB5000 is introduced into, e.g., *S. dublin* strain SL5928 by electroporation.

Expression of the Mtb protein or fragment encoded by the plasmid in SL5928 can be verified by Western blots of bacterial lysates and antibodies specific for the relevant antigen or epitope.

The active ingredient, or mixture of active ingredients, in protein or peptide vaccine composition is formulated conventionally using methods well-known for formulation of such vaccines. The active ingredient is generally dissolved or suspended in an acceptable carrier such as phosphate buffered saline. Vaccine compositions may include an immunostimulant or adjuvant such as complete or incomplete Freund's adjuvant, aluminum hydroxide, liposomes, beads such as latex or gold beads, ISCOMs, and the like. For example, 0.5 ml of Freund's complete adjuvant or a synthetic adjuvant with less undesirable side effects is used for intramuscular or subcutaneous injections, preferably for all initial immunizations; this can be followed with Freund's incomplete adjuvant for booster injections. General methods to prepare vaccines are described in *Remington's Pharmaceutical Science*; Mack Publishing Company Easton, Pa. (latest edition).

Liposomes are pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature. Adjuvants, including liposomes, are discussed in the following references, incorporated herein by reference: Singh, M, *Vaccine Adjuvants and Delivery Systems*, $1^{st}$ ed., Wiley-Interscience (2007); Gregoriades, G. et al., *Immunological Adjuvants and Vaccines*, Springer, 1990; Michalek, S. M. et al., *Curr. Top. Microbiol. Immunol.* 146:51-8 (1989).

The vaccine compositions preferably contain (1) an effective amount of the active ingredient, that is, the protein or peptide together with (2) a suitable amount of a carrier molecule or, optionally a carrier vehicle, and, if desired, (3) preservatives, buffers, and the like. Descriptions of vaccine formulations are found in Voller, A. et al., *New Trends and Developments in Vaccines*, University Park Press, Baltimore, Md. (1978).

As with all immunogenic compositions for eliciting antibodies, the immunogenically effective amounts of the proteins or peptides of the invention must be determined empirically. Factors to be considered include the immunogenicity of the native peptide, whether or not the peptide will be complexed with or covalently attached to an adjuvant or carrier protein or other carrier and the route of administration for the composition, i.e., intravenous, intramuscular, subcutaneous, etc., and the number of immunizing doses to be administered. Such factors are known in the vaccine art, and it is well within the skill of immunologists to make such determinations without undue experimentation.

The vaccines are administered as is generally understood in the art. Ordinarily, systemic administration is by injection; however, other effective means of administration are known. With suitable formulation, peptide vaccines may be administered across the mucus membrane using penetrants such as bile salts or fusidic acids in combination, usually, with a surfactant. Transcutaneous administration of peptides is also known. Oral formulations can also be used. Dosage levels depend on the mode of administration, the nature of the subject, and the nature of carrier/adjuvant formulation. Preferably, an effective amount of the protein or peptide is between about 0.01 µg/kg-1 mg/kg body weight. Subjects may be immunized systemically by injection or orally by feeding, e.g., in the case of vaccine strains of bacteria, $10^8$-$10^{10}$ bacteria on one or multiple occasions. In general, multiple administrations of the vaccine in a standard immunization protocol are used, as is standard in the art. For example, the vaccines can be administered at approximately two to six week intervals, preferably monthly, for a period of from one to four inoculations in order to provide protection.

Vaccination with the vaccine composition will result in an immune response, either or both of an antibody response and a cell-mediated response, which will block one or more steps in the Mtb bacterium's infective cycle, preferably the steps of binding to and entry into host cells in which it grows.

Having now generally described the invention, the same will be more readily understood through reference to the following examples which are provided by way of illustration, and are not intended to be limiting of the present invention, unless specified.

EXAMPLE I

Materials and Methods

Bacterial Strains and Growth Conditions:

Stock cultures of Mtb H37Rv, *M. bovis*, *M. bovis* BCG, *M. africanum*, *M. microti*, *M. avium*, *M. kansasii*, *M. scrofulaceum*, *M. intracellulare*, *M. fortuitum*, *M. smegmatis mc²*, *M. vaccae*, *M. phlei*, *M. chelonae*, and *M. xenopii* were obtained from ATCC (American Type Culture Collection, 10801 University Boulevard, Manassas, Va. 20110) and grown in Difco Middlebrook 7H9 broth (Becton Dickinson and company, Sparks, Md.) supplemented with 0.2% glycerol, 0.05% Tween 80 and 1× Albumin dextrose saline (ADS; 0.5% bovine serum albumin, fraction V {Sigma, St. Louis, Mo.}; 0.2% dextrose; and 0.85% NaCl) at 37° C. with shaking.

Human Monocyte Derived Macrophages (MDM):

The peripheral blood mononuclear cells (PBMC) isolated from whole blood on Histopaque 1077 (Sigma) gradient were incubated in Teflon® wells for 5 days in RPMI culture medium (RPMI-1640 containing 20% human AB serum (Gemini Bioproducts Inc., Woodland, Calif.) (33). Appropriate numbers of PBMCs were added to wells of 24 well tissue culture plates to obtain ~3×10⁵ monocytes/well, and incubated for 2 h to obtain adherent cells. After removal of non-adherent cells, the MDM were incubated in RPMI-1640 containing 20% human AB serum for 7 days to stabilize the monolayer before infection with Mtb (33).

Mtb RNA Isolation:

To obtain RNA from Mtb replicating in MDM, monolayers (~3×10⁵ MDM/well) were infected with a single cell suspension of a log phase culture Mtb H37Rv at a multiplicity of infection (MOI) of 1 in medium containing 10% human AB serum for 2 h at 37° C. The infected cells were washed with warm medium and maintained for 4 days at 37° C. On day 4 post-infection, MDMs were lysed with 4M guanidinium thiocyanate, 0.5% sodium N-lauryl sarcosine, 25 mM tri-sodium citrate, 0.1 M 2-mercaptoethanol, 0.5% Tween 80, pH 7.0, and bacilli separated from lysates by centrifugation at 5000×g for 20 min at 4° C. (3). To obtain sufficient quantities of RNA, bacterial pellets from 4 wells were pooled and resuspended in TRI reagent containing polyacrylamide carrier (Molecular Research Center, Inc. Cincinnati, Ohio). Total RNA was extracted (11). RNA from log phase cultures of Mtb H37Rv grown in Middlebrook 7H9 medium and from uninfected MDM was also extracted.

RT-PCR:

Total RNA preparations were subjected to reverse transcriptase (RT) reaction to synthesize first-strand cDNA using Superscript II RNase H⁻ reverse transcriptase (Invitrogen, Carlsbad, Calif.) (8). Each RNA preparation was also subjected to RT reaction in the absence of reverse transcriptase to check for DNA contamination. Using cDNA as template, PCR was performed with ptrp specific primers (PTRP-4F 5'-TGATCGGTTTCGCCTCGCTG-3' (SEQ ID NO:160), PTRP-RT 5'-GGAATGGTGCCGCCCTGGAAT-3' (SEQ ID NO:161) and Taq DNA polymerase (Promega, Madison, Wis.). PCR products were separated on a 1% agarose gels and visualized by ethidium bromide staining.

Southern Hybridization:

To determine the presence of ptrp, genomic DNA of various mycobacterial species was isolated from mid-log phase cultures using the genomic-tip system (Qiagen Inc., Valencia, Calif.). Genomic DNA of Mtb H37Rv, Mtb H37Ra, Mtb Erdman, and 7 Mtb clinical isolates were obtained from the NIH/NIAID TB Vaccine Testing and Research Materials contract (Colorado State University, Fort Collins, Colo.). DNA from 10 additional Mtb clinical isolates was procured from Dr. Barry Kreiswirth (Public Health Research Institute, Newark, N.J.). Genomic DNA (4 µg) from various mycobacterial species were digested with Xho I and separated on a 0.8% agarose gel and the Southern blots prepared. To obtain the DIG-labeled ptrp (1645 bp) for probing the Southern blots, the gene was amplified with primers (forward; 5'-AGCCAGCCGAAGGAGAGCCCATATGGA-3') (SEQ ID NO:162) and (reverse; 5'-AGTGAAGCCGCGACCGAAGCTTGAACC-3') (SEQ ID NO:163) from Mtb H37Rv genomic DNA. The PCR product was cloned into pET23b+ vector (PTRP-pET23b+, Novagen, EMD Biosciences, San Diego, Calif.). The plasmid PTRP-pET23b+ DNA was digested with Nde I and Hind III to release ptrp which was labeled with DIG (DIG probe synthesis kit, Roche Diagnostic Corporation, IN). The hybridization and detection were performed using DIG standard hybridization buffer and chemiluminescent detection system according to the manufacturer's protocols (Roche).

To further explore the distribution of ptrp in different mycobacterial species, the complete gene (1697 bp) was amplified from the genomic DNAs using primers PTRP 1F (5'-TGCCGGGACATTGCTGGTTG-3') (SEQ ID NO:164), and PTRP 2R (5'-TGATCAGAACCCGCCGAATAAG-3') (SEQ ID NO:165). Southern blots prepared with these amplified PCR products were probed with the DIG-labeled ptrp gene fragment amplified from Mtb H37Rv genomic DNA (Roche).

Expression and Purification of Recombinant (r) PTRP:

To express rPTRP with a N-terminal GST tag, the entire Mtb ptrp open reading frame was amplified by PCR using the forward primer 5'-<u>GGATCC</u>ATGGACGTCGCTTTGGGGGTT-3' (SEQ ID NO:166) (underlined sequence is a BamHI site) and reverse primer 5'-<u>CTCGAG</u>TCAGAACCCGCCGAATCCGTC-3' (SEQ ID NO:167) (underlined sequence is a XhoI site). The 1,659 bp PCR product was isolated by gel purification and ligated into the pCR4Blunt-TOPO cloning vector (Invitrogen). This intermediate plasmid was digested with BamHI and XhoI and the resulting fragment ligated into the BamHI and XhoI sites of the glutathione S-transferase (GST) fusion vector pGEX-6P-1 (GE Healthcare, Piscataway, N.J.). The *E. coli* strain BL21 (DE3) pLysS (Invitrogen) harboring ptrp in the pGEX-6P-1 expression vector was grown in 2YT (Difco Laboratories) broth supplemented with 100 µg/ml ampicillin and 34 µg/ml chloramphenicol at 37 C for 12 hours with subsequent induction of gst-ptrp expression by addition of 0.5 mM isopropyl thio-galactoside (IPTG) overnight at 25° C. The harvested cells were resuspended in PBS (pH 7.4) containing DNAse (0.6 µg/ml) and lysed by probe sonication using a Model 4710, Cole-Parmer (Chicago, Ill.) sonicator. The resulting supernatant after centrifugation of the lysate was added to 1 ml of PBS equilibrated Glutathione Sepharose 4 Fast Flow (GE Healthcare) and incubated with gentle agitation at 4° C. for 2 h. The resin was washed once with 10 vol of PBS and once with 10 vol of PreScission Protease cleavage buffer (50 mM Tris-Cl, 10 mM NaCl, 1 mM EDTA, and 1 mM dithiothreitol, pH 7.0). The cleavage of the GST tag was performed by incubating the resin protein mixture suspended in 1 volume of cleavage buffer containing PreScission protease (100 units: GE Healthcare) at 4° C. with gentle shaking overnight (ON). The mixture was added to a column followed by an additional 10 column volumes (CV) of cold cleavage buffer. Fractions containing the non-GST tagged rPTRP protein as determined by SDS-PAGE were pooled and dialyzed against 10 mM Tris (pH 6.3). To ensure purity, the rPTRP was applied to an anion exchange resin (Q Sepharose, Amersham Biosciences). The column was washed with 10 CV of 10 mM Tris (pH 6.3) and bound proteins eluted in a step gradient with 10 CV each of 10 mM Tris (pH 6.3) containing 100, 200, 300, 400, 500 and 1000 mM NaCl. Fractions containing purified rPTRP were pooled and dialyzed against 10 mM ammonium bicarbonate. Protein concentrations were determined using the BCA method and endotoxin contamination was determined using the QCL-1000® Chromogenic LAL Endpoint Assay (Cambrex Bio Science, Walkersville, Inc., Walkersville, Md.). Protein sequencing of rPTRP was performed by Quadrupole time-of-flight (Q-TOF) mass spectrometry at NYU protein analysis facility.

Production of Anti-PTRP Polyclonal Antibodies:

Anti-PTRP antibodies were produced in a New Zealand white rabbit by immunization with purified rPTRP in incomplete Freund's adjuvant (21). IgG from pre- and post-immunization sera was purified by affinity chromatography on protein A sepharose 4B columns (Amersham Biosciences, Sweden).

Localization of PTRP:

Mtb H37Rv subcellular protein fractions (total cell-wall, SDS extracted cell-wall proteins, whole cell lysates and culture filtrate preparations) were obtained from the NIH/NIAID TB Vaccine Testing and Research Materials contract. The fractions (10 µg/lane) were separated on SDS-PA gels and the western blots probed with rabbit anti-PTRP IgG or pre-immune IgG (1:1000) followed by alkaline phosphatase (AP)-conjugated anti-rabbit IgG (1:2000) and BCIP-NBT substrate (KPL Inc, Gaithersburg, Md.). Various concentrations (2.5-10 µg/ml in PBS, pH 7.0) of the same subcellular fractions were also coated in triplicate in wells of ELISA plates by incubating for 2 h at 37° C. followed by ON at 4° C. The wells were washed with PBS, blocked with 1% BSA for 2 h at 37° C., washed with PBS containing 0.05% Tween 20 (PBST) and anti-PTRP IgG or pre-immune IgG (1:1000) added for 1.5 h at 37° C. After subsequent washing with PBST, the bound antibodies were detected with anti-rabbit-AP (1:2000) and the Amplification System (Invitrogen). To confirm the exposure of PTRP on the intact bacterial cells, wells of ELISA plates were coated in triplicate with 50 µl of serially diluted single-cell suspension of γ-irradiated Mtb H37Rv or CDC1551 cells by incubating 1 h at 37° C. and ON at 4° C. (21). Wells were washed with PBS, blocked with 1% BSA, washed again with PBST and exposed to anti-PTRP IgG or pre-immune IgG (1:1000) for 1.5 h at 37° C. The bound IgG was detected with anti-rabbit IgG-AP (1:4000) and substrate.

Serum Specimens:

Serum specimens were obtained with informed consent from 13 PPD$^-$ and 23 PPD$^+$ healthy subjects working in the Manhattan Veterans Affairs Medical Center (VAMC), New York. Of these, 9 PPD$^-$ and 16 PPD$^+$ subjects were recent immigrants from TB-endemic countries (India, China, Cameroon). Sera were also obtained from 60 HIV$^-$TB$^+$ patients from Lala Ram Sarup Institute of Tuberculosis and Respiratory Diseases, New Delhi, India) and 6 HIV+TB$^+$ patients from Post Graduate Institute of Medical Education and Research, Chandigarh, India. These patients were diagnosed on the basis of AFB positive sputum smears and were bled prior to initiation of therapy. Sera from 6 asymptomatic HIV+ patients with no clinical symptoms of TB (HIV+TB−) were procured from VAMC. These patients were being treated with anti-retroviral drugs and their PPD status was not known.

Detection of Anti-PTRP Antibodies in Sera from TB Patients:

Western blots of purified rPTRP (40 ng/lane) were blocked with 3% BSA, washed with PBST and probed with sera from HIV$^-$TB$^+$ patients or PPD$^+$ healthy controls (1:50) ON at 4° C. Similar blots were also probed with sera from HIV+TB$^+$ patients, and HIV+TB−, PPD$^-$ and PPD$^+$ subjects (1:100). The anti-PTRP antibodies in the human sera were detected by a mixture of protein-A-AP (1:2000, Sigma) and anti-human IgA-AP (1:1000, Sigma) and BCIP-NBT substrate (KPL).

Mapping of Immunodominant Regions of PTRP:

Fifty-four overlapping peptides (20 a.a. length with 10 a.a. overlap) covering the entire PTRP sequence were synthesized commercially in PEPscreen format (Sigma Genosys). Each peptide was linked with a biotin residue at the N-terminus. To identify immunodominant epitopes, reactivity of each peptide was tested by ELISA with sera from 60 HIV$^-$TB$^+$ patients and 36 PPD$^-$ and PPD$^+$ healthy subjects. Fifty µl of each peptide (2.5 µg/ml) diluted in blocking buffer (7.5% fetal bovine serum (FBS; Hyclone) and 2.5% BSA in PBS) was added to wells of streptavidin-coated ELISA plates (Roche) and incubated for 1 h at 37° C. Subsequently, 50 µl of diluted sera (1:20 in 0.1× blocking buffer) from patients and healthy subjects were added and incubated for 1 h at 37° C. After four washes with PBST, a mixture of protein-A-AP (1:2000, Sigma) and anti-human IgA-AP (1:1000, Sigma) was added to each well and incubated for 1 h at 37° C. The wells were washed six times with PBST and the bound enzyme-conjugated antibodies detected with p-nitrophenyl phosphate (pNPP) substrate (1 mg/ml pNPP in 1 M diethanolamine buffer containing 0.5 mM MgCl$_2$, pH 9.8). Plates were read at 405 nm. The cut-off was determined by calculating mean OD obtained with sera from PPD$^+$ and PPD$^-$ individuals plus 3 standard deviations (SD). All peptides were screened once; peptides that were recognized by antibodies in sera from at least 40% of the 60 HIV$^-$TB$^+$ patients were tested for reactivity with the same serum panel on 2 additional separate occasions. Sera showing positive reactivity 2/3 or 3/3 times were considered positive.

Binding of PTRP to ECM Proteins:

The binding of the purified rPTRP to various ECM proteins was determined both by western blotting and ELISA (21). Laminin-1 (human placenta); fibronectin and fibrinogen (human plasma) and elastin (human lung) were obtained from Sigma; human collagen I; collagen III and collagen IV (human placenta), collagen II (human cartilage) and vitronectin (human plasma) from Chemicon International Inc. Temecula, Calif. Thrombospondin (human platelet) was from Calbiochem, EMD Biosciences Inc. and BSA (negative control) was from Promega. Western blots containing rPTRP (0.4 µg/lane) were blocked with 3% BSA in PBS and incubated with the ECM proteins (5 µg/ml) dissolved in PBS. Negative control lanes were incubated with PBS alone. The bound ECM proteins were detected with appropriate anti-ECM antibodies (anti-laminin, anti-fibronectin, anti-thrombospondin and anti-vitronectin at 1:5000; anti-fibrinogen at 1:1000; anti-Col I, Col III, Col IV and anti-elastin at 1:500; anti-Col II at 1:100) followed by appropriate enzyme-conjugated secondary antibodies (anti-rabbit IgG-AP at 1:2000; anti-goat IgG-AP at 1:3000).

The wells of ELISA plates were coated with various concentration of rPTRP (5-20 µg/ml in PBS) or BSA for 1 h at 37° C. followed by ON at 4° C. Subsequently, the wells were washed with PBS, blocked with 1% BSA in PBS (2 h at 37° C.), washed again with PBST and incubated with different ECM proteins (1 µg/ml; only laminin at 0.5 µg/ml) for 2 h at 37° C. After washing again, the wells were exposed to respective anti-ECM antibodies and the appropriate enzyme-conjugated secondary antibodies to detect the bound ECM proteins.

Bioinformatic Analysis:

Prediction of theoretical molecular weight and amino acid composition (ProtParam), transmembrane helices (TMpred), repetitive sequences (Statistical analyses of protein sequences, SAPS) and glycosylation sites (NetOGlyc 3.1) and secondary structure of the proteins (SOPMA) were carried out with the respective software available on ExPASy Proteomics server (www address: ca.expasy.org). Prediction of sub-cellular location of PTRP was based on ProtCompB v6.1 software on Softberry website (softberry.com) which predicts localization of proteins in gram-positive bacteria. BLAST searches with entire current databases were performed on the National Center for Biotechnology Information website (www address is ncbi.nlm.nih.gov).

Statistical Analysis:

The comparison between reactivity of PTRP peptides with sera from PPD$^-$ vs PPD$^+$ healthy controls as well as PPD$^+$/PPD$^-$ healthy controls vs TB patients were performed by calculating P value with nonparametric Mann-Whitney test using GraphPad Prism version 5 software (GraphPad Software, Inc. San Diego, Calif.). A P value of <0.05 was considered statistically significant.

EXAMPLE II

Characteristics of PTRP

The PTRP is a 548 aa (55 kDa) protein with a Pro- and Thr-rich region towards the C terminus (aa 415 to 516). Visual analysis of the C-terminal region revealed the presence of 23 tandem repeats of the motif PPTT, with the first Pro-residue being less conserved (49). SAPS identified 4 tandem repeats of motif TT/APPTTPP/VTTP/SV/A (SEQ ID NO:159) and 3 of motif TV/TA/PPTTVAPT/- (SEQ ID NO:175) from aa 413 to 489 (FIG. 1). (aa's separated by a "/" are alternates at a given position.) Softberry analysis predicts PTRP to be a membrane-bound secreted protein since it contains both a signal sequence (aa 1-25) and 4 transmembrane helices. PTRP is predicted to contain 57 O-glycosylation sites, almost all in the repetitive region (FIG. 1).

BLAST-P analysis showed the presence of homologous protein in Mtb CDC 1551; Mtb F11; Mtb C, Mtb H37Ra, *M. bovis* AF2122/97 and *M. bovis* BCG str. Pasteur 1173P2. In *M. leprae* TN, the corresponding gene is predicted to be a pseudogene. No homologous protein is present in the pathogenic non-tuberculous mycobacteria (NTM; *M. avium paratuberculosis* K 10, *M. avium* 104 and *M. ulcerans* Agy99), although hypothetical proteins that show ~50-60% homology are present in these species. By using <30% identity as a cut-off, no protein showed homology to PTRP in the entire database. These analyses suggest that PTRP is an Mtb (complex)-specific protein.

When only the repetitive region of PTRP (aa 413-489) was used to query the database, besides PTRP, multiple proteins in all the mycobacterial genomes showed ~10-60% homology, primarily with the Pro-Thr residues. Multiple proteins from a variety of other bacteria also exhibited ~35-60% homology, with the exception of a hypothetical protein in the *Bacillus thuringiensis* genome that showed ~80% homology. Besides the Cnm protein of *Streptococcus mutans* (54% identity) which is a collagen and laminin-binding adhesin (43), all other proteins showing homology were either hypothetical or predicted only.

The primary structures of PTRP and Cnm showed remarkable similarities in length, presence of a signal peptide, C-terminal location of the Pro-Thr-rich repeat motifs and glycosylation sites (FIG. 1A). Interestingly, the predicted secondary structures of PTRP and Cnm are also similar in that for both proteins the C-terminal region consists mainly of random coils and the N-terminal half of the protein (1-300 aa) contains the majority of alpha helices, extended strands and beta turns. In contrast, despite similarities in domain organization, the predicted secondary structures of HBHA and ML-LBP21 lacked the extended random coil region and the α helices are distributed throughout the length of the proteins.

EXAMPLE III

Ptrp Transcripts are Present in Mtb Replicating in MDM

Although ptrp transcripts have been reported in studies with broth-grown Mtb (15), PTRP has not been identified in any proteomic studies of Mtb subcellular fractions (2, 17, 20, 25-27, 40, 44, 50, 51, 55). When existence of ptrp transcripts in bacteria residing in MDM was investigated, the expected 193 bp fragment was amplified from cDNA prepared from total RNA of Mtb-infected MDM, but not from similar preparations from uninfected macrophages, or in the absence of reverse transcriptase (FIG. 2A). Thus, it is concluded that PTRP is expressed during intracellular residence of Mtb in human macrophages.

EXAMPLE IV

Ptrp is Mtb (Complex) Specific

Figure 3C:
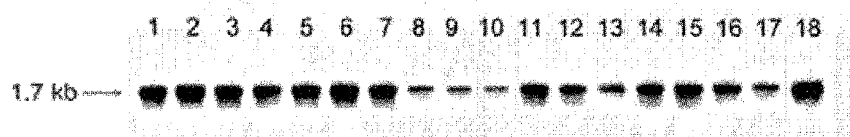
Figure 7A:
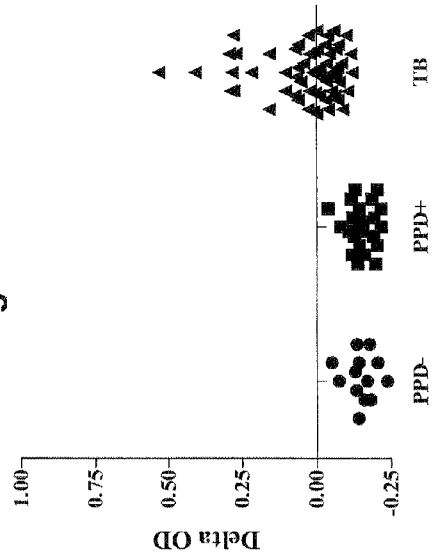
Figure 7C:
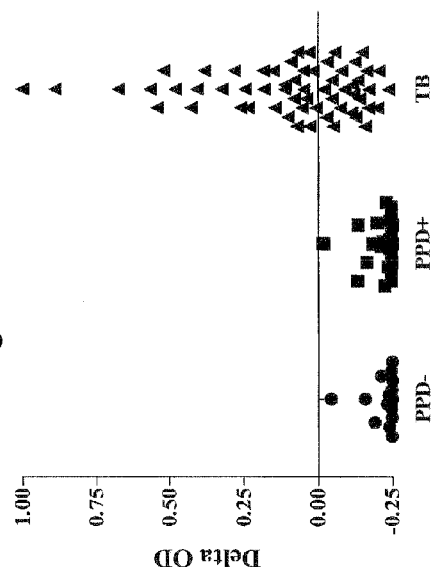
Figure 7B:
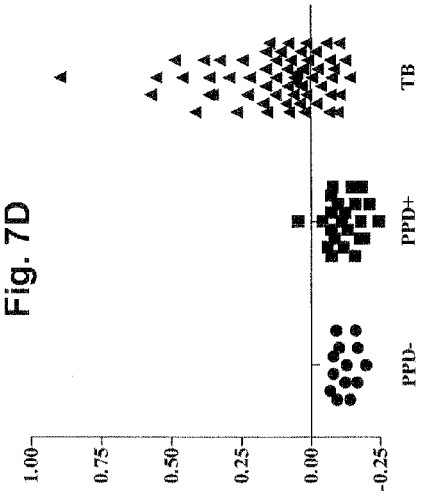
Figure 7D:
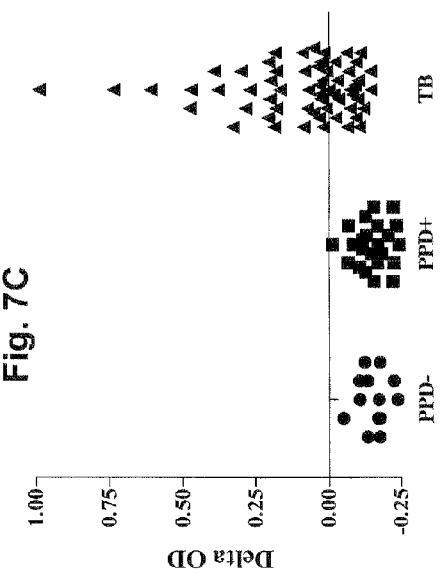

The BLAST of ptrp showed presence of homologous gene in Mtb complex species and clinical isolates but not in the NTM species sequenced so far. To gain further insight into the distribution of ptrp in various mycobacterial species, Southern hybridization with genomic DNA from several species was performed. The DIG-labeled ptrp probe hybridized with a single ~9.5 kb band in the fractionated genomic DNA from Mtb complex species but not from any of the NTM species tested (FIG. 3A). Evidence for restriction of ptrp to Mtb complex and the Mtb clinical isolates was also obtained when the ~1.7 kb ptrp was amplified only from them and not from any NTM species tested (FIGS. 3B and 3C).

EXAMPLE V

Expression and Purification of Recombinant (r)PTRP

The purified rPTRP (without GST tag) was visualized as a ~52 kD band on SDS-PA gel stained with Coomassie blue (FIG. 4A). Protein sequencing of this band by Quadrupole time-of-flight (Q-TOF) mass spectrometry confirmed its identity (data not shown). This rPTRP was used to elicit polyclonal anti-PTRP antibodies.

EXAMPLE VI

PTRP is a Cell-Wall Protein of Mtb

When anti-PTRP antibodies and the corresponding pre-immune sera were used to probe western blots prepared with Mtb subcellular fractions (total Cell-wall, SDS-extracted cell-wall proteins, whole cell-lysate and culture-filtrates), only the former identified a ~52 kD protein in the total cell-wall and the SDS-extracted cell-wall fractions. Weak reactivity with the same band was observed in the whole cell-lysate preparation, but no reactivity was observed with any protein in the culture-filtrate fraction (FIG. 4B). Anti-PTRP antibodies also showed a dose-dependent reactivity when tested with various concentrations of total cell-wall and SDS-extracted cell-wall preparations (FIG. 4C). Finally, anti-PTRP antibodies bound to intact Mtb H37Rv and Mtb CDC 1551 bacterial cells in a dose-dependent manner (FIG. 4D). Together these results demonstrate that PTRP is a cell-wall protein of Mtb.

EXAMPLE VII

PTRP is a Target of Immune Responses

Secreted and cell-wall proteins of Mtb are dominant targets of immune responses in TB patients and presence of antibodies to any protein in sera from TB patients is evidence of its expression in vivo (41). When the western blots of rPTRP was probed with sera from TB patients and healthy subjects, sera from 4/6 HIV⁻TB⁺ patients and 5/6 HIV+TB⁺ patients showed reactivity with the ~52 kDa protein that was also recognized by anti-PTRP antibodies (FIG. 5). In contrast, sera from none of the 6 PPD⁺, 6 PPD⁻ and 6 HIV+TB− showed any significant reactivity with the protein (FIG. 5). These results demonstrate that PTRP is target of immune responses during active infection with Mtb, both in HIV⁻TB⁺ and HIV+TB⁺ patients.

TABLE 1

PTRP overlapping peptides and their Immunoreactivity

| Peptide Name | Sequence | SEQ ID NO: | MW (daltons) | Immuno-reactive* |
|---|---|---|---|---|
| PT-1 | MDVALGVAVTDRVARLALVD | 7 | 2423 | ++ |
| PT-2 | DRVARLALVDSAAPGTVIDQ | 8 | 2406 | |
| PT-3 | SAAPGTVIDQFVLDVAEHPV | 9 | 2404 | ++ |
| PT-4 | FVLDVAEHPVEVLTETVVGT | 10 | 2493 | |
| PT-5 | EVLTETVVGTDRSLAGENHR | 11 | 2522 | |
| PT-6 | DRSLAGENHRLVATRLCWPD | 12 | 2649 | ++ |
| PT-7 | LVATRLCWPDQAKADELQHA | 13 | 2605 | |
| PT-8 | QAKADELQHALQDSGVHDVA | 14 | 2471 | |
| PT-9 | LQDSGVHDVAVISEAQAATA | 15 | 2321 | ++ |
| PT-10 | VISEAQAATALVGAAHAGSA | 16 | 2134 | |
| PT-11 | LVGAAHAGSAVLLVGDETAT | 17 | 2191 | |
| PT-12 | VLLVGDETATLSVVGDPDAP | 18 | 2307 | |
| PT-13 | LSVVGDPDAPPTMVAVAPVA | 19 | 2245 | ++ |
| PT-14 | PTMVAVAPVAGADATSTVDT | 20 | 2213 | ++ |
| PT-15 | GADATSTVDTLMARLGDQAL | 21 | 2345 | |
| PT-16 | LMARLGDQALAPGDVFLVGR | 22 | 2438 | |
| PT-17 | APGDVFLVGRSAEHTTVLAD | 23 | 2394 | |
| PT-18 | SAEHTTVLADQLRAASTMRV | 24 | 2496 | |
| PT-19 | QLRAASTMRVQTPDDPTFAL | 25 | 2557 | |
| PT-20 | QTPDDPTFALARGAAMAAGA | 26 | 2271 | ++ |
| PT-21 | ARGAAMAAGAATMAHPALVA | 27 | 2148 | |
| PT-22 | ATMAHPALVADATTSLPRAE | 28 | 2362 | |
| PT-23 | DATTSLPRAEAGQSGSEGEQ | 29 | 2330 | ++ |
| PT-24 | AGQSGSEGEQLAYSQASDYE | 30 | 2416 | |
| PT-25 | LAYSQASDYELLPVDEYEEH | 31 | 2710 | |
| PT-26 | LLPVDEYEEHDEYGAAADRS | 32 | 2618 | |
| PT-27 | DEYGAAADRSAPLSRRSLLI | 33 | 2500 | |
| PT-28 | APLSRRSLLIGNAVVAFAVI | 34 | 2406 | |
| PT-29 | GNAVVAFAVIGFASLAVAVA | 35 | 2186 | |
| PT-30 | GFASLAVAVAVTIRPTAASK | 36 | 2269 | |
| PT-31 | VTIRPTAASKPVEGHQNAQP | 37 | 2440 | |
| PT-32 | PVEGHQNAQPGKFMPLLPTQ | 38 | 2529 | |
| PT-33 | GKFMPLLPTQQQAPVPPPPP | 39 | 2480 | |
| PT-34 | QQAPVPPPPPDDPTAGFQGG | 40 | 2312 | ++ |
| PT-35 | DDPTAGFQGGTIPAVQNVVP | 41 | 2322 | |
| PT-36 | TIPAVQNVVPRPGTSPGVGG | 42 | 2242 | |
| PT-37 | RPGTSPGVGGTPASPAPEAP | 43 | 2142 | |
| PT-38 | TPASPAPEAPAVPGVVPAPV | 44 | 2163 | |
| PT-39 | AVPGVVPAPVPIPVPIIIPP | 45 | 2281 | |
| PT-40 | PIPVPIIIPPFPGWQPGMPT | 46 | 2494 | ++ |
| PT-41 | FPGWQPGMPTIPTAPPTTPV | 47 | 2431 | ++ |
| PT-42 | IPTAPPTTPVTTSATTPPTT | 48 | 2291 | |

TABLE 1-continued

PTRP overlapping peptides and their Immunoreactivity

| Peptide Name | Sequence | SEQ ID NO: | MW (daltons) | Immuno-reac-tive* |
|---|---|---|---|---|
| PT-43 | TTSATTPPTTPPTTPVTTPP | 49 | 2305 | |
| PT-44 | PPTTPVTTPPTTPPTTPVTT | 50 | 2343 | |
| PT-45 | TTPPTTPVTTPPTTPPTTPV | 51 | 2343 | ++ |
| PT-46 | PPTTPPTTPVTTPPTTVAPT | 52 | 2313 | |
| PT-47 | TTPPTTVAPTTVAPTTVAPT | 53 | 2263 | |
| PT-48 | TVAPTTVAPTTVAPTTVAPA | 54 | 2205 | |
| PT-49 | TVAPTTVAPATATPTTVAPQ | 55 | 2234 | |
| PT-50 | TATPTTVAPQPTQQPTQQPT | 56 | 2432 | |
| PT-51 | PTQQPTQQPTQQMPTQQQTV | 57 | 2634 | |
| PT-52 | QQMPTQQQTVAPQTVAPAPQ | 58 | 2488 | |
| PT-53 | APQTVAPAPQPPSGGRNGSG | 59 | 2185 | |
| PT-54 | PQPPSGGRNGSGGGDLFGGF | 60 | 2200 | |

* ++ indicates that the peptides were recognized by 40% or more TB patient sera. Peptides were biotinylated at the N-terminus for immobilization to a surface coated with streptavidin. All peptides were analyzed by MALDI + MS. All peptides passed MS analysis and the final gross weight criteria (>5 mg).

EXAMPLE VIII

Identification of Immunodominant Epitopes of PTRP

Considering that the PTRP is Mtb (complex) specific, is present in all clinical isolates of Mtb tested, and is recognized by antibodies in sera from TB patients, its potential for diagnosis of TB was evaluated. Fifty-four overlapping peptides representing the entire 548 aa of PTRP were synthesized commercially. The reactivity of 53 peptides (one peptide was insoluble) was tested with sera from 60 HIV$^-$TB$^+$ patients and 36 PPD$^+$/PPD$^-$ healthy controls. There was no significant difference in the reactivity of the PPD$^-$ and PPD$^+$ sera with 49 peptides (p=0.561-0.986); with remaining peptides the ODs obtained with the individual sera in PPD$^+$ group (3 peptides) or PPD$^-$ group (1 peptide) were relatively higher in comparison to respective PPD$^-$ or PPD$^+$ groups (data not shown). Using mean OD plus 3 SD of the 36 PPD$^-$ and PPD$^+$ healthy individuals as cut-off, 22 peptides showed no reactivity with sera from any of the healthy controls and remaining peptides reacted only with 1 or 2 of these sera (FIG. 6A). In contrast, 37/53 peptides were recognized by sera from 20-68% of HIV$^-$TB$^+$ patients; the remaining 16 peptides were recognized by sera from <20% HIV$^-$TB$^+$ patients (FIG. 6A).

The 16 highly immunogenic peptides that were recognized by sera from at least 40% of the 60 HIV$^-$TB$^+$ patients were retested twice with the same panel of sera to validate the results of the screening described above. A vast majority of these 16 peptides (12/16) continued to be recognized by at least 40% of the TB sera (FIG. 6B). Antibodies to at least one of the 16 peptides were detected in sera from 57/60 (95%) TB patients while 2/36 (6%) of the sera from the healthy subjects reacted with any of the 16 peptides (FIG. 6B; C1). When the additive reactivity of the 4 most immunogenic peptides, (PTRP 9 (58%), 13 (53%), 40 (52%) and 41 (55%)) was considered, sera from 82% of the HIV$^-$TB$^+$ patients and none of the control subjects were antibody positive (FIG. 6B; C2).

The reactivity of the individual sera with these 4 peptides is shown in FIG. 7A-7D. There was no difference in the OD values obtained with the PPD$^-$ and PPD$^+$ healthy subjects with any of these peptides (p=0.48-0.99). In contrast, the OD values obtained with sera from TB patients were significantly higher for all 4 peptides (p<0.0001). As is evident, had the cut-off been calculated by using the OD values from only the PPD$^-$ subjects, the sensitivity of antibody detection in TB patients would either be unaffected or be enhanced (FIG. 7A-7D).

EXAMPLE IX

PTRP binds to Extracellular Matrix (ECM) Proteins

Figure 8B:
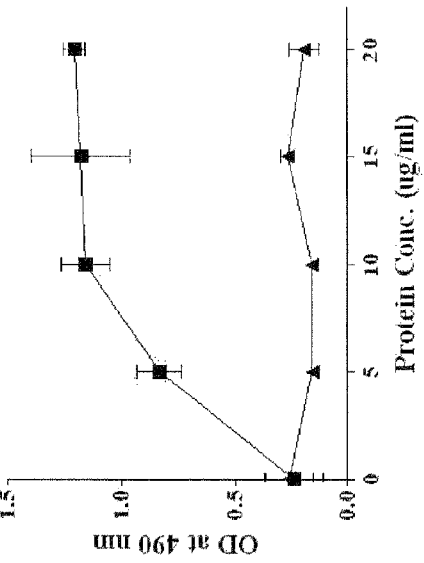
Figure 8C:
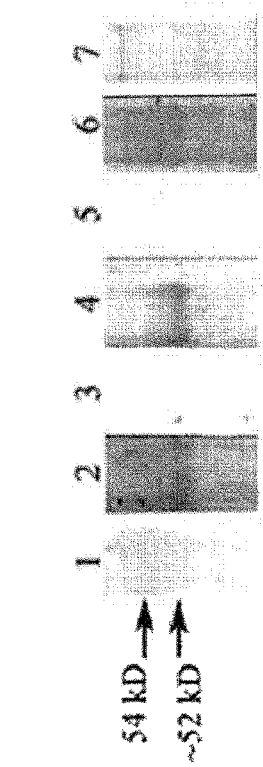
Figure 8D:
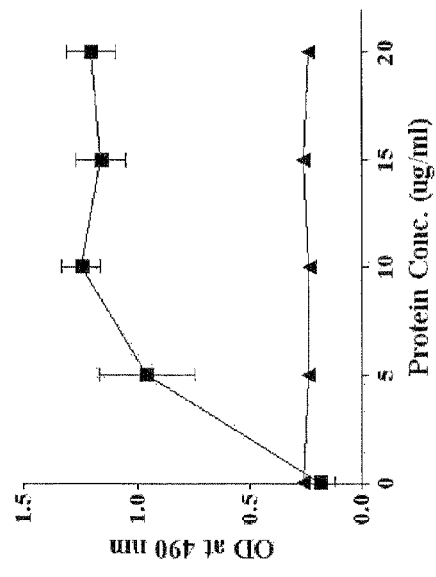

The cell-wall localization of PTRP and the similarities in the primary and/or secondary structures with other known bacterial adhesins prompted investigation into the potential function of PTRP as an adhesin of Mtb. In western blots, rPTRP showed binding with thrombospondin, laminin and fibronectin (FIG. 8A), but not with any of the other ECM proteins tested (not shown). The same results were obtained when the PTRP-ECM interaction was investigated by ELISA in that rPTRP was observed to bind to thrombospondin, laminin and fibronectin in a dose-dependent manner (FIGS. 8B, C and D).

Discussion of Examples I-IX

Many genes in the Mtb genome are annotated as hypothetical proteins. Determination of the function of these genes/proteins is challenging due to lack of information on the potential function but their restriction to Mtb enhances the likelihood of their importance in Mtb-specific virulence and pathogenesis. PTRP is one such hypothetical protein that has not been identified so far in any of the proteomic studies of Mtb culture filtrates or other subcellular fractions (2, 17, 20, 25-27, 40, 44, 50, 51, 55). In the current studies, PTRP was shown to be a bonafide cell-wall protein of Mtb. The presence of PTRP in both the Mtb total cell-wall and the SDS-extracted cell-wall protein preparations, both by western blot and ELISA, coupled to the presence of PTRP on the surface of intact bacteria, confirm its cell wall localization. This is also consistent with the probable functional category of cell-wall ascribed to PTRP in Mtb H37Rv genome (7). The presence of a signal sequence suggested that PTRP would also be present in the culture-filtrates of Mtb, however, no protein was identified by the anti-PTRP antibodies in our studies and none of the several proteomic studies of Mtb or BCG culture-filtrate proteins have reported the existence of this protein (20, 25, 26, 40, 51). This could be due to it being secreted in minimal quantities or being unstable or rapidly degraded in the culture filtrates. Also, although PTRP is predicted to have 4 transmembrane regions, it was not identified in the proteomic analysis of the membrane fraction of Mtb (17, 27, 50, 55). The presence of ptrp transcripts in intracellular as well as extracellular Mtb, and the presence of anti-PTRP antibodies in animals and humans with active Mtb infection further supports the conclusion that PTRP is an integral cell-wall protein of Mtb (49).

The Southern hybridization and PCR studies with genomic DNA from several mycobacterial species suggest that ptrp is Mtb (complex) specific. The absence of a homologue in the common human pathogens (*M. leprae* and *M. avium*) and in the relatively uncommon pathogens (*M. kansasii, M. ulcer-* ans, M. chelonae), and its presence in all the clinical isolates whose genomes have been sequenced or were included in our experiments suggests that PTRP may contribute to the pathogenesis of Mtb.

PTRP was originally identified by screening of an expression library of Mtb genomic DNA in λgt11 with sera from Mtb H37Rv aerosol-infected rabbits (49). Preliminary studies by the inventors with the β-galactosidase fusion protein that contained only the C-terminal 211 aa of PTRP had suggested that it elicited antibodies in TB patients (49). The presence of anti-PTRP antibodies in sera from a majority of both HIV$^-$TB$^+$ and HIV+TB$^+$ patients and their absence in sera from PPD$^+$ and PPD$^-$ healthy subjects, as well as HIV+ TB− subjects confirms its immunogenicity during active infection with Mtb. Thus, PTRP is useful as in a diagnostic test for TB.

Several peptide based diagnostic tests have been successfully developed to diagnose other bacterial, viral and parasitic diseases (1, 16, 32). Although PTRP was successfully expressed as PTRP-GST fusion protein, and the GST could be cleaved to obtain small quantities of PTRP, attempts to scale-up production of the purified protein were unsuccessful. The cell-wall location and the strong immunogenicity of PTRP in TB patients prompted attempts to define its immunogenic regions. Screening of overlapping peptides of PTRP with sera from TB patients and PPD$^+$ and PPD$^-$ healthy controls delineated several immunogenic peptides that were recognized by antibodies in sera from the former but not the latter individuals. Although antibodies to one or more peptides of PTRP were detected in 95% of the TB patients, 4 immunodominant peptides that together could identify >80% of the smear-positive HIV$^-$TB$^+$ patients were defined. The lack of antibodies to these peptides in sera from PPD$^+$ subjects indicates that individuals with latent Mtb infection and/or BCG vaccination do not have antibodies to these peptides. Studies are evaluating the sensitivity and specificity provided by these peptides in TB patients at different stages of disease progression (smear positive or smear negative, cavitary or non-cavitary) and different classes of TB patients (HIV$^-$TB$^+$ or HIV+TB$^+$, pulmonary or extrapulmonary TB). Additional immunodominant peptides from other highly antigenic proteins identified in our previous studies are being delineated to further enhance the sensitivity of TB diagnosis (41, 42, 47-49).

Several gram-positive bacteria, other mycobacteria and fungi express cell wall or secreted proteins that have regions containing tandem repeats of unique amino acid motifs (12, 14, 19, 24, 28, 30, 31, 35, 43, 45, 46). Many of these repetitive proteins are cell-attachment proteins that contribute to adherence of the pathogen to host cells and/or invasion via the ability to bind to ECM proteins or to other host-cell ligands (12, 14, 19, 30, 35, 45, 46). Thus, the HBHA is a surface exposed cell-wall protein of Mtb that binds to heparin via its C-terminal repeat region and promotes bacterial entry into epithelial cells in vitro, and contributes to dissemination of Mtb from the lungs to spleen in vivo in mice (29, 30, 36, 37). Similarly, the ML-LBP21 is a surface exposed cell-wall protein of *M. leprae* that binds to laminin, facilitates adherence of bacilli to Schwann cells (9) and can mediate the entry of ML-LBP21 coated latex beads into these cells (46). Preliminary studies with purified PTRP demonstrate that it binds to thrombospondin, laminin and fibronectin; PTRP is the only thrombospondin-binding mycobacterial adhesin reported so far. Thrombospondins are a family of extracellular proteins that are involved in cell-to-cell and cell-to-matrix adherence and communication (22). Although little information on the mechanism of bacterial-thrombospondin interaction is available, studies have shown that thrombospondin mediates adherence of *Staphylococcus* to activated platelets, blood clots and to extracellular matrices during pyogenic infection (18). It also binds to clinical strains of *Enterococci* and surface layer proteins of *Clostridium difficile* (4, 56). Moreover, studies with *Streptococcus pneumoniae*, *Staphylococcus aureus* and *Listeria monocytogenes* have demonstrated the ability of thrombospondin to promote their colonization of human epithelial and endothelial cell-lines (39). Laminin is present on the basolateral surface of epithelial cells that line the alveoli, and is a major constituent of the basement membrane of underlying these cells. The ability of PTRP to bind to laminin suggests a possible role for this protein in migration of bacteria into the circulation (5, 10, 21). Interestingly, another immunodominant cell-wall/secreted laminin binding protein of Mtb, malate synthase has been demonstrated to contribute to the adherence of Mtb to type 2 lung epithelial cells (21). Fibronectin contributes to the attachment of Mtb to alveolar macrophages (34). The probable function of PTRP as an adhesin of Mtb is also supported by its localization on the cell-wall of Mtb. It is interesting that while the primary domain organization of PTRP, HBHA, ML-LBP21 and Cnm is similar, the secondary structures of PTRP and Cnm are quite different from those of HBHA and ML-LBP21 (FIG. 1). Whether, and how these differences translate into differences in the host-pathogen interactions remains to be determined.

In summary, PTRP is a Mtb complex specific cell-wall protein of Mtb. Antibodies to PTRP are useful as biomarkers for identification of active infection with Mtb in both HIV$^-$TB$^+$ and HIV+TB$^+$ patients, and 4 immunodominant regions of the protein have been identified. Moreover, this surface-exposed cell-wall protein is also an adhesin of Mtb, which may enhance the adherence both to alveolar macrophages and to pulmonary epithelial and endothelial cells via its ability to bind to thrombospondin, laminin and fibronectin. Further studies to define the role of PTRP in colonization of host cells to establish infection and in host-pathogen interaction are ongoing.

EXAMPLE IX

PE-PGRS-1 is a Target of Immune Responses; Identification of Immunodominant Epitopes of PE-PGRS-1

PE-PGRS51 is a 588 amino acid (~50 kDa) protein, that has the conserved ~110 aa N-terminal domain with the Pro-Glu (PE) motif at amino acids A and B, and 39 tandem copies of motif Gly-Gly-Ala/Asn (GGA/N) and 43 of motif Gly-Gly-Xaa (GGX) (wherein Xaa is any amino acid) spanning the C-terminal region. PE-PGRS51 comprises a signal sequence (aa 1-34) and 5 trans-membrane helices, suggesting an extracellular/surface localization in the bacterium. Two O-glycosylation sites and 1 N-glycosylation site are predicted.

PE-PGRS51 shows ~40-60% amino acids sequence identity with 47 other PE-PGRS proteins of *M. tuberculosis*; and <35% sequence identity with 14 additional PE-PGRS proteins. PE-PGRS51 homologues are present in Mtb H37Ra, *M. bovis*, *M. tuberculosis* CDC1551, *M. tuberculosis* F11, but not in *M. avium*, *M. avium paratuberculosis* and *M. leprae* (genome databases).

Presence of PE-PGRS51 in Mycobacterial Species and *M. tuberculosis* Clinical Isolates Since only a few mycobacterial species have been sequenced so far, the specificity of the PE-PGRS51 gene for *M. tuberculosis* was investigated. Stock cultures of *M. tuber-* culosis H37Rv, *M. bovis, M. bovis* BCG, *M. africanum, M. microti, M. avium, M. kansasii, M. scrofulaceum, M. intracellulare, M. fortuitum, M. smegmatis* mc, *M. vaccae, M. phlei, M. chelonae,* and *M. xenopii* were obtained from ATCC (Rockville, Md./Manassas, Va.). The bacteria were grown in 7H9 broth supplemented with 0.2% glycerol, 0.05% Tween 80 and 1× albumin dextrose saline (ADS; 0.5% bovine serum albumin, fraction V; 0.2% dextrose; and 0.85% NaCl).

The genomic DNA of these mycobacterial species was isolated. Genomic DNA of *M. tuberculosis* H37Rv, *M. tuberculosis* H37Ra, *M. tuberculosis* Erdman, and 7 *M. tuberculosis* clinical isolates were obtained from the NIH/NIAID TB Research Material and Vaccine Testing contract. DNA from 9 additional *M. tuberculosis* clinical isolates was procured from Dr. Barry Kreiswirth, Public Health Research Institute, Newark, N.J.

Genomic DNA (4 µg) from various mycobacterial species were digested with XhoI and separated on a 0.8% agarose gel and Southern blots were prepared.

To obtain the DIG-labeled PE-PGRS51 (1767 bp) for probing the Southern blots, the gene was amplified with primers (forward; 5'-GGGTTCATATGTCGTTTGTCGTAGC-3', SEQ ID NO:168) and (reverse; 5'-ACTGGAACGGCTG-GAAGCTTGCCGG-3' (SEQ ID NO:169) from *M. tuberculosis* H37Rv genomic DNA. The PCR product was cloned into pET23b+ vector (PE-PGRS51-pET23b+, Novagen, EMD Biosciences, Inc. San Diego, Calif.). The plasmid PE-PGRS51-pET23b+ DNA was digested with Nde I and Hind III to release PE-PGRS51 which was labeled with DIG (DIG probe synthesis kit, Roche Diagnostic Corporation, IN). The hybridization and detection were performed using DIG standard hybridization buffer and chemiluminescent detection system according to manufacturer's protocols (Roche).

The presence/absence of PE-PGRS51 in the various mycobacterial species and clinical isolates was also confirmed by PCR. The complete gene (1786 bp) was amplified from the genomic DNAs using primers PE-PGRS 1F (5'-AT-GTCGTTTGTCGTAGCAGTCC-3'; SEQ ID NO:170) and PE-PGRS 1R (5'-GCACTGGAACGGCTGGTAATTAG-3'; SEQ ID NO:171). Southern blots prepared with these amplified PCR products were probed with the respective DIG-labeled PE-PGRS51 gene fragments amplified from *M. tuberculosis* H37Rv genomic DNA (Roche). The hybridization and detection were performed as described above.

The DIG-labeled PE-PGRS51 probe hybridized with genomic DNA from various mycobacteria and a major ~5.3 kb band was identified in the DNA from *M. tuberculosis* complex species but not from any of the non-TB mycobacterial species tested. Further confirmation of the restriction of PE-PGRS51 to *M. tuberculosis* complex was provided when the ~1.8 kb PE-PGRS51 gene could be amplified by PCR only from these but not from any NTM species tested. All 16 clinical isolates of *M. tuberculosis* tested also showed the presence of PE-PGRS51. Thus, PE-PGRS51 is present in members of the *M. tuberculosis* complex and the clinical isolates of *M. tuberculosis*, but not in the non-TB mycobacterial species tested.

PE-PGRS 51 is a Cell-Wall Protein.

There are currently no antibodies available that recognize PE-PGRS51 specifically and distinctly from other PE-PGRS proteins that may be present in the *M. tuberculosis* cell-wall.

To determine the localization of PE-PGRS51 in the mycobacterial cell, the *M. tuberculosis* PE-PGRS51 gene was overexpressed with a C-terminal His-tag in *M. smegmatis* by using standard molecular biology methods. Briefly, the PE-PGRS 51 gene obtained from the recombinant plasmid PE-PGRS51-pET23b+ by digesting with NdeI and HindIII was cloned into the mycobacterial expression vector pVV16 in frame with His tag at NdeI and HindIII site. The resulting recombinant plasmid was electroporated into *M. smegmatis* mc2 155. The recombinant and parental *M. smegmatis* strains containing PE-PGRS51 in pVV16 vector and only pVV16 vector respectively were grown in media containing appropriate concentrations of kanamycin and hygromycin for 36 hours (log phase) and the bacterial pellets were suspended in PBS containing protease inhibitors. The bacilli were lysed by 5-6 cycles of freeze/thaw on dry ice followed by disruption in bead beater. The resulting lysate was centrifuged to remove the cell debris and unbroken cells. To prepare the cytosolic and cell wall protein fractions, the lysate was further centrifuged at 30,000×g for 1 h at 4° C. The supernatant containing the cytosolic proteins was stored at −80° C. and the pellet containing cell-wall proteins was washed twice with PBS and resuspended in PBS containing protease inhibitors. Five µg of the lysate, cytosolic fraction or the cell-wall fraction prepared from the recombinant and the parental strains were separated on a 12% SDS-PA gel, and blots prepared. The blots were probed with anti-His mAb, followed by alkaline phosphatase conjugated anti-mouse Ig antibodies.

An ~82 kDa protein was identified by the anti-His mAb primarily in the cell-wall fraction prepared from *M. smegmatis* transformed with the recombinant plasmid. (The predicted molecular weight of the PE-PGRS51 is ~50 kDa, but proteins that are rich in Pro, Ala, Gly residues are known to provide aberrant mobility on SDS-PA gels). These results indicated that PE-PGRS51, like the other PE-PGRS proteins tested so far, is also a cell-wall protein.

Identification of Immunodominant Epitopes of PE-PGRS 51:

20-mer peptides, overlapping by 10 a.a., encompassing the entire 588 amino acid sequence of the PE-PGRS51 were synthesized commercially. All 58 peptides were labeled with a biotin residue at the N-terminal. Antibodies directed against the peptides was detected by a modified ELISA performed in commercially available streptavidin coated ELISA plates ("Streptawell" plates; Roche). Individual wells of the "streptawell" plates were coated with (50 µl/well) individual biotin-labeled peptides suspended at 2.5 µg/ml in PBS containing 7.5% FBS, 2.5% BSA (Blocking buffer) for 1 h at 37° C. Sera from patients and controls were diluted 1:20 in 0.1× blocking buffer, and 50 µl/well was added and plates were incubated for 1 h at 37° C. (final serum dilution is 1:40). Plates were washed with PBST, and 1000 µl/well of alkaline-phosphatase-conjugated protein A (1:2000 dilution, from Sigma-Aldrich) and alkaline phosphatase-conjugated anti human IgA (1:1000 dilution, Sigma Aldrich) was added. After 1 h of incubation, plates were washed with PBST, and the peptide-antibody complexes detected by adding the substrate pNPP substrate and reading the OD at 405 nm. Mean OD of the sera from the PPD$^-$ and the PPD$^+$ healthy subjects plus 4 standard deviations (SD) was used as cut-off to identify sera that had antibodies to the peptide(s). (Mean OD+4SD was used as the cut-off to select dominant epitopes instead of the more "liberal" Mean+2 (or 2.5 or 3) SD used by others to identify the highly immunogenic peptides. The use of these peptides on rapid formats where sensitivity can be compromised due to lack of extensive washing steps that are used in ELISA-based assays and highly immunogenic peptides provide an advantage. Initially all 58 peptides of PE-PGRS51 were tested for reactivity with sera from 13 PPD$^-$, 23 PPD$^+$ and 42 sputum-smear positive TB patients. There was no difference in the OD values obtained with sera from PPD$^-$ and PPD$^+$ healthy subjects. Using the above cutoff derived from samples of the 36 PPD$^-$/PPD$^+$ healthy subjects the different peptides were recognized by sera from 0-56% of the 42 patients (FIG. 3). An arbitrary cut-off of 45% sensitivity was used to select highly immunogenic peptides and 13 peptides were identified as highly immunogenic in these TB patients (FIG. 3).

These 13 peptides were tested for reactivity with sera from the 36 PPD⁻/PPD⁺ healthy subjects and 90 sputum smear positive TB patients (including 30/42 patients whose sera was used for screening and was available in sufficient volumes). Each specimen was tested three times for reactivity with each of the 13 peptides and only sera that were positive 2/3 or 3/3 times were considered positive. Again, there was no difference in the reactivity of sera from PPD⁺ and PPD⁻ subjects with any of these peptides. The final sensitivity provided by these 13 peptides ranged from 36% to 52% (FIG. 4). Sera from a vast majority of the patients contained antibodies against multiple peptides; additive reactivity with all 13 peptides provided a sensitivity of 87%.

To identify the immunodominant peptides, the data with the 13 highly immunogenic peptides were analyzed in 2 different manners. First, additive reactivity with the 4 most highly immunogenic peptides (PG2, PG31, PG50 and PG55, which were recognized by sera from 48, 52, 50 and 49% of the patients respectively) was calculated. Together the 4 peptides identified 81% of the smear positive TB patients. There was no difference in the reactivity of sera from PPD⁻ and PPD⁺ subjects with any of the peptides indicating that humans with latent $M.$ $tuberculosis$ infection and/or BCG vaccination lack antibodies to these peptides (specificity >97%) (FIG. 5).

In the second approach, the amino-acid sequence of all 13 immunodominant peptides was subjected to BLAST analysis against the $M.$ $tuberculosis$ H37Rv genome sequence. Peptides PG2, PG31, PG16, PG50 and PG51 identified similar peptides that showed >75% homology in 6, 2, 16, 30 and 12 other PE-PGRS proteins respectively. The BLAST of these 5 peptides showed <50% homology with 0-3 non-PE-PGRS or with hypothetical proteins of $M.$ $leprae$ or $M.$ $avium$. Thus, these peptides contain promiscuous epitopes that are conserved between several PE-PGRS proteins. The additive sensitivity provided by the 5 promiscuous epitopes was 76%, which is similar to the sensitivity obtained with all 13 peptides (81%). When the data with the 5 promiscuous dominant epitopes was further analyzed, the same sensitivity (76%) was obtained when the additive reactivity with 3 of the 5 promiscuous peptides (PG2, PG31 and PG50) was calculated. There was no difference between the reactivity of the PPD or PPD healthy subjects with these peptides (FIG. 5). Together these results demonstrate that the 3 promiscuous epitopes are highly immunogenic. In contrast, PG9, PG14, PG24, PG28, PG29, PG52, PG53 and PG55 showed no homologous peptide in any other PE-PGRS protein and represent PE-PGRS51-specific epitopes. The additive reactivity with all eight peptides had to be included to achieve the same sensitivity as the 3 promiscuous epitopes (76%).

In a direct ELISA, the OD value obtained with any specimen is a reflection of the titers of antibodies in that serum. Interestingly, when the delta OD values (OD obtained by any particular antibody-positive TB specimen minus the mean OD of the 36 PPD⁺/PPD⁻ healthy subjects plus 4 SD) obtained with the promiscuous immunodominant peptides (PG2, PG31, PG50) was compared with those obtained with the PE-PGRS51-specific immunodominant peptide (PG55), the difference in absorbance (ΔOD) values with the former peptides were significantly higher statistically (p values ranging from 0.002-0.19). These observations suggest that the titers of antibodies directed against promiscuous shared epitopes are higher than the titers of antibodies against epitopes that are parent protein specific.

To confirm that the same epitopes are also immunogenic in HIV+TB⁺ patients, the reactivity of the 3 promiscuous immunodominant peptides (PG2, PG31 and PG50) was tested with sera from 30 smear positive HV+TB⁺ patients and 20 HIV+ TB− subjects. Each of the 3 peptides was recognized by sera from 53-57% of the HIV+TB⁺ patients; the additive reactivity with the 3 peptides was 60% (FIG. 6). However, peptides PG2 and PG50 showed non-specific reactivity with sera from 2/20 and 1/20 HIV+TB− subjects respectively. Peptide PG31 alone provided 57% sensitivity with no cross-reactivity. These studies suggest that although the same epitopes are recognized by HIV⁻TB⁺ and HIV+TB⁺ patients, the hypergammaglobinemia caused by concurrent HIV infection may play a role in reducing specificity with some peptides.

The pe-pgrs51 gene was cloned into pVV16 for expression in $M.$ $smegmatis$. Subcellular fractions (cytosolic proteins, cell-wall, whole cell-lysate and CFP) of the parental and recombinant $M.$ $smegmatis$ were fractionated on SDS-PAGE and the western blots probed with anti-His antibody. The results demonstrated that PE-PGRS-1 localized to the $M.$ $smegmatis$ cell wall.

Mtb protein PE-PGRS-1 is target of immune responses during active infection with Mtb, both in HIV⁻TB⁺ and HIV+ TB⁺ patients. Considering that the PE-PGRS-1 is Mtb (complex) specific, is present in all clinical isolates of Mtb tested, and is recognized by antibodies in sera from TB patients, its potential for TB diagnosis was evaluated.

Fifty eight overlapping peptides representing the full length PTRP protein were synthesized commercially. The reactivity of 58 peptides was tested with sera from 60 HIV⁻ TB⁺ patients and 36 PPD⁺/PPD⁻ healthy controls. There was no significant difference in the reactivity of the PPD⁻ and PPD⁺ sera with 49 peptides (p=0.561-0.986); with remaining peptides the ODs obtained with the individual sera in PPD⁺ group (3 peptides) or PPD⁻ group (1 peptide) were relatively higher in comparison to respective PPD⁻ or PPD⁺ groups (not shown).

Using Mean OD+3SD of the 36 PPD⁻ and PPD⁺ healthy individuals as a cut-off, 22 peptides showed no reactivity with sera from any of the healthy controls and remaining peptides reacted only with 1 or 2 of these sera (FIG. 6A). 13/58 peptides were recognized by sera from at least 40% of HIV⁻TB⁺ patients (Table 2) and are therefore considered to be highly immunogenic. These 13 highly immunogenic peptides were retested twice with the same panel of sera to validate the results of the above screening There was no difference in the OD values obtained with the PPD⁻ and PPD⁺ healthy subjects with any of these peptides. In contrast, the OD values obtained with sera from TB patients were significantly higher for all the 13 peptides. Had the cut-off been calculated by using the OD values from only the PPD⁻ subjects, the sensitivity of antibody detection in TB patients would either be unaffected or be enhanced.

TABLE 2

PE-PGRS-1 overlapping peptides and their Immunoreactivity

| Peptide Name | Sequence | SEQ ID NO | MW (daltons) | Immunoreactive* |
|---|---|---|---|---|
| PG-1 | MSFVVAVPEALAAAASDVAN | 61 | 2272 | |
| PG-2 | LAAAASDVANIGSALSAANA | 62 | 2097 | ++ |
| PG-3 | IGSALSAANAAAAAGTTGLL | 63 | 2040 | |

TABLE 2-continued

PE-PGRS-1 overlapping peptides and their Immunoreactivity

| Peptide Name | Sequence | SEQ ID NO | MW (daltons) | Immunoreactive* |
|---|---|---|---|---|
| PG-4 | AAAAGTTGLLAAGADEVSAA | 64 | 2027 | |
| PG-5 | AAGADEVSAALASLFSGHAV | 65 | 2183 | |
| PG-6 | LASLFSGHAVSYQQVAAQAT | 66 | 2388 | |
| PG-7 | SYQQVAAQATALHDQFVQAL | 67 | 2528 | |
| PG-8 | ALHDQFVQALTGAGGSYALT | 68 | 2359 | |
| PG-9 | TGAGGSYALTEAANVQQNLL | 69 | 2317 | ++ |
| PG-10 | EAANVQQNLLNAINAPTQAL | 70 | 2432 | |
| PG-11 | NAINAPTQALLGRPLIGDGA | 71 | 2301 | |
| PG-12 | LGRPLIGDGAVGTASSPDGQ | 72 | 2207 | |
| PG-13 | VGTASSPDGQDGGLLFGNGG | 73 | 2145 | |
| PG-14 | DGGLLFGNGGAGYNSAATPG | 74 | 2135 | ++ |
| PG-15 | AGYNSAATPGMAGGNGGNAG | 75 | 2034 | |
| PG-16 | MAGGNGGNAGLIGNGGTGGS | 76 | 1958 | ++ |
| PG-17 | LIGNGGTGGSGGAGAAGGAG | 77 | 1797 | |
| PG-18 | GGAGAAGGAGGSGGWLYGNG | 78 | 1933 | |
| PG-19 | GSGGWLYGNGGNGGIGGNAI | 79 | 2117 | |
| PG-20 | GNGGIGGNAIVAGGAGGNGG | 80 | 1866 | |
| PG-21 | VAGGAGGNGGAGGAAGLWGS | 81 | 1883 | |
| PG-22 | AGGAAGLWGSGGSGGQGGNG | 82 | 1914 | |
| PG-23 | GGSGGQGGNGLTGNDGVNPA | 83 | 2025 | |
| PG-24 | LTGNDGVNPAPVTNPALNGA | 84 | 2231 | ++ |
| PG-25 | PVTNPALNGAAGDSNIEPQT | 85 | 2305 | |
| PG-26 | AGDSNIEPQTSVLIGTQGGD | 86 | 2298 | |
| PG-27 | SVLIGTQGGDGTPGGAGVNG | 87 | 2053 | |
| PG-28 | GTPGGAGVNGGNGGAGGDAN | 88 | 1895 | ++ |
| PG-29 | GNGGAGGDANGNPANTSIAN | 89 | 2068 | ++ |
| PG-30 | GNPANTSIANAGAGGNGAAG | 90 | 1981 | |
| PG-31 | AGAGGNGAAGGDGGANGGAG | 91 | 1754 | ++ |
| PG-32 | GDGGANGGAGGAGGQAASAG | 92 | 1798 | |
| PG-33 | GAGGQAASAGSSVGGDGGNG | 93 | 1872 | |
| PG-34 | SSVGGDGGNGGAGGTGTNGH | 94 | 1955 | |
| PG-35 | GAGGTGTNGHAGGAGGAGGA | 95 | 1793 | |
| PG-36 | AGGAGGAGGAGGRGGWLVGN | 96 | 1938 | |
| PG-37 | GGRGGWLVGNGGNGGNGAAG | 97 | 2024 | |
| PG-38 | GGNGGNGAAGGNGAIGGTGG | 98 | 1811 | |
| PG-39 | GNGAIGGTGGAGGVPANQGG | 99 | 1908 | |
| PG-40 | AGGVPANQGGNSALGTQPVG | 100 | 2091 | |
| PG-41 | NSALGTQPVGGDGGDGGNGG | 101 | 2026 | |
| PG-42 | GDGGDGGNGGTGGTGGRGGD | 102 | 1916 | |
| PG-43 | TGGTGGRGGDGGSGGAGGAS | 103 | 1831 | |
| PG-44 | GGSGGAGGASGWLMGNGGNG | 104 | 1960 | |
| PG-45 | GWLMGNGGNGGNGGTGGSGG | 105 | 2003 | |
| PG-46 | GNGGTGGSGGVGGNGGIGGD | 106 | 1842 | |
| PG-47 | VGGNGGIGGDGAGGGNATST | 107 | 1915 | |
| PG-48 | GAGGGNATSTSSIPFDAHGG | 108 | 2100 | |
| PG-49 | SSIPFDAHGGNGGAGGDAGH | 109 | 2120 | |
| PG-50 | NGGAGGDAGHGGTGGDGGDG | 110 | 1881 | ++ |
| PG-51 | GGTGGDGGDGGHAGTGGRGG | 111 | 1895 | ++ |
| PG-52 | GHAGTGGRGGLLAGQHANSG | 112 | 2114 | ++ |
| PG-53 | LLAGQHANSGNGGGGGTGGA | 113 | 1992 | ++ |
| PG-54 | NGGGGGTGGAGGTHGTPGSG | 114 | 1851 | |
| PG-55 | GGTHGTPGSGNAGGTGTGNA | 115 | 1967 | ++ |
| PG-56 | NAGGTGTGNADSTNGGPGSD | 116 | 2046 | |
| PG-57 | DSTNGGPGSDGLGGDAFNGS | 117 | 2121 | |
| PG-58 | SDGLGGDAFNGSRGTDGNPG | 118 | 2190 | |

* ++ indicates that the peptides were recognized by 40% or more TB patient sera. Peptides were biotinylated at the N-terminus for immobilization to a surface coated with streptavidin. All peptides were analyzed by MALDI + MS. All peptides passed MS analysis and the final gross weight criteria (>5 mg).

EXAMPLE X

Identification of Immunodominant Epitopes of LipC

LipC (originally identified as Rv0220) is a 403 amino acid, 44 kDa protein, annotated as a probable esterase in the Mtb database. It is a member of a family of 24 proteins, two of which (LipY and LipH) have been shown to be induced during starvation and under acidic conditions. Since this protein was identified as an Mtb antigen by use of antibodies from Mtb-infected rabbits, experiments were performed to determine if human TB patients have antibodies to this protein.

The lipC gene was cloned for expression in E. coli. The purified His-tagged recombinant protein was examined by Western blot in which individual lanes were probed with sera from 6 HIV⁻TB⁺, 6 HIV+TB⁺, 6 HIV+TB−, 6 HIV−PPD⁻ and 6 HIV−PPD⁺ subjects. Sera from 11/12 TB patients (5/6 HIV⁻TB⁺ and 6/6 HIV⁺TB⁺ patients showed the presence of anti-LipC antibodies demonstrating that it is also a highly immunogenic protein in humans (FIG. 17). Some control sera show background cross-reactivity with the His-LipC.

As was done for pe-pgrs51, the lipC gene was also cloned into pVV16 for expression in M. smegmatis. Subcellular fractions (cytosolic proteins, cell-wall, whole cell-lysate and CFP) of the parental and recombinant *M. smegmatis* were fractionated on SDS-PAG and the western blots probed with anti-His antibody. The results demonstrated that LipC also localizes to the *M. smegmatis* cell-wall.

Forty overlapping peptides representing the full length LipC protein were synthesized commercially. The reactivity of the peptides was tested with sera from 60 HIV⁻TB⁺ patients and 36 PPD⁺/PPD⁻ healthy controls. Peptides were biotinylated at the N-terminus for immobilization to a surface coated with streptavidin. All peptides were analyzed by MALDI and MS (and passed MS analysis and the final gross weight criteria (>5 mg).

Results are shown in Table 3. There was no significant difference in the reactivity of the PPD⁻ and PPD⁺ sera with 33 peptides; with remaining peptides the ODs obtained with the individual sera in PPD⁺ group (3 peptides) or PPD⁻ group (1 peptide) were relatively higher in comparison to respective PPD⁻ or PPD⁺ groups (data not shown)f Using Mean OD+3D of the PPD⁻ and PPD⁺ healthy individuals as a cut-off, 40 peptides showed no reactivity with sera from any of the healthy controls. Seven of 40 peptides were recognized by sera from at least 45% of HIV⁻TB⁺ patients (Table 3) and are therefore considered to be highly immunogenic.

TABLE 3

LipC overlapping peptides and their Immunoreactivity

| LipC Peptide | Sequence | Seq ID No: | MW (d) | Immuno-reactive* |
|---|---|---|---|---|
| Lp-1 | MNQRRAAGSTGVAYIRWLLR | 119 | 2659 | |
| Lp-2 | GVAYIRWLLRARPADYMLAL | 120 | 2688 | |
| Lp-3 | ARPADYMLALSVAGGSLPVV | 121 | 2326 | ++ |
| Lp-4 | SVAGGSLPVVGKHLKPLGGV | 122 | 2211 | ++ |
| Lp-5 | GKHLKPLGGVTAIGVWGARH | 123 | 2393 | |
| Lp-6 | TAIGVWGARHASDFLSATAK | 124 | 2398 | ++ |
| Lp-7 | ASDFLSATAKDLLTPGINEV | 125 | 2401 | |
| Lp-8 | DLLTPGINEVRRRDRASTQE | 126 | 2666 | |
| Lp-9 | RRRDRASTQEVSVAALRGIV | 127 | 2580 | |
| Lp-10 | VSVAALRGIVSPDDLAVEWP | 128 | 2433 | |
| Lp-11 | SPDDLAVEWPAPERTPPVCG | 129 | 2475 | |
| Lp-12 | APERTPPVCGALRHRRYVHR | 130 | 2711 | |
| Lp-13 | ALRHRRYVHRRRVLYGDDPA | 131 | 2846 | |
| Lp-14 | RRVLYGDDPAQLLDVWRRKD | 132 | 2811 | |
| Lp-15 | QLLDVWRRKDMPTKPAPVLI | 133 | 2716 | |
| Lp-16 | MPTKPAPVLIFVPGGAWVHG | 134 | 2414 | |
| Lp-17 | FVPGGAWVHGSRAIQGYAVL | 135 | 2424 | |
| Lp-18 | SRAIQGYAVLSRLAAQGWVC | 136 | 2488 | |
| Lp-19 | SRLAAQGWVCLSIDYRVAPH | 137 | 2582 | |
| Lp-20 | LSIDYRVAPHHRWPRHILDV | 138 | 2820 | |
| Lp-21 | HRWPRHILDVKTAIAWARAN | 139 | 2751 | |

TABLE 3-continued

LipC overlapping peptides and their Immunoreactivity

| LipC Peptide | Sequence | Seq ID No: | MW (d) | Immuno-reactive* |
|---|---|---|---|---|
| Lp-22 | KTAIAWARANVDKFGGDRNF | 140 | 2576 | |
| Lp-23 | VDKFGGDRNFIAVAGCSAGG | 141 | 2280 | |
| Lp-24 | IAVAGCSAGGHLSALAGLTA | 142 | 2079 | ++ |
| Lp-25 | HLSALAGLTANDPQYQAELP | 143 | 2448 | |
| Lp-26 | NDPQYQAELPEGSDTSVDAV | 144 | 2474 | ++ |
| Lp-27 | EGSDTSVDAVVGIYGRYDWE | 145 | 2557 | |
| Lp-28 | VGIYGRYDWEDRSTPERARF | 146 | 2813 | |
| Lp-29 | DRSTPERARFVDFLERVVVQ | 147 | 2759 | |
| Lp-30 | VDFLERVVVQRTIDRHPEVF | 148 | 2794 | |
| Lp-31 | RTIDRHPEVFRDASPIQRVT | 149 | 2733 | |
| Lp-32 | RDASPIQRVTRNAPPFLVIH | 150 | 2627 | |
| Lp-33 | RNAPPFLVIHGSRDCVIPVE | 151 | 2559 | |
| Lp-34 | GSRDCVIPVEQARSFVERLR | 152 | 2657 | ++ |
| Lp-35 | QARSFVERLRAVSRSQVGYL | 153 | 2662 | |
| Lp-36 | AVSRSQVGYLELPGAGHGFD | 154 | 2399 | |
| Lp-37 | ELPGAGHGFDLLDGARTGPT | 155 | 2320 | |
| Lp-38 | LLDGARTGPTAHAIALFLNQ | 156 | 2418 | |
| Lp-39 | AHAIALFLNQVHRSRAQFAK | 157 | 2618 | ++ |
| Lp-40 | IALFLNQVHRSRAQFAKEVI | 158 | 2680 | |

* Immunoreactivity : ++ immunodominant based on being recognized by 45% or more patient sera.

References cited above which by numbers in parentheses are listed below:

REFERENCES

1. Alcaro, M. C., E. Peroni, P. Rovero, and A. M. Papini. 2003. Synthetic peptides in the diagnosis of HIV infection. Curr Protein Pept Sci 4:285-290
2. Betts, J. C., P. Dodson, S. Quan, A. P. Lewis, P. J. Thomas, K. a. Duncan, and R. A. McAdam. 2000. Comparison of the proteome of *Mycobacterium tuberculosis* strain H37Rv with clinical isolate CDC 1551. Microbiology 146:3205-3216
3. Butcher, P. D., J. A. Mangan, and I. M. Monahan. 1999. Intracellular gene expression-analysis of RNA from mycobacteria in macrophages using RT-PCR. Methods in Molecular Biology 101:285-306
4. Calabi, E., F. Calabi, A. D. Phillips, and N. F. Fairweather. 2002. Binding of *Clostridium difficile* surface layer proteins to gastrointestinal tissues. Infect Immun 70:5770-5778
5. Carterson, A. J., K. Honer zu Bentrup, C. M. Ott, M. S. Clarke, D. L. Pierson, C. R. Vanderburg, K. L. Buchanan, C. A. Nickerson, and M. J. Schurr. 2005. A549 lung epithelial cells grown as three-dimensional aggregates: alternative tissue culture model for *Pseudomonas aeruginosa* pathogenesis. Infect Immun 73:1129-1140

6. Chan, K., T. Knaak, L. Satkamp, O. Humbert, S. Falkow, and L. Ramakrishnan. 2002. Complex pattern of *Mycobacterium marinum* gene expression during long-term granulomatous infection. Proc Natl Acad Sci USA 99:3920-3925
7. Cole, S. T. et al., 1998. Deciphering the biology of *Mycobacterium tuberculosis* from the complete genome sequence. Nature 393:537-544
8. Dasgupta, N., and J. S. Tyagi. 1998. Identification of a restriction fragment length polymorphism associated with deletion that maps in a transcriptionally active open-reading frame, orfX, in *Mycobacterium tuberculosis* Erdman. Tuber Lung Dis 79:75-81
9. de Melo Marques, M. A., S. Mahapatra, D. Nandan, T. Dick, E. N. Sarno, P. J. Brennan, and M. C. Vidal Pessolani. 2000. Bacterial and host-derived cationic proteins bind alpha2-laminins and enhance *Mycobacterium leprae* attachment to human Schwann cells. Microbes Infect 2:1407-1417
10. DeBiase, P. J., K. Lane, S. Budinger, K. Ridge, M. Wilson, and J. C. Jones. 2006. Laminin-311 (Laminin-6) fiber assembly by type I-like alveolar cells. J Histochem Cytochem 54:665-672
11. Dubnau, E., P. Fontan, R. Manganelli, S. Soares-Appel, and I. Smith. 2002. *Mycobacterium tuberculosis* genes induced during infection of human macrophages. Infect Immun 70:2787-2795
12. Fischetti, V. A. 2000. Surface Proteins on Gram-Positive Bacteria, p. 11-24. In A. S. f. Microbiology (ed.), Gram-Positive Pathogens. Washington, D.C.
13. Fleischmann, R. D. et al., 2002. Whole-genome comparison of *Mycobacterium tuberculosis* clinical and laboratory strains. J Bacteriol 184:5479-5490
14. Foster, T., and M. Hook. 1998. Surface protein adhesins of *Staphylococcus aureus*. Trends in Microbiology 6:484-488
15. Geiman, D. E., D. Kaushal, C. Ko, S. Tyagi, Y. C. Manabe, B. G. Schroeder, R. D. Fleischmann, N. E. Morrison, P. J. Converse, P. Chen, and W. R. Bishai. 2004. Attenuation of late-stage disease in mice infected by the *Mycobacterium tuberculosis* mutant lacking the SigF alternate sigma factor and identification of SigF-dependent genes by microarray analysis. Infect Immun 72:1733-1745
16. Gomara, M. J., and I. Haro. 2007. Synthetic peptides for the immunodiagnosis of human diseases. Curr Med Chem 14:531-546
17. Gu, S., J. Chen, K. M. Dobos, E. M. Bradbury, J. T. Belisle, and X. Chen. 2003. Comprehensive proteomic profiling of the membrane constituents of a *Mycobacterium tuberculosis* strain. Mol Cell Proteomics 2:1284-1296
18. Herrmann, M., S. J. Suchard, L. A. Boxer, F. A. Waldvogel, and P. D. Lew. 1991. Thrombospondin binds to *Staphylococcus aureus* and promotes staphylococcal adherence to surfaces. Infect Immun 59:279-288
19. Jadoun, J., V. Ozeri, E. Burstein, E. Skutelsky, E. Hanski, and S. Sela. 1998. Protein F1 is required for efficient entry of *Streptococcus pyogenes* into epithelial cells. J Infect Dis 178:147-158
20. Jungblut, P. R., U. E. Schaible, H. J. Mollenkopf, U. Zimny-Arndt, B. Raupach, J. Mattow, P. Halada, S. Lamer, K. Hagens, and S. H. Kaufmann. 1999. Comparative proteome analysis of *Mycobacterium tuberculosis* and *Mycobacterium bovis* BCG strains: towards functional genomics of microbial pathogens. Mol Microbiol 33:1103-1117
21. Kinhikar, A., D. Vargas, H. Li, S. B. Mahaffey, L. Hinds, J. T. Belisle, and S. Laal. 2006. *Mycobacterium tuberculosis* malate synthase is a laminin binding adhesin. Mol Microbiol 60:999-1013
22. Lawler, J. 2000. The functions of thrombospondin-1 and -2. Curr Opin Cell Biol 12:634-640
23. Li, L., J. P. Bannantine, Q. Zhang, A. Amonsin, B. J. May, D. Alt, N. Banerji, S. Kanjilal, and V. Kapur. 2005. The complete genome sequence of *Mycobacterium avium* subspecies *paratuberculosis*. Proc Natl Acad Sci USA 102:12344-12349
24. Lukomski, S., K. Nakashima, I. Abdi, V. J. Cipriano, R. M. Ireland, S. D. Reid, G. G. Adams, and J. M. Musser. 2000. Identification and characterization of the scl gene encoding a group A *Streptococcus* extracellular protein virulence factor with similarity to human collagen. Infect Immun 68:6542-6553
25. Malen, H., F. S. Berven, K. E. Fladmark, and H. G. Wiker. 2007. Comprehensive analysis of exported proteins from *Mycobacterium tuberculosis* H37Rv. Proteomics 7:1702-1718
26. Mattow, J., U. E. Schaible, F. Schmidt, K. Hagens, F. Siejak, G. Brestrich, G. Haeselbarth, E. C. Muller, P. R. Jungblut, and S. H. Kaufmann. 2003. Comparative proteome analysis of culture supernatant proteins from virulent *Mycobacterium tuberculosis* H37Rv and attenuated *M. bovis* BCG Copenhagen. Electrophoresis 24:3405-3420
27. Mawuenyega, K. G., C. V. Forst, K. M. Dobos, J. T. Belisle, J. Chen, E. M. Bradbury, A. R. Bradbury, and X. Chen. 2005. *Mycobacterium tuberculosis* functional network analysis by global subcellular protein profiling. Mol Biol Cell 16:396-404
28. McNab, R., A. R. Holmes, J. M. Clarke, G. W. Tannock, and H. F. Jenkinson 1996. Cell surface polypeptide CshA mediates binding of *Streptococcus gordonii* to other oral bacteria and to immobilized fibronectin. Infect Immun 64:4204-4210
29. Menozzi, F. D., R. Bischoff, E. Fort, M. J. Brennan, and C. Locht. 1998. Molecular characterization of the mycobacterial heparin-binding hemagglutinin, a mycobacterial adhesin. Proc. Natl. Acad. Sci. USA 95:12625-12630
30. Menozzi, F. D., J. H. Rouse, M. Alavi, M. Laude-Sharp, J. Muller, R. Bischoff, M. J. Brennan, and C. Locht. 1996. Identifiacation of a heparin-binding hemagglutinin present in mycobacteria. J Exp Med 184:993-1001
31. Nallapareddy, S. R., K. V. Singh, R. W. Duh, G. M. Weinstock, and B. E. Murray. 2000. Diversity of ace, a gene encoding a microbial surface component recognizing adhesive matrix molecules, from different strains of *Enterococcus faecalis* and evidence for production of ace during human infections. Infect Immun 68:5210-5217
32. Noya, O., M. E. Patarroyo, F. Guzman, and B. Alarcon de Noya. 2003 Immunodiagnosis of parasitic diseases with synthetic peptides. Curr Protein Pept Sci 4:299-308
33. Olakanmi, O., B. E. Britigan, and L. S. Schlesinger. 2000. Gallium disrupts iron metabolism of mycobacteria residing within human macrophages. Infect Immun 68:5619-5627
34. Pasula, R., P. Wisniowski, and W. J. Martin, 2nd. 2002. Fibronectin facilitates *Mycobacterium tuberculosis* attachment to murine alveolar macrophages. Infect Immun 70:1287-1292
35. Patti, J. M., B. L. Allen, M. J. McGavin, and M. Hook. 1994. MSCRAMN-mediated adherence of microorganisms to host tissues. Annu. Rev. Microbiol. 48:585-617

36. Pethe, K., S. Alonso, F. Biet, G. Delogu, M. J. Brennan, C. Locht, and F. D. Menozzi. 2001. The heparin-binding haemagglutinin of *M. tuberculosis* is required for extrapulmonary dissemination. Nature 412:190-194
37. Pethe, K., M. Aumercier, E. Fort, C. Gatot, C. Locht, and F. D. Menozzi. 2000. Characterization of the heparin-binding site of the mycobacterial heparin-binding hemagglutinin Adhesin. J Biol Chem 275:14273-14273
38. Rachman, H., M. Strong, T. Ulrichs, L. Grode, J. Schuchhardt, H. Mollenkopf, G. A. Kosmiadi, D. Eisenberg, and S. H. Kaufmann. 2006. Unique transcriptome signature of *Mycobacterium tuberculosis* in pulmonary tuberculosis. Infect Immun 74:1233-1242
39. Rennemeier, C., S. Hammerschmidt, S. Niemann, S. Inamura, U. Zahringer, and B. E. Kehrel. 2007. Thrombospondin-1 promotes cellular adherence of gram-positive pathogens via recognition of peptidoglycan. FASEB J 21:3118-3132
40. Rosenkrands, I., K. Weldingh, S. Jacobsen, C. V. Hansen, W. Florio, I. Gianetri, and P. Andersen. 2000. Mapping and Identification of *Mycobacterium tuberculosis* proteins by two-dimensional gel electrophoresis, microsequencing and immunodetection. Electrophoresis 21:935-948
41. Samanich, K., J. T. Belisle, and S. Laal. 2001. Homogeneity of antibody responses in tuberculosis patients. Infect Immun 69:4600-4609
42. Sartain, M. J., R. A. Slayden, K. K. Singh, S. Laal, and J. T. Belisle. 2006. Disease state differentiation and identification of tuberculosis biomarkers via native antigen profiling. Mol Cel Proteomics 5:2102-2113
43. Sato, Y., K. Okamoto, A. Kagami, Y. Yamamoto, T. Igarashi, and H. Kizaki. 2004. *Streptococcus mutans* strains harboring collagen-binding adhesin. J Dent Res 83:534-539
44. Schmidt, F., S. Donahoe, K. Hagens, J. Mattow, U. E. Schaible, S. H. Kaufmann, R. Aebersold, and P. R. Jungblut. 2004. Complementary analysis of the *Mycobacterium tuberculosis* proteome by two-dimensional electrophoresis and isotope-coded affinity tag technology. Mol Cell Proteomics 3:24-42
45. Sheppard, D. C., M. R. Yeaman, W. H. Welch, Q. T. Phan, Y. Fu, A. S. Ibrahim, S. G. Filler, M. Zhang, A. J. Waring, and J. E. Edwards, Jr. 2004. Functional and structural diversity in the Als protein family of *Candida albicans*. J Biol Chem 279:30480-30489
46. Shimoji, Y., V. Ng, K. Matsumura, V. A. Fischetti, and A. Rambukkana. 1999. A 21-kDa surface protein of *Mycobacterium leprae* binds peripheral nerve laminin-2 and mediates schwann cell invasion. Proc Natl Acad Sci 96:9857-9862
47. Singh, K. K., Y. Dong, J. T. Belisle, J. Harder, V. K. Arora, and S. Laal. 2005. Antigens of *Mycobacterium tuberculosis* recognized by antibodies during incipient, subclinical tuberculosis. Clin Diagn Lab Immunol 12:354-358
48. Singh, K. K., Y. Dong, A. Sai Patibandla, D. Mc Murray, V. K. Arora, and S. Laal. 2005. Immunogenicity of *Mycobacterium tuberculosis* PPE55 (Rv3347c) protein during incipient and clinical tuberculosis. Infect Immun 73:5004-5014
49. Singh, K. K., X. Zhang, A. S. Patibandla, P. Chien, Jr., and S. Laal. 2001. Antigens of *Mycobacterium tuberculosis* expressed during preclinical tuberculosis: serological immunodominance of proteins with repetitive amino acid sequences. Infect Immun 69:4185-4191
50. Sinha, S., K. Kosalai, S. Arora, A. Namane, P. Sharma, A. N. Gaikwad, P. Brodin, and S. T. Cole. 2005. Immunogenic membrane-associated proteins of *Mycobacterium tuberculosis* revealed by proteomics. Microbiology 151:2411-2419
51. Sonnenberg, M. G., and J. T. Belisle. 1997. Definition of *Mycobacterium tuberculosis* culture filtrate proteins by two-dimensional polyacrylamide gel electrophoresis, N-terminal amino acid sequencing and electrospray mass spectrometry. Infect. Immun. 65:4515-4524
52. Stinear, T. P. et al., 2007. Reductive evolution and niche adaptation inferred from the genome of *Mycobacterium ulcerans*, the causative agent of buruli ulcer. Genome Res 17:192-200
53. Talaat, A. M., R. Lyons, S. T. Howard, and S. A. Johnston. 2004. The temporal expression profile of *Mycobacterium tuberculosis* infection in mice. Proc Natl Acad Sci USA 101:4602-4607
54. Triccas, J. A., and B. Gicquel. 2000. Life on the inside: probing *Mycobacterium tuberculosis* gene expression during infection. Immunol Cell Biol 78:311-317
55. Xiong, Y., M. J. Chalmers, F. P. Gao, T. A. Cross, and A. G. Marshall. 2005. Identification of *Mycobacterium tuberculosis* H37Rv integral membrane proteins by one-dimensional gel electrophoresis and liquid chromatography electrospray ionization tandem mass spectrometry. J Proteome Res 4:855-861
56. Zareba, T. W., C. Pascu, W. Hryniewicz, and T. Wadstrom. 1997. Binding of extracellular matrix proteins by enterococci. Curr Microbiol 34:6-11

The references cited above are all incorporated by reference herein, whether specifically incorporated or not. Having now fully described this invention, it will be appreciated by those skilled in the art that the same can be performed within a wide range of equivalent parameters, concentrations, and conditions without departing from the spirit and scope of the invention and without undue experimentation.

What is claimed is:

1. A fusion polypeptide that comprises:
   (a) as a first fusion partner,
   (i) one or more peptide selected from the group consisting of:

| | | |
|---|---|---|
| PT-1  | MDVALGVAVTDRVARLALVD | (SEQ ID NO: 7) |
| PT-3  | SAAPGTVIDQFVLDVAEHPV | (SEQ ID NO: 9) |
| PT-6  | DRSLAGENHRLVATRLCWPD | (SEQ ID NO: 12) |
| PT-9  | LQDSGVHDVAVISEAQAATA | (SEQ ID NO: 15) |
| PT-13 | LSVVGDPDAPPTMVAVAPVA | (SEQ ID NO: 19) |
| PT-14 | PTMVAVAPVAGADATSTVDT | (SEQ ID NO: 20) |
| PT-20 | QTPDDPTFALARGAAMAAGA | (SEQ ID NO: 26) |
| PT-23 | DATTSLPRAEAGQSGSEGEQ | (SEQ ID NO: 29) |
| PT-34 | QQAPVPPPPPDDPTAGFQGG | (SEQ ID NO: 40) |
| PT-40 | PIPVPIIIPPFPGWQPGMPT | (SEQ ID NO: 46) |
| PT-41 | FPGWQPGMPTIPTAPPTTPV | (SEQ ID NO: 47) |
| PT-45 | TTPPTTPVTTPPTTPPTTPV | (SEQ ID NO: 51) |
| PG-2  | LAAAASDVANIGSALSAANA | (SEQ ID NO: 62) |
| PG-9  | TGAGGSYALTEAANVQQNLL | (SEQ ID NO: 69) |
| PG-14 | DGGLLFGNGGAGYNSAATPG | (SEQ ID NO: 74) |
| PG-16 | MAGGNGGNAGLIGNGGTGGS | (SEQ ID NO: 76) |
| PG-24 | LTGNDGVNPAPVTNPALNGA | (SEQ ID NO: 84) |
| PG-28 | GTPGGAGVNGGNGGAGGDAN | (SEQ ID NO: 88) |
| PG-29 | GNGGAGGDANGNPANTSIAN | (SEQ ID NO: 89) |
| PG-31 | AGAGGNGAAGGDGGANGGAG | (SEQ ID NO: 91) |
| PG-50 | NGGAGGDAGHGGTGGDGGDG | (SEQ ID NO: 110) |
| PG-51 | GGTGGDGGDGGHAGTGGRGG | (SEQ ID NO: 111) |
| PG-52 | GHAGTGGRGGLLAGQHANSG | (SEQ ID NO: 112) |
| PG-53 | LLAGQHANSGNGGGGGTGGA | (SEQ ID NO: 113) |
| PG-55 | GGTHGTPGSGNAGGTGTGNA | (SEQ ID NO: 115) |
| Lp-3  | ARPADYMLALSVAGGSLPVV | (SEQ ID NO: 121) |
| Lp-4  | SVAGGSLPVVGKHLKPLGGV | (SEQ ID NO: 122) |
| Lp-6  | TAIGVWGARHASDFLSATAK | (SEQ ID NO: 124) |
| Lp-24 | IAVAGCSAGGHLSALAGLTA | (SEQ ID NO: 142) |
| Lp-26 | NDPQYQAELPEGSDTSVDAV | (SEQ ID NO: 144) |
| Lp-34 | GSRDCVIPVEQARSFVERLR; and | (SEQ ID NO: 152) |
| Lp-39 | AHAIALFLNQVHRSRAQFAK | (SEQ ID NO: 157) | wherein said Pt-# peptides are fragments of the *Mycobacterium tuberculosis* (Mtb) protein PTRP (SEQ ID NO:2), said Pg-# peptides are fragments of the Mtb protein PE-PGRS51 (SEQ ID NO:4), and said Lp-# peptides are fragments of the Mtb protein LipC (SEQ ID NO:6), or
   (ii) a fragment of at least 10 residues of the peptide of (a)(i) or a conservative amino acid substitution variant of the peptide of (a)(i), which fragment or variant binds to an antibody specific for said PTRP protein, said PE-PGRS51 protein or said LipC protein of which said peptide of (a)(i) is a fragment,
   (b) linked to the peptide of (a)(i), or to the fragment or variant of (a)(ii), a second fusion partner polypeptide that is an early Mtb antigen,
   wherein the fusion polypeptide includes an optional linker or linkers linking any two or more of said fusion partners, said early Mtb antigen being one that induces an antibody response in an infected subject either before or after onset of constitutional symptoms of TB, but before the onset of specific symptoms identifiable as advanced TB that is distinguished by (A) smear positivity of sputum or other pulmonary associated fluid for acid-fast bacilli, (B) cavitary pulmonary lesions, or both (A) and (B).

2. A peptide multimer that:
   (a) has the formula $P^1_n$ wherein n=2-8, and
   $P^1$ is a peptide selected from the group consisting of:
   Pt-1 MDVALGVAVTDRVARLALVD (SEQ ID NO:7)
   Pt-3 SAAPGTVIDQFVLDVAEHPV (SEQ ID NO:9)
   Pt-6 DRSLAGENHRLVATRLCWPD (SEQ ID NO:12)
   Pt-9 LQDSGVHDVAVISEAQAATA (SEQ ID NO:15)
   Pt-13 LSVVGDPDAPPTMVAVAPVA (SEQ ID NO:19)
   Pt-14 PTMVAVAPVAGADATSTVDT (SEQ ID NO:20)
   Pt-20 QTPDDPTFALARGAAMAAGA (SEQ ID NO:26)

Pt-23 DATTSLPRAEAGQSGSEGEQ (SEQ ID NO:29)
Pt-34 QQAPVPPPPPDDPTAGFQGG (SEQ ID NO:40)
Pt-40 PIPVPIIIPPFPGWQPGMPT (SEQ ID NO:46)
Pt-41 FPGWQPGMPTIPTAPPTTPV (SEQ ID NO:47)
Pt-45 TTPPTTPVTTPPTTPPTTPV (SEQ ID NO:51)
Pg-2 LAAAASDVANIGSALSAANA (SEQ ID NO:62)
Pg-9 TGAGGSYALTEAANVQQNLL (SEQ ID NO:69)
Pg-14 DGGLLFGNGGAGYNSAATPG (SEQ ID NO:74)
Pg-16 MAGGNGGNAGLIGNGGTGGS (SEQ ID NO:76)
Pg-24 LTGNDGVNPAPVTNPALNGA (SEQ ID NO:84)
Pg-28 GTPGGAGVNGGNGGAGGDAN (SEQ ID NO:88)
Pg-29 GNGGAGGDANGNPANTSIAN (SEQ ID NO:89)
Pg-31 AGAGGNGAAGGDGGANGGAG (SEQ ID NO:91)
Pg-50 NGGAGGDAGHGGTGGDGGDG (SEQ ID NO:110)
Pg-51 GGTGGDGGDGGHAGTGGRGG (SEQ ID NO:111)
Pg-52 GHAGTGGRGGLLAGQHANSG (SEQ ID NO:112)
Pg-53 LLAGQHANSGNGGGGGTGGA (SEQ ID NO:113)
Pg-55 GGTHGTPGSGNAGGTGTGNA (SEQ ID NO:115)
Lp-3 ARPADYMLALSVAGGSLPVV (SEQ ID NO:121)
Lp-4 SVAGGSLPVVGKHLKPLGGV (SEQ ID NO:122)
Lp-6 TAIGVWGARHASDFLSATAK (SEQ ID NO:124)
Lp-24 IAVAGCSAGGHLSALAGLTA (SEQ ID NO:142)
Lp-26 NDPQYQAELPEGSDTSVDAV (SEQ ID NO:144)
Lp-34 GSRDCVIPVEQARSFVERLR (SEQ ID NO:152) and
Lp-39 AHAIALFLNQVHRSRAQFAK (SEQ ID NO:157),
wherein said Pt-# peptides are fragments of the Mtb protein PTRP (SEQ ID NO:2), said Pg-# peptides are fragments of the Mtb protein PE-PGRS51 (SEQ ID NO:4), and said Lp-# peptides are fragments of the Mtb protein LipC (SEQ ID NO:6), or a fragment of at least 10 residues or a conservative amino acid substitution variant, of the peptide of (a), which binds to an antibody specific for said PTRP, PE-PGRS51 or LipC protein of which said peptide is a fragment, or (b) has the formula $(P^1-X_m)_n-P^2$ wherein $P^1$ and $P^2$ are any of the peptides, fragments or variants of (a), wherein
(i) $P^1$ and $P^2$ may be the same or different and each occurrence of $P^1$ in the $P^1-X_m$ structure may be a different peptide, fragment or variant from its adjacent neighbor; and (ii) X is
(A) $C_1$-$C_5$ alkyl, $C_1$-$C_5$ alkenyl, $C_1$-$C_5$ alkynyl, $C_1$-$C_5$ polyether containing up to 4 oxygen atoms, wherein m=0 or 1, and, n=1-7; or
(B) $Gly_z$ wherein m=0 or 1, and, z=1-6, and
wherein the peptide multimer reacts with an antibody specific for the Mtb protein of which any included peptide is said fragment or said variant.

3. A peptide multimer having the formula $(P^1-Gly_z)_n-P^2$ wherein $P^1$ and $P^2$ are:
(a) any peptide selected from the group consisting of:
Pt-1 MDVALGVAVTDRVARLALVD (SEQ ID NO:7)
Pt-3 SAAPGTVIDQFVLDVAEHPV (SEQ ID NO:9)
Pt-6 DRSLAGENHRLVATRLCWPD (SEQ ID NO:12)
Pt-9 LQDSGVHDVAVISEAQAATA (SEQ ID NO:15)
Pt-13 LSVVGDPDAPPTMVAVAPVA (SEQ ID NO:19)
Pt-14 PTMVAVAPVAGADATSTVDT (SEQ ID NO:20)
Pt-20 QTPDDPTFALARGAAMAAGA (SEQ ID NO:26)
Pt-23 DATTSLPRAEAGQSGSEGEQ (SEQ ID NO:29)
Pt-34 QQAPVPPPPPDDPTAGFQGG (SEQ ID NO:40)
Pt-40 PIPVPIIIPPFPGWQPGMPT (SEQ ID NO:46)
Pt-41 FPGWQPGMPTIPTAPPTTPV (SEQ ID NO:47)
Pt-45 TTPPTTPVTTPPTTPPTTPV (SEQ ID NO:51)
Pg-2 LAAAASDVANIGSALSAANA (SEQ ID NO:62)
Pg-9 TGAGGSYALTEAANVQQNLL (SEQ ID NO:69)
Pg-14 DGGLLFGNGGAGYNSAATPG (SEQ ID NO:74)
Pg-16 MAGGNGGNAGLIGNGGTGGS (SEQ ID NO:76)
Pg-24 LTGNDGVNPAPVTNPALNGA (SEQ ID NO:84)
Pg-28 GTPGGAGVNGGNGGAGGDAN (SEQ ID NO:88)
Pg-29 GNGGAGGDANGNPANTSIAN (SEQ ID NO:89)
Pg-31 AGAGGNGAAGGDGGANGGAG (SEQ ID NO:91)
Pg-50 NGGAGGDAGHGGTGGDGGDG (SEQ ID NO:110)
Pg-51 GGTGGDGGDGGHAGTGGRGG (SEQ ID NO:111)
Pg-52 GHAGTGGRGGLLAGQHANSG (SEQ ID NO:112)
Pg-53 LLAGQHANSGNGGGGGTGGA (SEQ ID NO:113)
Pg-55 GGTHGTPGSGNAGGTGTGNA (SEQ ID NO:115)
Lp-3 ARPADYMLALSVAGGSLPVV (SEQ ID NO:121)
Lp-4 SVAGGSLPVVGKHLKPLGGV (SEQ ID NO:122)
Lp-6 TAIGVWGARHASDFLSATAK (SEQ ID NO:124)
Lp-24 IAVAGCSAGGHLSALAGLTA (SEQ ID NO:142)
Lp-26 NDPQYQAELPEGSDTSVDAV (SEQ ID NO:144)
Lp-34 GSRDCVIPVEQARSFVERLR (SEQ ID NO:152) and
Lp-39 AHAIALFLNQVHRSRAQFAK (SEQ ID NO:157), wherein said Pt-# peptides are fragments of the Mtb protein PTRP (SEQ ID NO:2), said Pg-# peptides are fragments of the Mtb protein PE-PGRS51 (SEQ ID NO:4), and said Lp-# peptides are fragments of the Mtb protein LipC (SEQ ID NO:6), or
(b) a fragment of at least 10 residues or a conservative amino acid substitution variant, of the peptide of (a), which fragment or variant binds to an antibody specific for said PTRP, PE-PGRS51 or LipC protein of which said peptide is a fragment, and wherein
(i) $P^1$ and $P^2$ may be the same or different and each occurrence of $P^1$ in the $P^1$-$Gly_z$ structure may be a different peptide, fragment or variant from its adjacent neighbor; and
(ii) n=1-100 and z=0-6, and
wherein the peptide multimer reacts with an antibody specific for the Mtb protein of which any included peptide is said fragment or said variant.

4. A kit useful for early detection of Mtb disease or infection, or an immunogenic composition useful for immunizing a subject against Mtb infection, which kit or immunogenic composition comprises:
(a) one or more peptides in a mixture or linked in a peptide multimer or fusion protein, which one or more peptides have a sequence corresponding to a fragment of an early Mtb antigen that is a Mtb cell wall protein and which peptide, peptide multimer or fusion protein is not said Mtb cell wall protein,
which early Mtb antigen is
(i) reactive with antibodies found in TB patients who are in an early stage of TB prior to the onset of sputum smear-positivity and cavitary pulmonary lesions, and
(ii) non-reactive with sera from healthy control subjects or healthy subjects with latent inactive TB,
said composition being substantially free of other Mtb proteins which are not early Mtb antigens as characterized above,
wherein said early detection is detection at a time before or after onset of constitutional symptoms of tuberculosis (TB) in the subject, but before the onset of specific symptoms identifiable as advanced TB that is distinguished from early TB by (A) smear positivity of sputum or other pulmonary associated fluid for acid-fast bacilli, (B) cavitary pulmonary lesions, or both (A) and (B), and
(b) in said kit, reagents for detection of antibodies which bind to said peptide, fragment or variant, and
(c) in said immunogenic composition,
(i) a pharmaceutically acceptable carrier, vehicle; and
(ii) an adjuvant or immunostimulant selected from the group consisting of liposomes, aluminum hydroxide, latex beads, gold beads, saponin-containing immunostimulating complex (ISCOM), complete Freund's adjuvant or incomplete Freund's adjuvant.

5. A method for the early detection of Mtb disease or infection in a subject, comprising assaying a biological fluid sample from a subject suspected of having TB for the presence of antibodies specific for
(a) a peptide selected from the group consisting of:
Pt-1 MDVALGVAVTDRVARLALVD (SEQ ID NO:7)
Pt-3 SAAPGTVIDQFVLDVAEHPV (SEQ ID NO:9)
Pt-6 DRSLAGENHRLVATRLCWPD (SEQ ID NO:12)
Pt-9 LQDSGVHDVAVISEAQAATA (SEQ ID NO:15)
Pt-13 LSVVGDPDAPPTMVAVAPVA (SEQ ID NO:19)
Pt-14 PTMVAVAPVAGADATSTVDT (SEQ ID NO:20)
Pt-20 QTPDDPTFALARGAAMAAGA (SEQ ID NO:26)
Pt-23 DATTSLPRAEAGQSGSEGEQ (SEQ ID NO:29)
Pt-34 QQAPVPPPPPDDPTAGFQGG (SEQ ID NO:40)
Pt-40 PIPVPIIIPPFPGWQPGMPT (SEQ ID NO:46)
Pt-41 FPGWQPGMPTIPTAPPTTPV (SEQ ID NO:47)
Pt-45 TTPPTTPVTTPPTTPPTTPV (SEQ ID NO:51)
Pg-2 LAAAASDVANIGSALSAANA (SEQ ID NO:62)
Pg-9 TGAGGSYALTEAANVQQNLL (SEQ ID NO:69)
Pg-14 DGGLLFGNGGAGYNSAATPG (SEQ ID NO:74)
Pg-16 MAGGNGGNAGLIGNGGTGGS (SEQ ID NO:76)
Pg-24 LTGNDGVNPAPVTNPALNGA (SEQ ID NO:84)
Pg-28 GTPGGAGVNGGNGGAGGDAN (SEQ ID NO:88)
Pg-29 GNGGAGGDANGNPANTSIAN (SEQ ID NO:89)
Pg-31 AGAGGNGAAGGDGGANGGAG (SEQ ID NO:91)
Pg-50 NGGAGGDAGHGGTGGDGGDG (SEQ ID NO:110)
Pg-51 GGTGGDGGDGGHAGTGGRGG (SEQ ID NO:111)
Pg-52 GHAGTGGRGGLLAGQHANSG (SEQ ID NO:112)
Pg-53 LLAGQHANSGNGGGGGTGGA (SEQ ID NO:113)
Pg-55 GGTHGTPGSGNAGGTGTGNA (SEQ ID NO:115)
Lp-3 ARPADYMLALSVAGGSLPVV (SEQ ID NO:121)
Lp-4 SVAGGSLPVVGKHLKPLGGV (SEQ ID NO:122)
Lp-6 TAIGVWGARHASDFLSATAK (SEQ ID NO:124)
Lp-24 IAVAGCSAGGHLSALAGLTA (SEQ ID NO:142)
Lp-26 NDPQYQAELPEGSDTSVDAV (SEQ ID NO:144)
Lp-34 GSRDCVIPVEQARSFVERLR (SEQ ID NO:152) and
Lp-39 AHAIALFLNQVHRSRAQFAK (SEQ ID NO:157),
wherein said Pt-# peptides are fragments of the *Mycobacterium tuberculosis* (Mtb) protein PTRP (SEQ ID NO:2), said Pg-# peptides are fragments of the Mtb protein PE-PGRS51 (SEQ ID NO:4), and said Lp-# peptides are fragments of the Mtb protein LipC (SEQ ID NO:6), or
(b) a fragment of at least 10 residues or a conservative amino acid substitution variant, of the peptide of (a), which binds to an antibody specific for said PTRP, PE-PGRS51 or LipC protein of which said peptide is a fragment, wherein the presence of said antibodies is indicative of the presence of said Mtb disease or infection, and
wherein said sample has been obtained from the subject before or after onset of constitutional symptoms of TB, but before the onset of specific symptoms identifiable as advanced TB that is distinguished from early TB by (A) smear positivity of sputum or other pulmonary associated fluid for acid-fast bacilli, (B) cavitary pulmonary lesions, or both (A) and (B).

6. The method of claim 5, comprising, prior to said assaying step, removing from said sample antibodies specific for cross-reactive epitopes or antigens between proteins present in *M. tuberculosis* and in other bacterial genera.

7. The method of claim 6, wherein said removing is performed by immunoadsorption of said sample with *E. coli* antigens.

8. The method of claim 5, which further comprises assaying said sample for the presence of antibodies specific for one or more additional early antigens of Mtb selected from the group consisting of:
  (a) Mtb protein GlcB encoded by Mtb gene Rv1837c;
  (b) Mtb protein MPT51 encoded by Mtb gene Rv3803c;
  (c) Mtb protein PE-PGRS36 encoded by Mtb gene Rv2098c;
  (d) Mtb protein PirG encoded by Mtb gene Rv3810;
  (e) Mtb protein Mtr encoded by Mtb gene Rv3246c;
  (f) Mtb protein antigen 85C;
  (g) Mtb glycoprotein antigen MPT32; and
  (h) a fusion protein comprising one or more of (a)-(g).

9. The method of claim 5, wherein said subject is a human.

10. The method of claim 9, wherein said subject is infected with HIV-1 or is at high risk for TB.

11. The method of claim 5, wherein said biological fluid sample is serum, urine or saliva.

12. The method of claim 5 that further comprises performing a test that detects Mtb bacilli in a sample of sputum or other body fluid of said subject.

13. A kit useful for early detection of Mtb disease or infection, or an immunogenic composition useful for immunizing a subject against Mtb infection, which kit or immunogenic composition comprises:
  (a) a peptide selected from the group consisting of:
    Pt-1 MDVALGVAVTDRVARLALVD (SEQ ID NO:7)
    Pt-3 SAAPGTVIDQFVLDVAEHPV (SEQ ID NO:9)
    Pt-6 DRSLAGENHRLVATRLCWPD (SEQ ID NO:12)
    Pt-9 LQDSGVHDVAVISEAQAATA (SEQ ID NO:15)
    Pt-13 LSVVGDPDAPPTMVAVAPVA (SEQ ID NO:19)
    Pt-14 PTMVAVAPVAGADATSTVDT (SEQ ID NO:20)
    Pt-20 QTPDDPTFALARGAAMAAGA (SEQ ID NO:26)
    Pt-23 DATTSLPRAEAGQSGSEGEQ (SEQ ID NO:29)
    Pt-34 QQAPVPPPPPDDPTAGFQGG (SEQ ID NO:40)
    Pt-40 PIPVPIIIPPFPGWQPGMPT (SEQ ID NO:46)
    Pt-41 FPGWQPGMPTIPTAPPTTPV (SEQ ID NO:47)
    Pt-45 TTPPTTPVTTPPTTPPTTPV (SEQ ID NO:51)
    Pg-2 LAAAASDVANIGSALSAANA (SEQ ID NO:62)
    Pg-9 TGAGGSYALTEAANVQQNLL (SEQ ID NO:69)
    Pg-14 DGGLLFGNGGAGYNSAATPG (SEQ ID NO:74)
    Pg-16 MAGGNGGNAGLIGNGGTGGS (SEQ ID NO:76)
    Pg-24 LTGNDGVNPAPVTNPALNGA (SEQ ID NO:84)
    Pg-28 GTPGGAGVNGGNGGAGGDAN (SEQ ID NO:88)
    Pg-29 GNGGAGGDANGNPANTSIAN (SEQ ID NO:89)
    Pg-31 AGAGGNGAAGGDGGANGGAG (SEQ ID NO:91)
    Pg-50 NGGAGGDAGHGGTGGDGGDG (SEQ ID NO:110)
    Pg-51 GGTGGDGGDGGHAGTGGRGG (SEQ ID NO:111)
    Pg-52 GHAGTGGRGGLLAGQHANSG (SEQ ID NO:112)
    Pg-53 LLAGQHANSGNGGGGGTGGA (SEQ ID NO:113)
    Pg-55 GGTHGTPGSGNAGGTGTGNA (SEQ ID NO:115)
    Lp-3 ARPADYMLALSVAGGSLPVV (SEQ ID NO:121)
    Lp-4 SVAGGSLPVVGKHLKPLGGV (SEQ ID NO:122)
    Lp-6 TAIGVWGARHASDFLSATAK (SEQ ID NO:124)
    Lp-24 IAVAGCSAGGHLSALAGLTA (SEQ ID NO:142)
    Lp-26 NDPQYQAELPEGSDTSVDAV (SEQ ID NO:144)
    Lp-34 GSRDCVIPVEQARSFVERLR (SEQ ID NO:152) and
    Lp-39 AHAIALFLNQVHRSRAQFAK (SEQ ID NO:157)
    wherein said Pt-# peptides are fragments of the Mtb protein PTRP (SEQ ID NO:2), said Pg-# peptides are fragments of the Mtb protein PE-PGRS51 (SEQ ID NO:4), and said Lp-# peptides are fragments of the Mtb protein LipC (SEQ ID NO:6), with the proviso that said peptides and said fragments of said proteins are not the full length proteins PTRP (SEQ ID NO:2), PE-PGRS51 (SEQ ID NO:4) or LipC (SEQ ID NO:6); or
  (b) a fragment of at least 10 residues or a conservative amino acid substitution variant, of the peptide of (a), which binds to an antibody specific for said PTRP, PE-PGRS51 or LipC protein of which said peptide is a fragment; and
  (c) in said kit, reagents for detection of antibodies which bind to said peptide, fragment or variant,
    wherein said early detection is detection at a time before or after onset of constitutional symptoms of tuberculosis (TB) in the subject, but before the onset of specific symptoms identifiable as advanced TB that is distinguished from early TB by (A) smear positivity of sputum or other pulmonary associated fluid for acid-fast bacilli, (B) cavitary pulmonary lesions, or both (A) and (B), and
  (d) in said immunogenic composition,
    (i) a pharmaceutically acceptable carrier, vehicle; and
    (ii) an adjuvant or immunostimulant selected from the group consisting of liposomes, aluminum hydroxide, latex beads, gold beads, ISCOM, complete Freund's adjuvant or incomplete Freund's adjuvant.

14. The kit of claim 13 further comprising one or more early Mtb antigens, which early Mtb antigens are ones that induce an antibody response in an infected subject either before or after onset of constitutional symptoms of TB, but before the onset of specific symptoms identifiable as advanced TB that is distinguished from early TB by (A) smear positivity of sputum or other pulmonary associated fluid for acid-fast bacilli, (B) cavitary pulmonary lesions, or both (A) and (B).

15. The kit of claim 14 wherein said one or more early antigens is selected from the group consisting of:
  (a) Mtb protein GlcB encoded by Mtb gene Rv1837c;
  (b) Mtb protein MPT51 encoded by Mtb gene Rv3803c;
  (c) Mtb protein PE-PGRS36 encoded by Mtb gene Rv2098c;
  (d) Mtb protein PirG encoded by Mtb gene Rv3810;
  (e) Mtb protein Mtr encoded by Mtb gene Rv3246c;

(f) Mtb protein antigen 85C;

(g) Mtb glycoprotein antigen MPT32; and (h) a fusion protein comprising one or more of (a)-(g).

16. A method for immunizing a subject against Mtb infection, comprising administering to the subject an immunogenically effective amount of the immunogenic composition of claim 13.

17. A method for immunizing a subject against Mtb infection, comprising administering to the subject an immunogenically effective amount of the fusion polypeptide of claim 1 and a pharmaceutically acceptable carrier or vehicle.

18. A method for immunizing a subject against Mtb infection, comprising administering to the subject an immunogenically effective amount of the peptide multimer of claim 3, and a pharmaceutically acceptable carrier or vehicle.

19. A method for immunizing a subject against Mtb infection, comprising administering to the subject an immunogenically effective amount of the immunogenic composition of claim 4.

20. A method for the early detection of Mtb disease or infection in a subject, comprising assaying a biological fluid sample from a subject suspected of having TB for the presence of antibodies that bind to the fusion peptide or fusion polypeptide of claim 1, wherein the presence of said antibodies is indicative of the presence of said Mtb disease or infection, wherein said sample has been obtained from the subject before or after onset of constitutional symptoms of TB, but before the onset of specific symptoms identifiable as advanced TB that is distinguished from early TB by (A) smear positivity of sputum or other pulmonary associated fluid for acid-fast bacilli, (B) cavitary pulmonary lesions, or both (A) and (B).

21. A method for the early detection of Mtb disease or infection in a subject, comprising assaying a biological fluid sample from a subject suspected of having TB for the presence of antibodies that bind to the peptide multimer of claim 2, wherein the presence of said antibodies is indicative of the presence of said Mtb disease or infection, wherein said sample has been obtained from the subject before or after onset of constitutional symptoms of TB, but before the onset of specific symptoms identifiable as advanced TB that is distinguished from early TB by (A) smear positivity of sputum or other pulmonary associated fluid for acid-fast bacilli, (B) cavitary pulmonary lesions, or both (A) and (B).

22. A method for the early detection of Mtb disease or infection in a subject, comprising assaying a biological fluid sample from a subject suspected of having TB for the presence of antibodies that bind to the peptide multimer of claim 3, wherein the presence of said antibodies is indicative of the presence of said Mtb disease or infection, wherein said sample has been obtained from the subject before or after onset of constitutional symptoms of TB, but before the onset of specific symptoms identifiable as advanced TB that is distinguished from early TB by (A) smear positivity of sputum or other pulmonary associated fluid for acid-fast bacilli, (B) cavitary pulmonary lesions, or both (A) and (B).

23. A method for the early detection of Mtb disease or infection in a subject, comprising assaying a biological fluid sample from a subject suspected of having TB for the presence of antibodies that bind to the peptide, peptide multimer or fusion polypeptide of the kit of claim 4, wherein the presence of said antibodies is indicative of the presence of said Mtb disease or infection, wherein said sample has been obtained from the subject before or after onset of constitutional symptoms of TB, but before the onset of specific symptoms identifiable as advanced TB that is distinguished from early TB by (A) smear positivity of sputum or other pulmonary associated fluid for acid-fast bacilli, (B) cavitary pulmonary lesions, or both (A) and (B).

24. A method for the early detection of Mtb disease or infection in a subject, comprising assaying a biological fluid sample from a subject suspected of having TB for the presence of antibodies that bind to the peptide, fragment or variant of the kit of claim 13, wherein the presence of said antibodies is indicative of the presence of said Mtb disease or infection, wherein said sample has been obtained from the subject before or after onset of constitutional symptoms of TB, but before the onset of specific symptoms identifiable as advanced TB that is distinguished from early TB by (A) smear positivity of sputum or other pulmonary associated fluid for acid-fast bacilli, (B) cavitary pulmonary lesions, or both (A) and (B).

25. A method for immunizing a subject against Mtb infection, comprising administering to the subject an immunogenically effective amount of the peptide multimer of claim 2 and a pharmaceutically acceptable carrier or vehicle.

26. A kit useful for early detection of Mtb disease or infection or an immunogenic composition useful for immunizing a subject against Mtb infection, which kit or immunogenic composition comprises:

(a) a mixture of two or more (i) peptides selected from the group consisting of

Pt-1 MDVALGVAVTDRVARLALVD (SEQ ID NO:7)

Pt-3 SAAPGTVIDQFVLDVAEHPV (SEQ ID NO:9)

Pt-6 DRSLAGENHRLVATRLCWPD (SEQ ID NO:12)

Pt-9 LQDSGVHDVAVISEAQAATA (SEQ ID NO:15)

Pt-13 LSVVGDPDAPPTMVAVAPVA (SEQ ID NO:19)

Pt-14 PTMVAVAPVAGADATSTVDT (SEQ ID NO:20)

Pt-20 QTPDDPTFALARGAAMAAGA (SEQ ID NO:26)

Pt-23 DATTSLPRAEAGQSGSEGEQ (SEQ ID NO:29)

Pt-34 QQAPVPPPPPDDPTAGFQGG (SEQ ID NO:40)

Pt-40 PIPVPIIIPPFPGWQPGMPT (SEQ ID NO:46)

Pt-41 FPGWQPGMPTIPTAPPTTPV (SEQ ID NO:47)

Pt-45 TTPPTTPVTTPPTTPPTTPV (SEQ ID NO:51)

Pg-2 LAAAASDVANIGSALSAANA (SEQ ID NO:62)

Pg-9 TGAGGSYALTEAANVQQNLL (SEQ ID NO:69)

Pg-14 DGGLLFGNGGAGYNSAATPG (SEQ ID NO:74)

Pg-16 MAGGNGGNAGLIGNGGTGGS (SEQ ID NO:76)

Pg-24 LTGNDGVNPAPVTNPALNGA (SEQ ID NO:84)

Pg-28 GTPGGAGVNGGNGGAGGDAN (SEQ ID NO:88)

Pg-29 GNGGAGGDANGNPANTSIAN (SEQ ID NO:89)

Pg-31 AGAGGNGAAGGDGGANGGAG (SEQ ID NO:91)
Pg-50 NGGAGGDAGHGGTGGDGGDG (SEQ ID NO:110)
Pg-51 GGTGGDGGDGGHAGTGGRGG (SEQ ID NO:111)
Pg-52 GHAGTGGRGGLLAGQHANSG (SEQ ID NO:112)
Pg-53 LLAGQHANSGNGGGGGTGGA (SEQ ID NO:113)
Pg-55 GGTHGTPGSGNAGGTGTGNA (SEQ ID NO:115)
Lp-3 ARPADYMLALSVAGGSLPVV (SEQ ID NO:121)
Lp-4 SVAGGSLPVVGKHLKPLGGV (SEQ ID NO:122)
Lp-6 TAIGVWGARHASDFLSATAK (SEQ ID NO:124)
Lp-24 IAVAGCSAGGHLSALAGLTA (SEQ ID NO:142)
Lp-26 NDPQYQAELPEGSDTSVDAV (SEQ ID NO:144)
Lp-34 GSRDCVIPVEQARSFVERLR (SEQ ID NO:152) and
Lp-39 AHAIALFLNQVHRSRAQFAK (SEQ ID NO:157), or
wherein said Pt# peptides are fragments of the Mtb protein PTRP (SEQ ID NO:2), said Pg-# peptides are fragments of the Mtb protein PE-PGRS51 (SEQ ID NO:4), and said Lp-# peptides are fragments of the Mtb protein LipC (SEQ ID NO:6), or
(ii) fragment of at least 10 residues or a conservative amino acid substitution variant, of the peptide, which fragment or variant binds to an antibody specific for said PTRP, PE-PGRS51 or LipC protein of which said peptide is a fragment, or (b) a fusion peptide or fusion polypeptide of said two or more peptides, fragments or variants of (a)(i) and (a)(ii), wherein said early detection is detection at a time before or after onset of constitutional symptoms of tuberculosis (TB) in the subject, but before the onset of specific symptoms identifiable as advanced TB that is distinguished from early TB by (A) smear positivity of sputum or other pulmonary associated fluid for acid-fast bacilli, (B) cavitary pulmonary lesions, or both (A) and (B),
(c) said kit further comprises reagents for detection of antibodies which bind to said peptide, fragment or variant, and
(d) said immunogenic composition further comprises,
(i) a pharmaceutically acceptable carrier or vehicle; and
(ii) an adjuvant or immunostimulant selected from the group consisting of liposomes, aluminum hydroxide, latex beads, gold beads, ISCOM, complete Freund's adjuvant or incomplete Freund's adjuvant.

27. A method for the early detection of Mtb disease or infection in a subject, comprising assaying a biological fluid sample from a subject suspected of having TB for the presence of antibodies specific for the peptide or fusion polypeptide of the kit of claim 26, wherein the presence of said antibodies is indicative of the presence of said Mtb disease or infection, and
wherein said sample has been obtained from the subject before or after onset of constitutional symptoms of TB, but before the onset of specific symptoms identifiable as advanced TB that is distinguished from early TB by (a) smear positivity of sputum or other pulmonary associated fluid for acid-fast bacilli, (b) cavitary pulmonary lesions, or both (a) and (b).

28. A method for immunizing a subject against Mtb infection, comprising administering to the subject an immunogenically effective amount of the immunogenic composition of claim 26.

* * * * *

SEQUENCE LISTING

```
<160> NUMBER OF SEQ ID NOS: 175

<210> SEQ ID NO 1
<211> LENGTH: 1647
<212> TYPE: DNA
<213> ORGANISM: Mycobacterium tuberculosis Strain H37Rv
<220> FEATURE:
<221> NAME/KEY: CDS
<222> LOCATION: (1)..(1644)

<400> SEQUENCE: 1 atg gac gtc gct ttg ggg gtt gcg gtc acg gat cgg gtc gcg cgt ctg      48
Met Asp Val Ala Leu Gly Val Ala Val Thr Asp Arg Val Ala Arg Leu
```

|  |  |
|---|---|
| gcg ctg gtc gac tcg gct gcg ccc ggc acc gtg atc gac cag ttc gtg<br>Ala Leu Val Asp Ser Ala Ala Pro Gly Thr Val Ile Asp Gln Phe Val<br>20                       25                           30 | 96 |
| ctc gat gtg gcc gag cac ccg gtc gag gtg tta acc gag acc gtg gtg<br>Leu Asp Val Ala Glu His Pro Val Glu Val Leu Thr Glu Thr Val Val<br>35                       40                      45 | 144 |
| ggc acg gat cgg tca ttg gcc ggc gaa aac cac cgg ctg gtc gct acc<br>Gly Thr Asp Arg Ser Leu Ala Gly Glu Asn His Arg Leu Val Ala Thr<br>50                       55                       60 | 192 |
| cgg ctg tgt tgg ccg gat cag gcc aaa gct gac gag ctg cag cac gca<br>Arg Leu Cys Trp Pro Asp Gln Ala Lys Ala Asp Glu Leu Gln His Ala<br>65                       70                      75                      80 | 240 |
| ctg cag gac tcc ggg gtc cac gac gtt gcc gtg ata tcc gag gcg cag<br>Leu Gln Asp Ser Gly Val His Asp Val Ala Val Ile Ser Glu Ala Gln<br>                    85                      90                      95 | 288 |
| gcc gcc acg gcg ctg gtc ggg gcg gca cat gcc ggc tct gcc gtg ctg<br>Ala Ala Thr Ala Leu Val Gly Ala Ala His Ala Gly Ser Ala Val Leu<br>                    100                   105                 110 | 336 |
| ttg gtg ggt gat gag acg gca acc tta tcg gtg gtt ggt gac ccg gac<br>Leu Val Gly Asp Glu Thr Ala Thr Leu Ser Val Val Gly Asp Pro Asp<br>115                    120                   125 | 384 |
| gcg ccg ccg acg atg gtg gcc gtc gcg ccg gtg gcg ggc gcc gac gcc<br>Ala Pro Pro Thr Met Val Ala Val Ala Pro Val Ala Gly Ala Asp Ala<br>130                    135                   140 | 432 |
| aca tcg acc gtc gat acc ctg atg gcc cgg ctc ggc gac cag gcc ctc<br>Thr Ser Thr Val Asp Thr Leu Met Ala Arg Leu Gly Asp Gln Ala Leu<br>145                    150                   155                 160 | 480 |
| gcc ccg ggg gat gtc ttc ctg gtg ggt agg tcc gcc gag cac acc acg<br>Ala Pro Gly Asp Val Phe Leu Val Gly Arg Ser Ala Glu His Thr Thr<br>                    165                   170                 175 | 528 |
| gtt ctt gcc gac cag ctg cgc gcg gcg tcg acg atg cgc gtg cag act<br>Val Leu Ala Asp Gln Leu Arg Ala Ala Ser Thr Met Arg Val Gln Thr<br>                    180                   185                 190 | 576 |
| ccc gac gac ccc acg ttc gcg ctg gcc cgt ggc gcg gcg atg gcg gcc<br>Pro Asp Asp Pro Thr Phe Ala Leu Ala Arg Gly Ala Ala Met Ala Ala<br>                    195                   200                 205 | 624 |
| ggc gcc gct acg atg gcg cac ccg gcc ctg gtc gcg gat gcg acc act<br>Gly Ala Ala Thr Met Ala His Pro Ala Leu Val Ala Asp Ala Thr Thr<br>210                    215                   220 | 672 |
| tcg ctc ccc cgg gcc gag gcg ggg caa tcg ggt tct gaa ggc gag cag<br>Ser Leu Pro Arg Ala Glu Ala Gly Gln Ser Gly Ser Glu Gly Glu Gln<br>225                    230                   235                 240 | 720 |
| ctg gcg tac tcg cag gcc agc gat tac gag ctg ctt ccg gtc gac gaa<br>Leu Ala Tyr Ser Gln Ala Ser Asp Tyr Glu Leu Leu Pro Val Asp Glu<br>                    245                   250                 255 | 768 |
| tat gag gaa cac gac gaa tac ggg gca gcc gcg gat cgc tcg gcg ccg<br>Tyr Glu Glu His Asp Glu Tyr Gly Ala Ala Ala Asp Arg Ser Ala Pro<br>                    260                   265                 270 | 816 |
| ttg agc cga cgg tcg ctg ctg atc ggc aac gct gtc gtg gcc ttt gcg<br>Leu Ser Arg Arg Ser Leu Leu Ile Gly Asn Ala Val Val Ala Phe Ala<br>275                    280                   285 | 864 |
| gtg atc ggt ttc gcc tcg ctg gcg gtg gcg gtg gcg gtc acc atc cga<br>Val Ile Gly Phe Ala Ser Leu Ala Val Ala Val Ala Val Thr Ile Arg<br>290                    295                   300 | 912 |
| ccg acc gcg gcc tca aaa ccg gta gag gga cac caa aac gcc cag cca<br>Pro Thr Ala Ala Ser Lys Pro Val Glu Gly His Gln Asn Ala Gln Pro<br>305                    310                   315                 320 | 960 |
| ggg aag ttc atg ccg ttg ttg ccg acg caa cag cag gcg ccg gtc ccg | 1008 |

```
Gly Lys Phe Met Pro Leu Leu Pro Thr Gln Gln Ala Pro Val Pro
            325                 330                 335 ccg cct ccg ccc gat gat ccc acc gct gga ttc cag ggc ggc acc att     1056
Pro Pro Pro Pro Asp Asp Pro Thr Ala Gly Phe Gln Gly Gly Thr Ile
            340                 345                 350 ccg gct gta cag aac gtg gtg ccg cgg ccg ggt acc tca ccc ggg gtg     1104
Pro Ala Val Gln Asn Val Val Pro Arg Pro Gly Thr Ser Pro Gly Val
            355                 360                 365 ggt ggg acg ccg gct tcg cct gcg ccg gaa gcg ccg gcc gtg ccc ggt     1152
Gly Gly Thr Pro Ala Ser Pro Ala Pro Glu Ala Pro Ala Val Pro Gly
            370                 375                 380 gtt gtg cct gcc ccg gtg cca atc ccg gtc ccg atc atc att ccc ccg     1200
Val Val Pro Ala Pro Val Pro Ile Pro Val Pro Ile Ile Ile Pro Pro
385                 390                 395                 400 ttc ccg ggt tgg cag cct gga atg cca acc atc ccc acc gca ccg ccg     1248
Phe Pro Gly Trp Gln Pro Gly Met Pro Thr Ile Pro Thr Ala Pro Pro
                405                 410                 415 acg acg ccg gtg acc acg tcg gcg acg acg ccg ccg acc acg ccg ccg     1296
Thr Thr Pro Val Thr Thr Ser Ala Thr Thr Pro Pro Thr Thr Pro Pro
            420                 425                 430 acc acg ccg gtg acc acg ccg cca acg acg ccg ccg acc acg ccg gtg     1344
Thr Thr Pro Val Thr Thr Pro Pro Thr Thr Pro Pro Thr Thr Pro Val
            435                 440                 445 acc acg ccg cca acg acg ccg ccg acc acg ccg gtg acc acg cca cca     1392
Thr Thr Pro Pro Thr Thr Pro Pro Thr Thr Pro Val Thr Thr Pro Pro
450                 455                 460 acg acc gtc gcc ccg acg acc gtc gcc ccg acg acg gtc gct ccg acc     1440
Thr Thr Val Ala Pro Thr Thr Val Ala Pro Thr Thr Val Ala Pro Thr
465                 470                 475                 480 acc gtc gcc ccg acc acg gtc gct cca gcc acc gcc acg ccg acg acc     1488
Thr Val Ala Pro Thr Thr Val Ala Pro Ala Thr Ala Thr Pro Thr Thr
                485                 490                 495 gtc gct ccg cag ccg acg cag cag ccc acg caa caa cca acc caa cag     1536
Val Ala Pro Gln Pro Thr Gln Gln Pro Thr Gln Gln Pro Thr Gln Gln
            500                 505                 510 atg cca acc cag cag cag acc gtg gcc ccg cag acg gtg gcg ccg gct     1584
Met Pro Thr Gln Gln Gln Thr Val Ala Pro Gln Thr Val Ala Pro Ala
            515                 520                 525 ccg cag ccg ccg tcc ggt ggc cgc aac ggc agc ggc ggg ggc gac tta     1632
Pro Gln Pro Pro Ser Gly Gly Arg Asn Gly Ser Gly Gly Gly Asp Leu
            530                 535                 540 ttc ggc ggg ttc tga                                                 1647
Phe Gly Gly Phe
545

<210> SEQ ID NO 2
<211> LENGTH: 548
<212> TYPE: PRT
<213> ORGANISM: Mycobacterium tuberculosis Strain H37Rv

<400> SEQUENCE: 2

Met Asp Val Ala Leu Gly Val Ala Val Thr Asp Arg Val Ala Arg Leu
1               5                   10                  15

Ala Leu Val Asp Ser Ala Ala Pro Gly Thr Val Ile Asp Gln Phe Val
            20                  25                  30

Leu Asp Val Ala Glu His Pro Val Glu Val Leu Thr Glu Thr Val Val
        35                  40                  45

Gly Thr Asp Arg Ser Leu Ala Gly Glu Asn His Arg Leu Val Ala Thr
    50                  55                  60
```

```
Arg Leu Cys Trp Pro Asp Gln Ala Lys Ala Asp Glu Leu Gln His Ala
 65                  70                  75                  80

Leu Gln Asp Ser Gly Val His Asp Val Ala Val Ile Ser Glu Ala Gln
             85                  90                  95

Ala Ala Thr Ala Leu Val Gly Ala Ala His Ala Gly Ser Ala Val Leu
        100                 105                 110

Leu Val Gly Asp Glu Thr Ala Thr Leu Ser Val Val Gly Asp Pro Asp
    115                 120                 125

Ala Pro Pro Thr Met Val Ala Val Ala Pro Val Gly Ala Asp Ala
130                 135                 140

Thr Ser Thr Val Asp Thr Leu Met Ala Arg Leu Gly Asp Gln Ala Leu
145                 150                 155                 160

Ala Pro Gly Asp Val Phe Leu Val Gly Arg Ser Ala Glu His Thr Thr
                165                 170                 175

Val Leu Ala Asp Gln Leu Arg Ala Ala Ser Thr Met Arg Val Gln Thr
            180                 185                 190

Pro Asp Asp Pro Thr Phe Ala Leu Ala Arg Gly Ala Ala Met Ala Ala
        195                 200                 205

Gly Ala Ala Thr Met Ala His Pro Ala Leu Val Ala Asp Ala Thr Thr
    210                 215                 220

Ser Leu Pro Arg Ala Glu Ala Gly Gln Ser Gly Ser Glu Gly Glu Gln
225                 230                 235                 240

Leu Ala Tyr Ser Gln Ala Ser Asp Tyr Glu Leu Leu Pro Val Asp Glu
                245                 250                 255

Tyr Glu Glu His Asp Glu Tyr Gly Ala Ala Ala Asp Arg Ser Ala Pro
            260                 265                 270

Leu Ser Arg Arg Ser Leu Leu Ile Gly Asn Ala Val Val Ala Phe Ala
        275                 280                 285

Val Ile Gly Phe Ala Ser Leu Ala Val Ala Val Ala Val Thr Ile Arg
    290                 295                 300

Pro Thr Ala Ala Ser Lys Pro Val Glu Gly His Gln Asn Ala Gln Pro
305                 310                 315                 320

Gly Lys Phe Met Pro Leu Leu Pro Thr Gln Gln Gln Ala Pro Val Pro
                325                 330                 335

Pro Pro Pro Pro Asp Asp Pro Thr Ala Gly Phe Gln Gly Gly Thr Ile
            340                 345                 350

Pro Ala Val Gln Asn Val Val Pro Arg Pro Gly Thr Ser Pro Gly Val
        355                 360                 365

Gly Gly Thr Pro Ala Ser Pro Ala Pro Glu Ala Pro Ala Val Pro Gly
    370                 375                 380

Val Val Pro Ala Pro Val Pro Ile Pro Val Pro Ile Ile Pro Pro
385                 390                 395                 400

Phe Pro Gly Trp Gln Pro Gly Met Pro Thr Ile Pro Thr Ala Pro Pro
                405                 410                 415

Thr Thr Pro Val Thr Thr Ser Ala Thr Thr Pro Thr Thr Pro Pro
            420                 425                 430

Thr Thr Pro Val Thr Thr Pro Pro Thr Thr Pro Thr Thr Pro Val
        435                 440                 445

Thr Thr Pro Pro Thr Thr Pro Pro Thr Thr Pro Val Thr Thr Pro Pro
    450                 455                 460

Thr Thr Val Ala Pro Thr Thr Val Ala Pro Thr Thr Val Ala Pro Thr
465                 470                 475                 480

Thr Val Ala Pro Thr Thr Val Ala Pro Ala Thr Ala Thr Pro Thr Thr
```

```
                    485                 490                 495
Val Ala Pro Gln Pro Thr Gln Gln Pro Thr Gln Gln Pro Thr Gln
            500                 505                 510

Met Pro Thr Gln Gln Thr Val Ala Pro Gln Thr Val Ala Pro Ala
        515                 520                 525

Pro Gln Pro Pro Ser Gly Gly Arg Asn Gly Ser Gly Gly Asp Leu
    530                 535                 540

Phe Gly Gly Phe
545

<210> SEQ ID NO 3
<211> LENGTH: 1767
<212> TYPE: DNA
<213> ORGANISM: Mycobacterium tuberculosis Strain H37Rv
<220> FEATURE:
<221> NAME/KEY: CDS
<222> LOCATION: (1)..(1764)

<400> SEQUENCE: 3
```

| | | | | | | | | | | | | | | | | |
|---|---|---|---|---|---|---|---|---|---|---|---|---|---|---|---|---|
| atg | tcg | ttt | gtc | gta | gca | gtc | ccg | gag | gca | ttg | gcg | gcg | gcc | gcg | tcg | 48 |
| Met | Ser | Phe | Val | Val | Ala | Val | Pro | Glu | Ala | Leu | Ala | Ala | Ala | Ala | Ser | |
| 1 | | | | 5 | | | | | 10 | | | | | 15 | | |
| gat | gtg | gcg | aac | atc | ggt | tct | gcg | cta | agt | gcc | gcg | aat | gca | gcg | gca | 96 |
| Asp | Val | Ala | Asn | Ile | Gly | Ser | Ala | Leu | Ser | Ala | Ala | Asn | Ala | Ala | Ala | |
| | | | 20 | | | | | 25 | | | | | 30 | | | |
| gcc | gcc | ggc | aca | acg | ggg | cta | ctg | gca | gcc | ggt | gcc | gac | gag | gtc | tcg | 144 |
| Ala | Ala | Gly | Thr | Thr | Gly | Leu | Leu | Ala | Ala | Gly | Ala | Asp | Glu | Val | Ser | |
| | | 35 | | | | | 40 | | | | | 45 | | | | |
| gcc | gcc | ctg | gcg | tcg | ctg | ttt | tcc | ggg | cac | gct | gtg | agc | tac | caa | cag | 192 |
| Ala | Ala | Leu | Ala | Ser | Leu | Phe | Ser | Gly | His | Ala | Val | Ser | Tyr | Gln | Gln | |
| | 50 | | | | | 55 | | | | | 60 | | | | | |
| gtc | gcg | gcc | cag | gcg | acg | gcg | tta | cac | gat | cag | ttt | gtc | cag | gcc | ttg | 240 |
| Val | Ala | Ala | Gln | Ala | Thr | Ala | Leu | His | Asp | Gln | Phe | Val | Gln | Ala | Leu | |
| 65 | | | | | 70 | | | | | 75 | | | | | 80 | |
| acc | ggt | gcc | ggc | gga | tcg | tac | gcc | ctc | acc | gag | gcc | gcc | aac | gtc | cag | 288 |
| Thr | Gly | Ala | Gly | Gly | Ser | Tyr | Ala | Leu | Thr | Glu | Ala | Ala | Asn | Val | Gln | |
| | | | | 85 | | | | | 90 | | | | | 95 | | |
| cag | aat | ctg | ctg | aac | gca | att | aac | gcg | ccc | act | cag | gcg | ctg | ttg | ggg | 336 |
| Gln | Asn | Leu | Leu | Asn | Ala | Ile | Asn | Ala | Pro | Thr | Gln | Ala | Leu | Leu | Gly | |
| | | | 100 | | | | | 105 | | | | | 110 | | | |
| cgc | ccg | tta | att | ggc | gac | ggg | gct | gtc | ggc | acc | gcc | agc | agc | ccc | gac | 384 |
| Arg | Pro | Leu | Ile | Gly | Asp | Gly | Ala | Val | Gly | Thr | Ala | Ser | Ser | Pro | Asp | |
| | | | 115 | | | | | 120 | | | | | 125 | | | |
| ggg | caa | gat | ggc | ggt | ctg | ctg | ttc | ggc | aac | ggg | ggc | gcc | ggc | tac | aac | 432 |
| Gly | Gln | Asp | Gly | Gly | Leu | Leu | Phe | Gly | Asn | Gly | Gly | Ala | Gly | Tyr | Asn | |
| | 130 | | | | | 135 | | | | | 140 | | | | | |
| agc | gcc | gcc | acg | ccc | gga | atg | gcc | ggc | ggc | aac | ggc | ggc | aac | gcc | gga | 480 |
| Ser | Ala | Ala | Thr | Pro | Gly | Met | Ala | Gly | Gly | Asn | Gly | Gly | Asn | Ala | Gly | |
| 145 | | | | | 150 | | | | | 155 | | | | | 160 | |
| ttg | atc | ggc | aac | ggc | ggt | act | ggc | ggg | tcg | ggc | ggt | gcc | ggc | gcg | gcc | 528 |
| Leu | Ile | Gly | Asn | Gly | Gly | Thr | Gly | Gly | Ser | Gly | Gly | Ala | Gly | Ala | Ala | |
| | | | | 165 | | | | | 170 | | | | | 175 | | |
| ggt | ggc | gcc | ggc | ggc | agc | ggc | ggc | tgg | ttg | tac | ggc | aac | ggc | gga | aac | 576 |
| Gly | Gly | Ala | Gly | Gly | Ser | Gly | Gly | Trp | Leu | Tyr | Gly | Asn | Gly | Gly | Asn | |
| | | | 180 | | | | | 185 | | | | | 190 | | | |
| ggc | ggc | atc | ggc | ggg | aat | gcg | atc | gtc | gcg | ggc | ggt | gcc | ggc | ggc | aat | 624 |
| Gly | Gly | Ile | Gly | Gly | Asn | Ala | Ile | Val | Ala | Gly | Gly | Ala | Gly | Gly | Asn | |
| | | | 195 | | | | | 200 | | | | | 205 | | | |
| ggg | ggc | gct | ggc | ggc | gcc | gcc | gga | ttg | tgg | ggc | agt | ggc | ggc | agc | ggc | 672 |
| Gly | Gly | Ala | Gly | Gly | Ala | Ala | Gly | Leu | Trp | Gly | Ser | Gly | Gly | Ser | Gly | |

-continued

```
              210                 215                 220
ggc caa ggc ggc aac ggt ctg acc ggc aac gac ggc gtg aat ccg gcc    720
Gly Gln Gly Gly Asn Gly Leu Thr Gly Asn Asp Gly Val Asn Pro Ala
225                 230                 235                 240 ccc gtc aca aac ccc gcg cta aat ggc gcc gcc ggc gac agc aat atc    768
Pro Val Thr Asn Pro Ala Leu Asn Gly Ala Ala Gly Asp Ser Asn Ile
                245                 250                 255 gag ccg caa acc agc gtc ctg atc ggc acc caa ggc ggt gac ggc acg    816
Glu Pro Gln Thr Ser Val Leu Ile Gly Thr Gln Gly Gly Asp Gly Thr
            260                 265                 270 ccc ggg ggt gct ggc gtc aac ggc ggc aac ggt ggc gcg ggc gga gac    864
Pro Gly Gly Ala Gly Val Asn Gly Gly Asn Gly Gly Ala Gly Gly Asp
        275                 280                 285 gcc aat ggc aac ccc gca aac acc tcg atc gcc aac gca ggc gcc ggc    912
Ala Asn Gly Asn Pro Ala Asn Thr Ser Ile Ala Asn Ala Gly Ala Gly
290                 295                 300 ggg aac ggc gcc gcc ggc ggt gac ggc ggt gcc aat ggc ggt gcg ggc    960
Gly Asn Gly Ala Ala Gly Gly Asp Gly Gly Ala Asn Gly Gly Ala Gly
305                 310                 315                 320 ggc gcc ggc ggg cag gcc gcg tcc gcc ggt agt tcc gtc ggc ggt gac   1008
Gly Ala Gly Gly Gln Ala Ala Ser Ala Gly Ser Ser Val Gly Gly Asp
                325                 330                 335 ggc ggc aac ggc ggt gcc ggc ggt acg ggc acg aac ggg cac gcc ggc   1056
Gly Gly Asn Gly Gly Ala Gly Gly Thr Gly Thr Asn Gly His Ala Gly
            340                 345                 350 ggt gcg ggc ggc gcc ggc ggt gcc ggt ggt cgc ggc ggg tgg ctg gtc   1104
Gly Ala Gly Gly Ala Gly Gly Ala Gly Gly Arg Gly Gly Trp Leu Val
        355                 360                 365 ggc aac ggt ggc aac ggt ggc aac ggt gcc gcc ggc ggc aac ggc gcc   1152
Gly Asn Gly Gly Asn Gly Gly Asn Gly Ala Ala Gly Gly Asn Gly Ala
370                 375                 380 atc ggc ggt acc ggt ggt gcc ggc ggc gtc ccc gcc aac cag ggc ggt   1200
Ile Gly Gly Thr Gly Gly Ala Gly Gly Val Pro Ala Asn Gln Gly Gly
385                 390                 395                 400 aac agc gcc cta ggc acc cag ccg gtc ggc ggc gac ggc ggc gac ggc   1248
Asn Ser Ala Leu Gly Thr Gln Pro Val Gly Gly Asp Gly Gly Asp Gly
                405                 410                 415 ggc aac ggg ggc acc gga ggc acc ggc ggg cgt ggc ggc gac ggc gga   1296
Gly Asn Gly Gly Thr Gly Gly Thr Gly Gly Arg Gly Gly Asp Gly Gly
            420                 425                 430 tcc ggc ggc gcg ggc ggc gcg agc ggt tgg ttg atg ggc aac ggc ggc   1344
Ser Gly Gly Ala Gly Gly Ala Ser Gly Trp Leu Met Gly Asn Gly Gly
        435                 440                 445 aac ggc ggc aac ggc ggc acc ggc ggc tca ggc ggt gtc ggc ggc aat   1392
Asn Gly Gly Asn Gly Gly Thr Gly Gly Ser Gly Gly Val Gly Gly Asn
450                 455                 460 ggc ggc atc ggc ggt gac ggc gcc ggc gga aac gcc acg agc acg        1440
Gly Gly Ile Gly Gly Asp Gly Ala Gly Gly Asn Ala Thr Ser Thr
465                 470                 475                 480 tcg agc atc ccc ttc gac gcc cac ggg ggt aac ggc ggc gct ggt ggc   1488
Ser Ser Ile Pro Phe Asp Ala His Gly Gly Asn Gly Gly Ala Gly Gly
                485                 490                 495 gac gct ggt cac ggc gga acg ggc ggc gac ggc ggt gac ggg ggg cat   1536
Asp Ala Gly His Gly Gly Thr Gly Gly Asp Gly Gly Asp Gly Gly His
            500                 505                 510 gcc ggc acc ggt gga cgt ggc ggg tta ctg gcc ggc cag cac gcc aac   1584
Ala Gly Thr Gly Gly Arg Gly Gly Leu Leu Ala Gly Gln His Ala Asn
        515                 520                 525 tcc ggc aat ggc ggt ggc ggc ggt acc ggc ggt gcc ggg ggc acc cat   1632
```

-continued

```
Ser Gly Asn Gly Gly Gly Gly Thr Gly Ala Gly Gly Thr His
    530                 535                 540 ggc acc ccc ggc agc ggc aac gca ggc ggc acc ggc acc ggt aac gct         1680
Gly Thr Pro Gly Ser Gly Asn Ala Gly Gly Thr Gly Thr Gly Asn Ala
545                 550                 555                 560 gac agc aca aac ggc ggg cca ggc agc gac ggc ctc ggc ggg gac gcg         1728
Asp Ser Thr Asn Gly Gly Pro Gly Ser Asp Gly Leu Gly Gly Asp Ala
                565                 570                 575 ttt aac ggc agt cgc ggc acc gac ggc aac ccc ggc taa                     1767
Phe Asn Gly Ser Arg Gly Thr Asp Gly Asn Pro Gly
                580                 585

<210> SEQ ID NO 4
<211> LENGTH: 588
<212> TYPE: PRT
<213> ORGANISM: Mycobacterium tuberculosis Strain H37Rv

<400> SEQUENCE: 4

Met Ser Phe Val Val Ala Val Pro Glu Ala Leu Ala Ala Ala Ala Ser
1               5                   10                  15

Asp Val Ala Asn Ile Gly Ser Ala Leu Ser Ala Ala Asn Ala Ala Ala
                20                  25                  30

Ala Ala Gly Thr Thr Gly Leu Leu Ala Ala Gly Ala Asp Glu Val Ser
            35                  40                  45

Ala Ala Leu Ala Ser Leu Phe Ser Gly His Ala Val Ser Tyr Gln Gln
50                  55                  60

Val Ala Ala Gln Ala Thr Ala Leu His Asp Gln Phe Val Gln Ala Leu
65                  70                  75                  80

Thr Gly Ala Gly Gly Ser Tyr Ala Leu Thr Glu Ala Ala Asn Val Gln
                85                  90                  95

Gln Asn Leu Leu Asn Ala Ile Asn Ala Pro Thr Gln Ala Leu Leu Gly
                100                 105                 110

Arg Pro Leu Ile Gly Asp Gly Ala Val Gly Thr Ala Ser Ser Pro Asp
            115                 120                 125

Gly Gln Asp Gly Gly Leu Leu Phe Gly Asn Gly Gly Ala Gly Tyr Asn
130                 135                 140

Ser Ala Ala Thr Pro Gly Met Ala Gly Gly Asn Gly Asn Ala Gly
145                 150                 155                 160

Leu Ile Gly Asn Gly Gly Thr Gly Gly Ser Gly Gly Ala Gly Ala Ala
                165                 170                 175

Gly Gly Ala Gly Gly Ser Gly Gly Trp Leu Tyr Gly Asn Gly Gly Asn
            180                 185                 190

Gly Gly Ile Gly Gly Asn Ala Ile Val Ala Gly Gly Ala Gly Gly Asn
            195                 200                 205

Gly Gly Ala Gly Gly Ala Gly Leu Trp Gly Ser Gly Gly Ser Gly
        210                 215                 220

Gly Gln Gly Gly Asn Gly Leu Thr Gly Asn Asp Gly Val Asn Pro Ala
225                 230                 235                 240

Pro Val Thr Asn Pro Ala Leu Asn Gly Ala Ala Gly Asp Ser Asn Ile
                245                 250                 255

Glu Pro Gln Thr Ser Val Leu Ile Gly Thr Gln Gly Gly Asp Gly Thr
                260                 265                 270

Pro Gly Gly Ala Gly Val Asn Gly Gly Asn Gly Gly Ala Gly Gly Asp
            275                 280                 285

Ala Asn Gly Asn Pro Ala Asn Thr Ser Ile Ala Asn Ala Gly Ala Gly
        290                 295                 300
```

-continued

```
Gly Asn Gly Ala Ala Gly Gly Asp Gly Gly Ala Asn Gly Gly Ala Gly
305                 310                 315                 320

Gly Ala Gly Gly Gln Ala Ala Ser Ala Gly Ser Ser Val Gly Gly Asp
                325                 330                 335

Gly Gly Asn Gly Gly Ala Gly Gly Thr Gly Thr Asn Gly His Ala Gly
            340                 345                 350

Gly Ala Gly Gly Ala Gly Gly Ala Gly Gly Arg Gly Gly Trp Leu Val
        355                 360                 365

Gly Asn Gly Gly Asn Gly Gly Asn Gly Ala Ala Gly Gly Asn Gly Ala
    370                 375                 380

Ile Gly Gly Thr Gly Gly Ala Gly Gly Val Pro Ala Asn Gln Gly Gly
385                 390                 395                 400

Asn Ser Ala Leu Gly Thr Gln Pro Val Gly Gly Asp Gly Gly Asp Gly
                405                 410                 415

Gly Asn Gly Gly Thr Gly Gly Thr Gly Gly Arg Gly Gly Asp Gly Gly
            420                 425                 430

Ser Gly Gly Ala Gly Gly Ala Ser Gly Trp Leu Met Gly Asn Gly Gly
        435                 440                 445

Asn Gly Gly Asn Gly Gly Thr Gly Gly Ser Gly Gly Val Gly Gly Asn
    450                 455                 460

Gly Gly Ile Gly Gly Asp Gly Ala Gly Gly Asn Ala Thr Ser Thr
465                 470                 475                 480

Ser Ser Ile Pro Phe Asp Ala His Gly Asn Gly Gly Ala Gly Gly
                485                 490                 495

Asp Ala Gly His Gly Gly Thr Gly Asp Gly Gly Asp Gly Gly His
            500                 505                 510

Ala Gly Thr Gly Gly Arg Gly Gly Leu Leu Ala Gly Gln His Ala Asn
        515                 520                 525

Ser Gly Asn Gly Gly Gly Gly Thr Gly Gly Ala Gly Gly Thr His
    530                 535                 540

Gly Thr Pro Gly Ser Gly Asn Ala Gly Gly Thr Gly Thr Gly Asn Ala
545                 550                 555                 560

Asp Ser Thr Asn Gly Gly Pro Gly Ser Asp Gly Leu Gly Gly Asp Ala
                565                 570                 575

Phe Asn Gly Ser Arg Gly Thr Asp Gly Asn Pro Gly
            580                 585
```

<210> SEQ ID NO 5
<211> LENGTH: 1212
<212> TYPE: DNA
<213> ORGANISM: Mycbacterium tuberculosis Strain H37Rv
<220> FEATURE:
<221> NAME/KEY: CDS
<222> LOCATION: (1)..(1212)

<400> SEQUENCE: 5

```
atg aac cag cga cgc gcc gcc ggg tca acc ggt gtg gcc tac atc aga      48
Met Asn Gln Arg Arg Ala Ala Gly Ser Thr Gly Val Ala Tyr Ile Arg
1               5                   10                  15 tgg ttg cta cgt gcc cgt ccc gct gac tat atg ctg gcc ttg agt gtc      96
Trp Leu Leu Arg Ala Arg Pro Ala Asp Tyr Met Leu Ala Leu Ser Val
            20                  25                  30 gcc ggg ggt tcg cta ccg gtg gtg ggt aag cac ctc aag ccg ctc ggc     144
Ala Gly Gly Ser Leu Pro Val Val Gly Lys His Leu Lys Pro Leu Gly
        35                  40                  45 ggc gtt act gcc atc ggc gtc tgg ggc gcc cgg cac gca tcc gat ttc     192
Gly Val Thr Ala Ile Gly Val Trp Gly Ala Arg His Ala Ser Asp Phe
```

```
Gly Val Thr Ala Ile Gly Val Trp Gly Ala Arg His Ala Ser Asp Phe
    50              55                  60 ttg tcc gcg acg gcg aag gat tta ctg acc ccc ggt atc aac gag gtt     240
Leu Ser Ala Thr Ala Lys Asp Leu Leu Thr Pro Gly Ile Asn Glu Val
65              70                  75                  80 cgt cgt cga gat cgt gcc agc acg cag gag gtt tcc gtc gcg gcc tta     288
Arg Arg Arg Asp Arg Ala Ser Thr Gln Glu Val Ser Val Ala Ala Leu
                85                  90                  95 cgc ggc atc gtt tcg ccc gac gac ctt gcc gtc gaa tgg ccg gcg ccg     336
Arg Gly Ile Val Ser Pro Asp Asp Leu Ala Val Glu Trp Pro Ala Pro
            100                 105                 110 gag cgc acg ccg ccg gtc tgc ggg gcg ctg cgc cac cgc cgt tac gtc     384
Glu Arg Thr Pro Pro Val Cys Gly Ala Leu Arg His Arg Arg Tyr Val
        115                 120                 125 cac cgc cgt cgc gtc ctc tac ggc gac gac ccg gcc cag ttg ctc gac     432
His Arg Arg Arg Val Leu Tyr Gly Asp Asp Pro Ala Gln Leu Leu Asp
    130                 135                 140 gta tgg cgc cgc aaa gat atg ccc acc aaa ccc gcg ccg gtg ttg atc     480
Val Trp Arg Arg Lys Asp Met Pro Thr Lys Pro Ala Pro Val Leu Ile
145                 150                 155                 160 ttc gtc cca ggc ggt gcc tgg gtg cac ggc agt cgc gcc atc cag ggg     528
Phe Val Pro Gly Gly Ala Trp Val His Gly Ser Arg Ala Ile Gln Gly
                165                 170                 175 tat gcg gtg ctg tct cgg ctg gcc gca cag ggg tgg gtg tgc cta tcg     576
Tyr Ala Val Leu Ser Arg Leu Ala Ala Gln Gly Trp Val Cys Leu Ser
            180                 185                 190 atc gac tac cgg gtc gca ccg cat cac cgc tgg cca cga cac atc ctg     624
Ile Asp Tyr Arg Val Ala Pro His His Arg Trp Pro Arg His Ile Leu
        195                 200                 205 gat gtc aag acc gcc atc gcg tgg gca cgg gcc aat gtc gac aaa ttc     672
Asp Val Lys Thr Ala Ile Ala Trp Ala Arg Ala Asn Val Asp Lys Phe
    210                 215                 220 ggc ggt gac cgc aat ttc att gcg gtg gct ggt tgt tcg gcc ggc ggc     720
Gly Gly Asp Arg Asn Phe Ile Ala Val Ala Gly Cys Ser Ala Gly Gly
225                 230                 235                 240 cac ttg tcc gcg ctg gcc ggg ctc acc gcc aac gac ccg caa tat cag     768
His Leu Ser Ala Leu Ala Gly Leu Thr Ala Asn Asp Pro Gln Tyr Gln
                245                 250                 255 gcc gag ctg cca gag ggc tcc gac acg tcg gtc gac gcg gtg gtg ggg     816
Ala Glu Leu Pro Glu Gly Ser Asp Thr Ser Val Asp Ala Val Val Gly
            260                 265                 270 att tac ggc cgc tac gac tgg gag gac cgc tcc acc ccg gaa cgt gcc     864
Ile Tyr Gly Arg Tyr Asp Trp Glu Asp Arg Ser Thr Pro Glu Arg Ala
        275                 280                 285 cgg ttc gtc gat ttt ctg gag cgg gta gtg gtt cag cgc acg att gat     912
Arg Phe Val Asp Phe Leu Glu Arg Val Val Val Gln Arg Thr Ile Asp
    290                 295                 300 cgt cac ccc gaa gtg ttc cgt gac gcg tcg ccg atc caa cga gtc acc     960
Arg His Pro Glu Val Phe Arg Asp Ala Ser Pro Ile Gln Arg Val Thr
305                 310                 315                 320 aga aat gca ccg cca ttc ctg gtg att cat ggc agc cgt gac tgt gtc    1008
Arg Asn Ala Pro Pro Phe Leu Val Ile His Gly Ser Arg Asp Cys Val
                325                 330                 335 atc ccg gtt gag cag gcg cgg agc ttt gtc gag cgg tta cga gcg gtc    1056
Ile Pro Val Glu Gln Ala Arg Ser Phe Val Glu Arg Leu Arg Ala Val
            340                 345                 350 tcc cgc tca cag gtt ggc tac ctg gag ctg ccc ggt gcg ggc cac ggc    1104
Ser Arg Ser Gln Val Gly Tyr Leu Glu Leu Pro Gly Ala Gly His Gly
        355                 360                 365
```

```
ttc gac ctg cta gac ggc gct cgc acc ggc ccg acg gca cac gcg atc    1152
Phe Asp Leu Leu Asp Gly Ala Arg Thr Gly Pro Thr Ala His Ala Ile
    370                 375                 380 gcg ctg ttt ctc aac cag gtt cat cgc agc cgg gca cag ttc gcg aaa    1200
Ala Leu Phe Leu Asn Gln Val His Arg Ser Arg Ala Gln Phe Ala Lys
385                 390                 395                 400 gag gtc atc taa                                                     1212
Glu Val Ile <210> SEQ ID NO 6
<211> LENGTH: 403
<212> TYPE: PRT
<213> ORGANISM: Mycbacterium tuberculosis Strain H37Rv

<400> SEQUENCE: 6
```

Met Asn Gln Arg Arg Ala Ala Gly Ser Thr Gly Val Ala Tyr Ile Arg
1               5                   10                  15

Trp Leu Leu Arg Ala Arg Pro Ala Asp Tyr Met Leu Ala Leu Ser Val
            20                  25                  30

Ala Gly Gly Ser Leu Pro Val Val Gly Lys His Leu Lys Pro Leu Gly
        35                  40                  45

Gly Val Thr Ala Ile Gly Val Trp Gly Ala Arg His Ala Ser Asp Phe
    50                  55                  60

Leu Ser Ala Thr Ala Lys Asp Leu Leu Thr Pro Gly Ile Asn Glu Val
65                  70                  75                  80

Arg Arg Arg Asp Arg Ala Ser Thr Gln Glu Val Ser Val Ala Ala Leu
                85                  90                  95

Arg Gly Ile Val Ser Pro Asp Asp Leu Ala Val Glu Trp Pro Ala Pro
            100                 105                 110

Glu Arg Thr Pro Pro Val Cys Gly Ala Leu Arg His Arg Arg Tyr Val
        115                 120                 125

His Arg Arg Arg Val Leu Tyr Gly Asp Asp Pro Ala Gln Leu Leu Asp
    130                 135                 140

Val Trp Arg Arg Lys Asp Met Pro Thr Lys Pro Ala Pro Val Leu Ile
145                 150                 155                 160

Phe Val Pro Gly Gly Ala Trp Val His Gly Ser Arg Ala Ile Gln Gly
                165                 170                 175

Tyr Ala Val Leu Ser Arg Leu Ala Ala Gln Gly Trp Val Cys Leu Ser
            180                 185                 190

Ile Asp Tyr Arg Val Ala Pro His Arg Trp Pro Arg His Ile Leu
        195                 200                 205

Asp Val Lys Thr Ala Ile Ala Trp Ala Arg Ala Asn Val Asp Lys Phe
    210                 215                 220

Gly Gly Asp Arg Asn Phe Ile Ala Val Ala Gly Cys Ser Ala Gly Gly
225                 230                 235                 240

His Leu Ser Ala Leu Ala Gly Leu Thr Ala Asn Asp Pro Gln Tyr Gln
                245                 250                 255

Ala Glu Leu Pro Glu Gly Ser Asp Thr Ser Val Asp Ala Val Val Gly
            260                 265                 270

Ile Tyr Gly Arg Tyr Asp Trp Glu Asp Arg Ser Thr Pro Glu Arg Ala
        275                 280                 285

Arg Phe Val Asp Phe Leu Glu Arg Val Val Gln Arg Thr Ile Asp
    290                 295                 300

Arg His Pro Glu Val Phe Arg Asp Ala Ser Pro Ile Gln Arg Val Thr
305                 310                 315                 320

Arg Asn Ala Pro Pro Phe Leu Val Ile His Gly Ser Arg Asp Cys Val
            325                 330                 335

Ile Pro Val Glu Gln Ala Arg Ser Phe Val Glu Arg Leu Arg Ala Val
            340                 345                 350

Ser Arg Ser Gln Val Gly Tyr Leu Glu Leu Pro Gly Ala Gly His Gly
        355                 360                 365

Phe Asp Leu Leu Asp Gly Ala Arg Thr Gly Pro Thr Ala His Ala Ile
    370                 375                 380

Ala Leu Phe Leu Asn Gln Val His Arg Ser Ala Gln Phe Ala Lys
385                 390                 395                 400

Glu Val Ile

<210> SEQ ID NO 7
<211> LENGTH: 20
<212> TYPE: PRT
<213> ORGANISM: Artificial Sequence
<220> FEATURE:
<223> OTHER INFORMATION: Synthetic

<400> SEQUENCE: 7

Met Asp Val Ala Leu Gly Val Ala Val Thr Asp Arg Val Ala Arg Leu
1               5                   10                  15

Ala Leu Val Asp
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic

<400> SEQUENCE: 8

Asp Arg Val Ala Arg Leu Ala Leu Val Asp Ser Ala Ala Pro Gly Thr
1               5                   10                  15

Val Ile Asp Gln
            20

<210> SEQ ID NO 9
<211> LENGTH: 20
<212> TYPE: PRT
<213> ORGANISM: Artificial Sequence
<220> FEATURE:
<223> OTHER INFORMATION: Synthetic

<400> SEQUENCE: 9

Ser Ala Ala Pro Gly Thr Val Ile Asp Gln Phe Val Leu Asp Val Ala
1               5                   10                  15

Glu His Pro Val
            20

<210> SEQ ID NO 10
<211> LENGTH: 20
<212> TYPE: PRT
<213> ORGANISM: Artificial Sequence
<220> FEATURE:
<223> OTHER INFORMATION: Synthetic

<400> SEQUENCE: 10

Phe Val Leu Asp Val Ala Glu His Pro Val Glu Val Leu Thr Glu Thr
1               5                   10                  15

Val Val Gly Thr

```
<210> SEQ ID NO 11
<211> LENGTH: 20
<212> TYPE: PRT
<213> ORGANISM: Artificial Sequence
<220> FEATURE:
<223> OTHER INFORMATION: Synthetic

<400> SEQUENCE: 11

Glu Val Leu Thr Glu Thr Val Val Gly Thr Asp Arg Ser Leu Ala Gly
1               5                   10                  15

Glu Asn His Arg
            20

<210> SEQ ID NO 12
<211> LENGTH: 20
<212> TYPE: PRT
<213> ORGANISM: Artificial Sequence
<220> FEATURE:
<223> OTHER INFORMATION: Synthetic

<400> SEQUENCE: 12

Asp Arg Ser Leu Ala Gly Glu Asn His Arg Leu Val Ala Thr Arg Leu
1               5                   10                  15

Cys Trp Pro Asp
            20

<210> SEQ ID NO 13
<211> LENGTH: 20
<212> TYPE: PRT
<213> ORGANISM: Artificial Sequence
<220> FEATURE:
<223> OTHER INFORMATION: Synthetic

<400> SEQUENCE: 13

Leu Val Ala Thr Arg Leu Cys Trp Pro Asp Gln Ala Lys Ala Asp Glu
1               5                   10                  15

Leu Gln His Ala
            20

<210> SEQ ID NO 14
<211> LENGTH: 20
<212> TYPE: PRT
<213> ORGANISM: Artificial Sequence
<220> FEATURE:
<223> OTHER INFORMATION: Synthetic

<400> SEQUENCE: 14

Gln Ala Lys Ala Asp Glu Leu Gln His Ala Leu Gln Asp Ser Gly Val
1               5                   10                  15

His Asp Val Ala
            20

<210> SEQ ID NO 15
<211> LENGTH: 20
<212> TYPE: PRT
<213> ORGANISM: Artificial Sequence
<220> FEATURE:
<223> OTHER INFORMATION: Synthetic

<400> SEQUENCE: 15

Leu Gln Asp Ser Gly Val His Asp Val Ala Val Ile Ser Glu Ala Gln
1               5                   10                  15
```

Ala Ala Thr Ala
        20

<210> SEQ ID NO 16
<211> LENGTH: 20
<212> TYPE: PRT
<213> ORGANISM: Artificial Sequence
<220> FEATURE:
<223> OTHER INFORMATION: Synthetic

<400> SEQUENCE: 16

Val Ile Ser Glu Ala Gln Ala Ala Thr Ala Leu Val Gly Ala Ala His
1               5                   10                  15

Ala Gly Ser Ala
        20

<210> SEQ ID NO 17
<211> LENGTH: 20
<212> TYPE: PRT
<213> ORGANISM: Artificial Sequence
<220> FEATURE:
<223> OTHER INFORMATION: Synthetic

<400> SEQUENCE: 17

Leu Val Gly Ala Ala His Ala Gly Ser Ala Val Leu Leu Val Gly Asp
1               5                   10                  15

Glu Thr Ala Thr
        20

<210> SEQ ID NO 18
<211> LENGTH: 20
<212> TYPE: PRT
<213> ORGANISM: Artificial Sequence
<220> FEATURE:
<223> OTHER INFORMATION: Synthetic

<400> SEQUENCE: 18

Val Leu Leu Val Gly Asp Glu Thr Ala Thr Leu Ser Val Val Gly Asp
1               5                   10                  15

Pro Asp Ala Pro
        20

<210> SEQ ID NO 19
<211> LENGTH: 20
<212> TYPE: PRT
<213> ORGANISM: Artificial Sequence
<220> FEATURE:
<223> OTHER INFORMATION: Synthetic

<400> SEQUENCE: 19

Leu Ser Val Val Gly Asp Pro Asp Ala Pro Pro Thr Met Val Ala Val
1               5                   10                  15

Ala Pro Val Ala
        20

<210> SEQ ID NO 20
<211> LENGTH: 20
<212> TYPE: PRT
<213> ORGANISM: Artificial Sequence
<220> FEATURE:
<223> OTHER INFORMATION: Synthetic

<400> SEQUENCE: 20

Pro Thr Met Val Ala Val Ala Pro Val Ala Gly Ala Asp Ala Thr Ser
1               5                   10                  15

Thr Val Asp Thr
        20

<210> SEQ ID NO 21
<211> LENGTH: 20
<212> TYPE: PRT
<213> ORGANISM: Artificial Sequence
<220> FEATURE:
<223> OTHER INFORMATION: Synthetic

<400> SEQUENCE: 21

Gly Ala Asp Ala Thr Ser Thr Val Asp Thr Leu Met Ala Arg Leu Gly
1               5                   10                  15

Asp Gln Ala Leu
        20

<210> SEQ ID NO 22
<211> LENGTH: 20
<212> TYPE: PRT
<213> ORGANISM: Artificial Sequence
<220> FEATURE:
<223> OTHER INFORMATION: Synthetic

<400> SEQUENCE: 22

Leu Met Ala Arg Leu Gly Asp Gln Ala Leu Ala Pro Gly Asp Val Phe
1               5                   10                  15

Leu Val Gly Arg
        20

<210> SEQ ID NO 23
<211> LENGTH: 20
<212> TYPE: PRT
<213> ORGANISM: Artificial Sequence
<220> FEATURE:
<223> OTHER INFORMATION: Synthetic

<400> SEQUENCE: 23

Ala Pro Gly Asp Val Phe Leu Val Gly Arg Ser Ala Glu His Thr Thr
1               5                   10                  15

Val Leu Ala Asp
        20

<210> SEQ ID NO 24
<211> LENGTH: 20
<212> TYPE: PRT
<213> ORGANISM: Artificial Sequence
<220> FEATURE:
<223> OTHER INFORMATION: Synthetic

<400> SEQUENCE: 24

Ser Ala Glu His Thr Thr Val Leu Ala Asp Gln Leu Arg Ala Ala Ser
1               5                   10                  15

Thr Met Arg Val
        20

<210> SEQ ID NO 25
<211> LENGTH: 20
<212> TYPE: PRT
<213> ORGANISM: Artificial Sequence
<220> FEATURE:
<223> OTHER INFORMATION: Synthetic

<400> SEQUENCE: 25

Gln Leu Arg Ala Ala Ser Thr Met Arg Val Gln Thr Pro Asp Asp Pro

```
1               5                   10                  15
Thr Phe Ala Leu
            20
```

<210> SEQ ID NO 26
<211> LENGTH: 20
<212> TYPE: PRT
<213> ORGANISM: Artificial Sequence
<220> FEATURE:
<223> OTHER INFORMATION: Synthetic

<400> SEQUENCE: 26

```
Gln Thr Pro Asp Asp Pro Thr Phe Ala Leu Ala Arg Gly Ala Ala Met
1               5                   10                  15

Ala Ala Gly Ala
            20
```

<210> SEQ ID NO 27
<211> LENGTH: 20
<212> TYPE: PRT
<213> ORGANISM: Artificial Sequence
<220> FEATURE:
<223> OTHER INFORMATION: Synthetic

<400> SEQUENCE: 27

```
Ala Arg Gly Ala Ala Met Ala Ala Gly Ala Ala Thr Met Ala His Pro
1               5                   10                  15

Ala Leu Val Ala
            20
```

<210> SEQ ID NO 28
<211> LENGTH: 20
<212> TYPE: PRT
<213> ORGANISM: Artificial Sequence
<220> FEATURE:
<223> OTHER INFORMATION: Synthetic

<400> SEQUENCE: 28

```
Ala Thr Met Ala His Pro Ala Leu Val Ala Asp Ala Thr Thr Ser Leu
1               5                   10                  15

Pro Arg Ala Glu
            20
```

<210> SEQ ID NO 29
<211> LENGTH: 20
<212> TYPE: PRT
<213> ORGANISM: Artificial Sequence
<220> FEATURE:
<223> OTHER INFORMATION: Synthetic

<400> SEQUENCE: 29

```
Asp Ala Thr Thr Ser Leu Pro Arg Ala Glu Ala Gly Gln Ser Gly Ser
1               5                   10                  15

Glu Gly Glu Gln
            20
```

<210> SEQ ID NO 30
<211> LENGTH: 20
<212> TYPE: PRT
<213> ORGANISM: Artificial Sequence
<220> FEATURE:
<223> OTHER INFORMATION: Synthetic

<400> SEQUENCE: 30

```
Ala Gly Gln Ser Gly Ser Glu Gly Glu Gln Leu Ala Tyr Ser Gln Ala
1               5                   10                  15

Ser Asp Tyr Glu
            20

<210> SEQ ID NO 31
<211> LENGTH: 20
<212> TYPE: PRT
<213> ORGANISM: Artificial Sequence
<220> FEATURE:
<223> OTHER INFORMATION: Synthetic

<400> SEQUENCE: 31

Leu Ala Tyr Ser Gln Ala Ser Asp Tyr Glu Leu Leu Pro Val Asp Glu
1               5                   10                  15

Tyr Glu Glu His
            20

<210> SEQ ID NO 32
<211> LENGTH: 20
<212> TYPE: PRT
<213> ORGANISM: Artificial Sequence
<220> FEATURE:
<223> OTHER INFORMATION: Synthetic

<400> SEQUENCE: 32

Leu Leu Pro Val Asp Glu Tyr Glu Glu His Asp Glu Tyr Gly Ala Ala
1               5                   10                  15

Ala Asp Arg Ser
            20

<210> SEQ ID NO 33
<211> LENGTH: 20
<212> TYPE: PRT
<213> ORGANISM: Artificial Sequence
<220> FEATURE:
<223> OTHER INFORMATION: Synthetic

<400> SEQUENCE: 33

Asp Glu Tyr Gly Ala Ala Ala Asp Arg Ser Ala Pro Leu Ser Arg Arg
1               5                   10                  15

Ser Leu Leu Ile
            20

<210> SEQ ID NO 34
<211> LENGTH: 20
<212> TYPE: PRT
<213> ORGANISM: Artificial Sequence
<220> FEATURE:
<223> OTHER INFORMATION: Synthetic

<400> SEQUENCE: 34

Ala Pro Leu Ser Arg Arg Ser Leu Leu Ile Gly Asn Ala Val Val Ala
1               5                   10                  15

Phe Ala Val Ile
            20

<210> SEQ ID NO 35
<211> LENGTH: 20
<212> TYPE: PRT
<213> ORGANISM: Artificial Sequence
<220> FEATURE:
<223> OTHER INFORMATION: Synthetic

<400> SEQUENCE: 35
```

```
Gly Asn Ala Val Val Ala Phe Ala Val Ile Gly Phe Ala Ser Leu Ala
1               5                  10                  15

Val Ala Val Ala
            20

<210> SEQ ID NO 36
<211> LENGTH: 20
<212> TYPE: PRT
<213> ORGANISM: Artificial Sequence
<220> FEATURE:
<223> OTHER INFORMATION: Synthetic

<400> SEQUENCE: 36

Gly Phe Ala Ser Leu Ala Val Ala Val Ala Val Thr Ile Arg Pro Thr
1               5                  10                  15

Ala Ala Ser Lys
            20

<210> SEQ ID NO 37
<211> LENGTH: 20
<212> TYPE: PRT
<213> ORGANISM: Artificial Sequence
<220> FEATURE:
<223> OTHER INFORMATION: Synthetic

<400> SEQUENCE: 37

Val Thr Ile Arg Pro Thr Ala Ala Ser Lys Pro Val Glu Gly His Gln
1               5                  10                  15

Asn Ala Gln Pro
            20

<210> SEQ ID NO 38
<211> LENGTH: 20
<212> TYPE: PRT
<213> ORGANISM: Artificial Sequence
<220> FEATURE:
<223> OTHER INFORMATION: Synthetic

<400> SEQUENCE: 38

Pro Val Glu Gly His Gln Asn Ala Gln Pro Gly Lys Phe Met Pro Leu
1               5                  10                  15

Leu Pro Thr Gln
            20

<210> SEQ ID NO 39
<211> LENGTH: 20
<212> TYPE: PRT
<213> ORGANISM: Artificial Sequence
<220> FEATURE:
<223> OTHER INFORMATION: Synthetic

<400> SEQUENCE: 39

Gly Lys Phe Met Pro Leu Leu Pro Thr Gln Gln Gln Ala Pro Val Pro
1               5                  10                  15

Pro Pro Pro Pro
            20

<210> SEQ ID NO 40
<211> LENGTH: 20
<212> TYPE: PRT
<213> ORGANISM: Artificial Sequence
<220> FEATURE:
<223> OTHER INFORMATION: Synthetic
```

```
<400> SEQUENCE: 40

Gln Gln Ala Pro Val Pro Pro Pro Asp Asp Pro Thr Ala Gly
1               5                   10                  15

Phe Gln Gly Gly
            20

<210> SEQ ID NO 41
<211> LENGTH: 20
<212> TYPE: PRT
<213> ORGANISM: Artificial Sequence
<220> FEATURE:
<223> OTHER INFORMATION: Synthetic

<400> SEQUENCE: 41

Asp Asp Pro Thr Ala Gly Phe Gln Gly Gly Thr Ile Pro Ala Val Gln
1               5                   10                  15

Asn Val Val Pro
            20

<210> SEQ ID NO 42
<211> LENGTH: 20
<212> TYPE: PRT
<213> ORGANISM: Artificial Sequence
<220> FEATURE:
<223> OTHER INFORMATION: Synthetic

<400> SEQUENCE: 42

Thr Ile Pro Ala Val Gln Asn Val Val Pro Arg Pro Gly Thr Ser Pro
1               5                   10                  15

Gly Val Gly Gly
            20

<210> SEQ ID NO 43
<211> LENGTH: 20
<212> TYPE: PRT
<213> ORGANISM: Artificial Sequence
<220> FEATURE:
<223> OTHER INFORMATION: Synthetic

<400> SEQUENCE: 43

Arg Pro Gly Thr Ser Pro Gly Val Gly Gly Thr Pro Ala Ser Pro Ala
1               5                   10                  15

Pro Glu Ala Pro
            20

<210> SEQ ID NO 44
<211> LENGTH: 20
<212> TYPE: PRT
<213> ORGANISM: Artificial Sequence
<220> FEATURE:
<223> OTHER INFORMATION: Synthetic

<400> SEQUENCE: 44

Thr Pro Ala Ser Pro Ala Pro Glu Ala Pro Ala Val Pro Gly Val Val
1               5                   10                  15

Pro Ala Pro Val
            20

<210> SEQ ID NO 45
<211> LENGTH: 20
<212> TYPE: PRT
<213> ORGANISM: Artificial Sequence
<220> FEATURE:
<223> OTHER INFORMATION: Synthetic
```

```
<400> SEQUENCE: 45

Ala Val Pro Gly Val Val Pro Ala Pro Val Pro Ile Pro Val Pro Ile
1               5                   10                  15

Ile Ile Pro Pro
            20

<210> SEQ ID NO 46
<211> LENGTH: 20
<212> TYPE: PRT
<213> ORGANISM: Artificial Sequence
<220> FEATURE:
<223> OTHER INFORMATION: Synthetic

<400> SEQUENCE: 46

Pro Ile Pro Val Pro Ile Ile Ile Pro Pro Phe Pro Gly Trp Gln Pro
1               5                   10                  15

Gly Met Pro Thr
            20

<210> SEQ ID NO 47
<211> LENGTH: 20
<212> TYPE: PRT
<213> ORGANISM: Artificial Sequence
<220> FEATURE:
<223> OTHER INFORMATION: Synthetic

<400> SEQUENCE: 47

Phe Pro Gly Trp Gln Pro Gly Met Pro Thr Ile Pro Thr Ala Pro Pro
1               5                   10                  15

Thr Thr Pro Val
            20

<210> SEQ ID NO 48
<211> LENGTH: 20
<212> TYPE: PRT
<213> ORGANISM: Artificial Sequence
<220> FEATURE:
<223> OTHER INFORMATION: Synthetic

<400> SEQUENCE: 48

Ile Pro Thr Ala Pro Pro Thr Thr Pro Val Thr Thr Ser Ala Thr Thr
1               5                   10                  15

Pro Pro Thr Thr
            20

<210> SEQ ID NO 49
<211> LENGTH: 20
<212> TYPE: PRT
<213> ORGANISM: Artificial Sequence
<220> FEATURE:
<223> OTHER INFORMATION: Synthetic

<400> SEQUENCE: 49

Thr Thr Ser Ala Thr Thr Pro Pro Thr Thr Pro Pro Thr Thr Pro Val
1               5                   10                  15

Thr Thr Pro Pro
            20

<210> SEQ ID NO 50
<211> LENGTH: 20
<212> TYPE: PRT
<213> ORGANISM: Artificial Sequence
<220> FEATURE:
```

<223> OTHER INFORMATION: Synthetic

<400> SEQUENCE: 50

Pro Pro Thr Thr Pro Val Thr Thr Pro Thr Thr Pro Pro Thr Thr
1               5                   10                  15

Pro Val Thr Thr
            20

<210> SEQ ID NO 51
<211> LENGTH: 20
<212> TYPE: PRT
<213> ORGANISM: Artificial Sequence
<220> FEATURE:
<223> OTHER INFORMATION: Synthetic

<400> SEQUENCE: 51

Thr Thr Pro Pro Thr Thr Pro Val Thr Thr Pro Pro Thr Pro Pro
1               5                   10                  15

Thr Thr Pro Val
            20

<210> SEQ ID NO 52
<211> LENGTH: 20
<212> TYPE: PRT
<213> ORGANISM: Artificial Sequence
<220> FEATURE:
<223> OTHER INFORMATION: Synthetic

<400> SEQUENCE: 52

Pro Pro Thr Thr Pro Pro Thr Thr Pro Val Thr Thr Pro Pro Thr Thr
1               5                   10                  15

Val Ala Pro Thr
            20

<210> SEQ ID NO 53
<211> LENGTH: 20
<212> TYPE: PRT
<213> ORGANISM: Artificial Sequence
<220> FEATURE:
<223> OTHER INFORMATION: Synthetic

<400> SEQUENCE: 53

Thr Thr Pro Pro Thr Thr Val Ala Pro Thr Thr Val Ala Pro Thr Thr
1               5                   10                  15

Val Ala Pro Thr
            20

<210> SEQ ID NO 54
<211> LENGTH: 20
<212> TYPE: PRT
<213> ORGANISM: Artificial Sequence
<220> FEATURE:
<223> OTHER INFORMATION: Synthetic

<400> SEQUENCE: 54

Thr Val Ala Pro Thr Thr Val Ala Pro Thr Thr Val Ala Pro Thr Thr
1               5                   10                  15

Val Ala Pro Ala
            20

<210> SEQ ID NO 55
<211> LENGTH: 20
<212> TYPE: PRT
<213> ORGANISM: Artificial Sequence
<220> FEATURE:
<223> OTHER INFORMATION: Synthetic

<400> SEQUENCE: 55

Thr Val Ala Pro Thr Thr Val Ala Pro Ala Thr Ala Thr Pro Thr Thr
1               5                   10                  15

Val Ala Pro Gln
            20

<210> SEQ ID NO 56
<211> LENGTH: 20
<212> TYPE: PRT
<213> ORGANISM: Artificial Sequence
<220> FEATURE:
<223> OTHER INFORMATION: Synthetic

<400> SEQUENCE: 56

Thr Ala Thr Pro Thr Thr Val Ala Pro Gln Pro Thr Gln Gln Pro Thr
1               5                   10                  15

Gln Gln Pro Thr
            20

<210> SEQ ID NO 57
<211> LENGTH: 20
<212> TYPE: PRT
<213> ORGANISM: Artificial Sequence
<220> FEATURE:
<223> OTHER INFORMATION: Synthetic

<400> SEQUENCE: 57

Pro Thr Gln Gln Pro Thr Gln Gln Pro Thr Gln Gln Met Pro Thr Gln
1               5                   10                  15

Gln Gln Thr Val
            20

<210> SEQ ID NO 58
<211> LENGTH: 20
<212> TYPE: PRT
<213> ORGANISM: Artificial Sequence
<220> FEATURE:
<223> OTHER INFORMATION: Synthetic

<400> SEQUENCE: 58

Gln Gln Met Pro Thr Gln Gln Thr Val Ala Pro Gln Thr Val Ala
1               5                   10                  15

Pro Ala Pro Gln
            20

<210> SEQ ID NO 59
<211> LENGTH: 20
<212> TYPE: PRT
<213> ORGANISM: Artificial Sequence
<220> FEATURE:
<223> OTHER INFORMATION: Synthetic

<400> SEQUENCE: 59

Ala Pro Gln Thr Val Ala Pro Ala Pro Gln Pro Pro Ser Gly Gly Arg
1               5                   10                  15

Asn Gly Ser Gly
            20

<210> SEQ ID NO 60
<211> LENGTH: 20
<212> TYPE: PRT

```
<213> ORGANISM: Artificial Sequence
<220> FEATURE:
<223> OTHER INFORMATION: Synthetic

<400> SEQUENCE: 60

Pro Gln Pro Pro Ser Gly Gly Arg Asn Gly Ser Gly Gly Gly Asp Leu
1               5                   10                  15

Phe Gly Gly Phe
            20

<210> SEQ ID NO 61
<211> LENGTH: 20
<212> TYPE: PRT
<213> ORGANISM: Artificial Sequence
<220> FEATURE:
<223> OTHER INFORMATION: Synthetic

<400> SEQUENCE: 61

Met Ser Phe Val Val Ala Val Pro Glu Ala Leu Ala Ala Ala Ala Ser
1               5                   10                  15

Asp Val Ala Asn
            20

<210> SEQ ID NO 62
<211> LENGTH: 20
<212> TYPE: PRT
<213> ORGANISM: Artificial Sequence
<220> FEATURE:
<223> OTHER INFORMATION: Synthetic

<400> SEQUENCE: 62

Leu Ala Ala Ala Ala Ser Asp Val Ala Asn Ile Gly Ser Ala Leu Ser
1               5                   10                  15

Ala Ala Asn Ala
            20

<210> SEQ ID NO 63
<211> LENGTH: 20
<212> TYPE: PRT
<213> ORGANISM: Artificial Sequence
<220> FEATURE:
<223> OTHER INFORMATION: Synthetic

<400> SEQUENCE: 63

Ile Gly Ser Ala Leu Ser Ala Ala Asn Ala Ala Ala Ala Ala Gly Thr
1               5                   10                  15

Thr Gly Leu Leu
            20

<210> SEQ ID NO 64
<211> LENGTH: 20
<212> TYPE: PRT
<213> ORGANISM: Artificial Sequence
<220> FEATURE:
<223> OTHER INFORMATION: Synthetic

<400> SEQUENCE: 64

Ala Ala Ala Ala Gly Thr Thr Gly Leu Leu Ala Gly Ala Asp Glu
1               5                   10                  15

Val Ser Ala Ala
            20

<210> SEQ ID NO 65
<211> LENGTH: 20
```

```
<212> TYPE: PRT
<213> ORGANISM: Artificial Sequence
<220> FEATURE:
<223> OTHER INFORMATION: Synthetic

<400> SEQUENCE: 65

Ala Ala Gly Ala Asp Glu Val Ser Ala Ala Leu Ala Ser Leu Phe Ser
1               5                   10                  15

Gly His Ala Val
            20

<210> SEQ ID NO 66
<211> LENGTH: 20
<212> TYPE: PRT
<213> ORGANISM: Artificial Sequence
<220> FEATURE:
<223> OTHER INFORMATION: Synthetic

<400> SEQUENCE: 66

Leu Ala Ser Leu Phe Ser Gly His Ala Val Ser Tyr Gln Gln Val Ala
1               5                   10                  15

Ala Gln Ala Thr
            20

<210> SEQ ID NO 67
<211> LENGTH: 20
<212> TYPE: PRT
<213> ORGANISM: Artificial Sequence
<220> FEATURE:
<223> OTHER INFORMATION: Synthetic

<400> SEQUENCE: 67

Ser Tyr Gln Gln Val Ala Ala Gln Ala Thr Ala Leu His Asp Gln Phe
1               5                   10                  15

Val Gln Ala Leu
            20

<210> SEQ ID NO 68
<211> LENGTH: 20
<212> TYPE: PRT
<213> ORGANISM: Artificial Sequence
<220> FEATURE:
<223> OTHER INFORMATION: Synthetic

<400> SEQUENCE: 68

Ala Leu His Asp Gln Phe Val Gln Ala Leu Thr Gly Ala Gly Gly Ser
1               5                   10                  15

Tyr Ala Leu Thr
            20

<210> SEQ ID NO 69
<211> LENGTH: 20
<212> TYPE: PRT
<213> ORGANISM: Artificial Sequence
<220> FEATURE:
<223> OTHER INFORMATION: Synthetic

<400> SEQUENCE: 69

Thr Gly Ala Gly Gly Ser Tyr Ala Leu Thr Glu Ala Ala Asn Val Gln
1               5                   10                  15

Gln Asn Leu Leu
            20

<210> SEQ ID NO 70
```

```
<211> LENGTH: 20
<212> TYPE: PRT
<213> ORGANISM: Artificial Sequence
<220> FEATURE:
<223> OTHER INFORMATION: Synthetic

<400> SEQUENCE: 70

Glu Ala Ala Asn Val Gln Gln Asn Leu Leu Asn Ala Ile Asn Ala Pro
1               5                   10                  15

Thr Gln Ala Leu
            20

<210> SEQ ID NO 71
<211> LENGTH: 20
<212> TYPE: PRT
<213> ORGANISM: Artificial Sequence
<220> FEATURE:
<223> OTHER INFORMATION: Synthetic

<400> SEQUENCE: 71

Asn Ala Ile Asn Ala Pro Thr Gln Ala Leu Leu Gly Arg Pro Leu Ile
1               5                   10                  15

Gly Asp Gly Ala
            20

<210> SEQ ID NO 72
<211> LENGTH: 20
<212> TYPE: PRT
<213> ORGANISM: Artificial Sequence
<220> FEATURE:
<223> OTHER INFORMATION: Synthetic

<400> SEQUENCE: 72

Leu Gly Arg Pro Leu Ile Gly Asp Gly Ala Val Gly Thr Ala Ser Ser
1               5                   10                  15

Pro Asp Gly Gln
            20

<210> SEQ ID NO 73
<211> LENGTH: 20
<212> TYPE: PRT
<213> ORGANISM: Artificial Sequence
<220> FEATURE:
<223> OTHER INFORMATION: Synthetic

<400> SEQUENCE: 73

Val Gly Thr Ala Ser Ser Pro Asp Gly Gln Asp Gly Gly Leu Leu Phe
1               5                   10                  15

Gly Asn Gly Gly
            20

<210> SEQ ID NO 74
<211> LENGTH: 20
<212> TYPE: PRT
<213> ORGANISM: Artificial Sequence
<220> FEATURE:
<223> OTHER INFORMATION: Synthetic

<400> SEQUENCE: 74

Asp Gly Gly Leu Leu Phe Gly Asn Gly Gly Ala Gly Tyr Asn Ser Ala
1               5                   10                  15

Ala Thr Pro Gly
            20
```

```
<210> SEQ ID NO 75
<211> LENGTH: 20
<212> TYPE: PRT
<213> ORGANISM: Artificial Sequence
<220> FEATURE:
<223> OTHER INFORMATION: Synthetic

<400> SEQUENCE: 75

Ala Gly Tyr Asn Ser Ala Ala Thr Pro Gly Met Ala Gly Gly Asn Gly
1               5                   10                  15

Gly Asn Ala Gly
            20

<210> SEQ ID NO 76
<211> LENGTH: 20
<212> TYPE: PRT
<213> ORGANISM: Artificial Sequence
<220> FEATURE:
<223> OTHER INFORMATION: Synthetic

<400> SEQUENCE: 76

Met Ala Gly Gly Asn Gly Gly Asn Ala Gly Leu Ile Gly Asn Gly Gly
1               5                   10                  15

Thr Gly Gly Ser
            20

<210> SEQ ID NO 77
<211> LENGTH: 20
<212> TYPE: PRT
<213> ORGANISM: Artificial Sequence
<220> FEATURE:
<223> OTHER INFORMATION: Synthetic

<400> SEQUENCE: 77

Leu Ile Gly Asn Gly Gly Thr Gly Gly Ser Gly Gly Ala Gly Ala Ala
1               5                   10                  15

Gly Gly Ala Gly
            20

<210> SEQ ID NO 78
<211> LENGTH: 20
<212> TYPE: PRT
<213> ORGANISM: Artificial Sequence
<220> FEATURE:
<223> OTHER INFORMATION: Synthetic

<400> SEQUENCE: 78

Gly Gly Ala Gly Ala Ala Gly Gly Ala Gly Gly Ser Gly Gly Trp Leu
1               5                   10                  15

Tyr Gly Asn Gly
            20

<210> SEQ ID NO 79
<211> LENGTH: 20
<212> TYPE: PRT
<213> ORGANISM: Artificial Sequence
<220> FEATURE:
<223> OTHER INFORMATION: Synthetic

<400> SEQUENCE: 79

Gly Ser Gly Gly Trp Leu Tyr Gly Asn Gly Asn Gly Gly Ile Gly
1               5                   10                  15

Gly Asn Ala Ile
            20
```

<210> SEQ ID NO 80
<211> LENGTH: 20
<212> TYPE: PRT
<213> ORGANISM: Artificial Sequence
<220> FEATURE:
<223> OTHER INFORMATION: Synthetic

<400> SEQUENCE: 80

Gly Asn Gly Gly Ile Gly Gly Asn Ala Ile Val Ala Gly Gly Ala Gly
1               5                   10                  15

Gly Asn Gly Gly
            20

<210> SEQ ID NO 81
<211> LENGTH: 20
<212> TYPE: PRT
<213> ORGANISM: Artificial Sequence
<220> FEATURE:
<223> OTHER INFORMATION: Synthetic

<400> SEQUENCE: 81

Val Ala Gly Gly Ala Gly Gly Asn Gly Gly Ala Gly Gly Ala Ala Gly
1               5                   10                  15

Leu Trp Gly Ser
            20

<210> SEQ ID NO 82
<211> LENGTH: 20
<212> TYPE: PRT
<213> ORGANISM: Artificial Sequence
<220> FEATURE:
<223> OTHER INFORMATION: Synthetic

<400> SEQUENCE: 82

Ala Gly Gly Ala Ala Gly Leu Trp Gly Ser Gly Gly Ser Gly Gly Gln
1               5                   10                  15

Gly Gly Asn Gly
            20

<210> SEQ ID NO 83
<211> LENGTH: 20
<212> TYPE: PRT
<213> ORGANISM: Artificial Sequence
<220> FEATURE:
<223> OTHER INFORMATION: Synthetic

<400> SEQUENCE: 83

Gly Gly Ser Gly Gly Gln Gly Gly Asn Gly Leu Thr Gly Asn Asp Gly
1               5                   10                  15

Val Asn Pro Ala
            20

<210> SEQ ID NO 84
<211> LENGTH: 20
<212> TYPE: PRT
<213> ORGANISM: Artificial Sequence
<220> FEATURE:
<223> OTHER INFORMATION: Synthetic

<400> SEQUENCE: 84

Leu Thr Gly Asn Asp Gly Val Asn Pro Ala Pro Val Thr Asn Pro Ala
1               5                   10                  15

Leu Asn Gly Ala
            20

<210> SEQ ID NO 85
<211> LENGTH: 20
<212> TYPE: PRT
<213> ORGANISM: Artificial Sequence
<220> FEATURE:
<223> OTHER INFORMATION: Synthetic

<400> SEQUENCE: 85

Pro Val Thr Asn Pro Ala Leu Asn Gly Ala Ala Gly Asp Ser Asn Ile
1               5                   10                  15

Glu Pro Gln Thr
            20

<210> SEQ ID NO 86
<211> LENGTH: 20
<212> TYPE: PRT
<213> ORGANISM: Artificial Sequence
<220> FEATURE:
<223> OTHER INFORMATION: Synthetic

<400> SEQUENCE: 86

Ala Gly Asp Ser Asn Ile Glu Pro Gln Thr Ser Val Leu Ile Gly Thr
1               5                   10                  15

Gln Gly Gly Asp
            20

<210> SEQ ID NO 87
<211> LENGTH: 20
<212> TYPE: PRT
<213> ORGANISM: Artificial Sequence
<220> FEATURE:
<223> OTHER INFORMATION: Synthetic

<400> SEQUENCE: 87

Ser Val Leu Ile Gly Thr Gln Gly Gly Asp Gly Thr Pro Gly Gly Ala
1               5                   10                  15

Gly Val Asn Gly
            20

<210> SEQ ID NO 88
<211> LENGTH: 20
<212> TYPE: PRT
<213> ORGANISM: Artificial Sequence
<220> FEATURE:
<223> OTHER INFORMATION: Synthetic

<400> SEQUENCE: 88

Gly Thr Pro Gly Gly Ala Gly Val Asn Gly Gly Asn Gly Gly Ala Gly
1               5                   10                  15

Gly Asp Ala Asn
            20

<210> SEQ ID NO 89
<211> LENGTH: 20
<212> TYPE: PRT
<213> ORGANISM: Artificial Sequence
<220> FEATURE:
<223> OTHER INFORMATION: Synthetic

<400> SEQUENCE: 89

Gly Asn Gly Gly Ala Gly Gly Asp Ala Asn Gly Asn Pro Ala Asn Thr
1               5                   10                  15

Ser Ile Ala Asn

-continued

20

<210> SEQ ID NO 90
<211> LENGTH: 20
<212> TYPE: PRT
<213> ORGANISM: Artificial Sequence
<220> FEATURE:
<223> OTHER INFORMATION: Synthetic

<400> SEQUENCE: 90

Gly Asn Pro Ala Asn Thr Ser Ile Ala Asn Ala Gly Ala Gly Gly Asn
1               5                   10                  15

Gly Ala Ala Gly
        20

<210> SEQ ID NO 91
<211> LENGTH: 20
<212> TYPE: PRT
<213> ORGANISM: Artificial Sequence
<220> FEATURE:
<223> OTHER INFORMATION: Synthetic

<400> SEQUENCE: 91

Ala Gly Ala Gly Gly Asn Gly Ala Ala Gly Gly Asp Gly Gly Ala Asn
1               5                   10                  15

Gly Gly Ala Gly
        20

<210> SEQ ID NO 92
<211> LENGTH: 20
<212> TYPE: PRT
<213> ORGANISM: Artificial Sequence
<220> FEATURE:
<223> OTHER INFORMATION: Synthetic

<400> SEQUENCE: 92

Gly Asp Gly Gly Ala Asn Gly Gly Ala Gly Gly Ala Gly Gly Gln Ala
1               5                   10                  15

Ala Ser Ala Gly
        20

<210> SEQ ID NO 93
<211> LENGTH: 20
<212> TYPE: PRT
<213> ORGANISM: Artificial Sequence
<220> FEATURE:
<223> OTHER INFORMATION: Synthetic

<400> SEQUENCE: 93

Gly Ala Gly Gly Gln Ala Ala Ser Ala Gly Ser Ser Val Gly Gly Asp
1               5                   10                  15

Gly Gly Asn Gly
        20

<210> SEQ ID NO 94
<211> LENGTH: 20
<212> TYPE: PRT
<213> ORGANISM: Artificial Sequence
<220> FEATURE:
<223> OTHER INFORMATION: Synthetic

<400> SEQUENCE: 94

Ser Ser Val Gly Gly Asp Gly Gly Asn Gly Gly Ala Gly Gly Thr Gly
1               5                   10                  15

```
Thr Asn Gly His
            20

<210> SEQ ID NO 95
<211> LENGTH: 20
<212> TYPE: PRT
<213> ORGANISM: Artificial Sequence
<220> FEATURE:
<223> OTHER INFORMATION: Synthetic

<400> SEQUENCE: 95

Gly Ala Gly Gly Thr Gly Thr Asn Gly His Ala Gly Ala Gly Ala Gly
1               5                   10                  15

Ala Gly Gly Ala
            20

<210> SEQ ID NO 96
<211> LENGTH: 20
<212> TYPE: PRT
<213> ORGANISM: Artificial Sequence
<220> FEATURE:
<223> OTHER INFORMATION: Synthetic

<400> SEQUENCE: 96

Ala Gly Gly Ala Gly Gly Ala Gly Gly Ala Gly Gly Arg Gly Gly Trp
1               5                   10                  15

Leu Val Gly Asn
            20

<210> SEQ ID NO 97
<211> LENGTH: 20
<212> TYPE: PRT
<213> ORGANISM: Artificial Sequence
<220> FEATURE:
<223> OTHER INFORMATION: Synthetic

<400> SEQUENCE: 97

Gly Gly Arg Gly Gly Trp Leu Val Gly Asn Gly Gly Asn Gly Gly Asn
1               5                   10                  15

Gly Ala Ala Gly
            20

<210> SEQ ID NO 98
<211> LENGTH: 20
<212> TYPE: PRT
<213> ORGANISM: Artificial Sequence
<220> FEATURE:
<223> OTHER INFORMATION: Synthetic

<400> SEQUENCE: 98

Gly Gly Asn Gly Gly Asn Gly Ala Ala Gly Gly Asn Gly Ala Ile Gly
1               5                   10                  15

Gly Thr Gly Gly
            20

<210> SEQ ID NO 99
<211> LENGTH: 20
<212> TYPE: PRT
<213> ORGANISM: Artificial Sequence
<220> FEATURE:
<223> OTHER INFORMATION: Synthetic

<400> SEQUENCE: 99

Gly Asn Gly Ala Ile Gly Gly Thr Gly Gly Ala Gly Gly Val Pro Ala
1               5                   10                  15
```

Asn Gln Gly Gly
            20

<210> SEQ ID NO 100
<211> LENGTH: 20
<212> TYPE: PRT
<213> ORGANISM: Artificial Sequence
<220> FEATURE:
<223> OTHER INFORMATION: Synthetic

<400> SEQUENCE: 100

Ala Gly Gly Val Pro Ala Asn Gln Gly Gly Asn Ser Ala Leu Gly Thr
1               5                   10                  15

Gln Pro Val Gly
            20

<210> SEQ ID NO 101
<211> LENGTH: 20
<212> TYPE: PRT
<213> ORGANISM: Artificial Sequence
<220> FEATURE:
<223> OTHER INFORMATION: Synthetic

<400> SEQUENCE: 101

Asn Ser Ala Leu Gly Thr Gln Pro Val Gly Gly Asp Gly Gly Asp Gly
1               5                   10                  15

Gly Asn Gly Gly
            20

<210> SEQ ID NO 102
<211> LENGTH: 20
<212> TYPE: PRT
<213> ORGANISM: Artificial Sequence
<220> FEATURE:
<223> OTHER INFORMATION: Synthetic

<400> SEQUENCE: 102

Gly Asp Gly Gly Asp Gly Gly Asn Gly Gly Thr Gly Gly Thr Gly Gly
1               5                   10                  15

Arg Gly Gly Asp
            20

<210> SEQ ID NO 103
<211> LENGTH: 20
<212> TYPE: PRT
<213> ORGANISM: Artificial Sequence
<220> FEATURE:
<223> OTHER INFORMATION: Synthetic

<400> SEQUENCE: 103

Thr Gly Gly Thr Gly Gly Arg Gly Gly Asp Gly Gly Ser Gly Gly Ala
1               5                   10                  15

Gly Gly Ala Ser
            20

<210> SEQ ID NO 104
<211> LENGTH: 20
<212> TYPE: PRT
<213> ORGANISM: Artificial Sequence
<220> FEATURE:
<223> OTHER INFORMATION: Synthetic

<400> SEQUENCE: 104

Gly Gly Ser Gly Gly Ala Gly Gly Ala Ser Gly Trp Leu Met Gly Asn

```
                        1               5                   10                  15

Gly Gly Asn Gly
            20

<210> SEQ ID NO 105
<211> LENGTH: 20
<212> TYPE: PRT
<213> ORGANISM: Artificial Sequence
<220> FEATURE:
<223> OTHER INFORMATION: Synthetic

<400> SEQUENCE: 105

Gly Trp Leu Met Gly Asn Gly Gly Asn Gly Gly Asn Gly Gly Thr Gly
1               5                   10                  15

Gly Ser Gly Gly
            20

<210> SEQ ID NO 106
<211> LENGTH: 20
<212> TYPE: PRT
<213> ORGANISM: Artificial Sequence
<220> FEATURE:
<223> OTHER INFORMATION: Synthetic

<400> SEQUENCE: 106

Gly Asn Gly Gly Thr Gly Gly Ser Gly Gly Val Gly Gly Asn Gly Gly
1               5                   10                  15

Ile Gly Gly Asp
            20

<210> SEQ ID NO 107
<211> LENGTH: 20
<212> TYPE: PRT
<213> ORGANISM: Artificial Sequence
<220> FEATURE:
<223> OTHER INFORMATION: Synthetic

<400> SEQUENCE: 107

Val Gly Gly Asn Gly Gly Ile Gly Gly Asp Gly Ala Gly Gly Gly Asn
1               5                   10                  15

Ala Thr Ser Thr
            20

<210> SEQ ID NO 108
<211> LENGTH: 20
<212> TYPE: PRT
<213> ORGANISM: Artificial Sequence
<220> FEATURE:
<223> OTHER INFORMATION: Synthetic

<400> SEQUENCE: 108

Gly Ala Gly Gly Gly Asn Ala Thr Ser Thr Ser Ser Ile Pro Phe Asp
1               5                   10                  15

Ala His Gly Gly
            20

<210> SEQ ID NO 109
<211> LENGTH: 20
<212> TYPE: PRT
<213> ORGANISM: Artificial Sequence
<220> FEATURE:
<223> OTHER INFORMATION: Synthetic

<400> SEQUENCE: 109
```

```
Ser Ser Ile Pro Phe Asp Ala His Gly Asn Gly Gly Ala Gly Gly
1               5                   10                  15

Asp Ala Gly His
            20

<210> SEQ ID NO 110
<211> LENGTH: 20
<212> TYPE: PRT
<213> ORGANISM: Artificial Sequence
<220> FEATURE:
<223> OTHER INFORMATION: Synthetic

<400> SEQUENCE: 110

Asn Gly Gly Ala Gly Gly Asp Ala Gly His Gly Gly Thr Gly Gly Asp
1               5                   10                  15

Gly Gly Asp Gly
            20

<210> SEQ ID NO 111
<211> LENGTH: 20
<212> TYPE: PRT
<213> ORGANISM: Artificial Sequence
<220> FEATURE:
<223> OTHER INFORMATION: Synthetic

<400> SEQUENCE: 111

Gly Gly Thr Gly Gly Asp Gly Gly Asp Gly Gly His Ala Gly Thr Gly
1               5                   10                  15

Gly Arg Gly Gly
            20

<210> SEQ ID NO 112
<211> LENGTH: 20
<212> TYPE: PRT
<213> ORGANISM: Artificial Sequence
<220> FEATURE:
<223> OTHER INFORMATION: Synthetic

<400> SEQUENCE: 112

Gly His Ala Gly Thr Gly Gly Arg Gly Gly Leu Leu Ala Gly Gln His
1               5                   10                  15

Ala Asn Ser Gly
            20

<210> SEQ ID NO 113
<211> LENGTH: 20
<212> TYPE: PRT
<213> ORGANISM: Artificial Sequence
<220> FEATURE:
<223> OTHER INFORMATION: Synthetic

<400> SEQUENCE: 113

Leu Leu Ala Gly Gln His Ala Asn Ser Gly Asn Gly Gly Gly Gly
1               5                   10                  15

Thr Gly Gly Ala
            20

<210> SEQ ID NO 114
<211> LENGTH: 20
<212> TYPE: PRT
<213> ORGANISM: Artificial Sequence
<220> FEATURE:
<223> OTHER INFORMATION: Synthetic

<400> SEQUENCE: 114
```

```
Asn Gly Gly Gly Gly Thr Gly Gly Ala Gly Gly Thr His Gly Thr
1               5                   10                  15

Pro Gly Ser Gly
            20

<210> SEQ ID NO 115
<211> LENGTH: 20
<212> TYPE: PRT
<213> ORGANISM: Artificial Sequence
<220> FEATURE:
<223> OTHER INFORMATION: Synthetic

<400> SEQUENCE: 115

Gly Gly Thr His Gly Thr Pro Gly Ser Gly Asn Ala Gly Gly Thr Gly
1               5                   10                  15

Thr Gly Asn Ala
            20

<210> SEQ ID NO 116
<211> LENGTH: 20
<212> TYPE: PRT
<213> ORGANISM: Artificial Sequence
<220> FEATURE:
<223> OTHER INFORMATION: Synthetic

<400> SEQUENCE: 116

Asn Ala Gly Gly Thr Gly Thr Gly Asn Ala Asp Ser Thr Asn Gly Gly
1               5                   10                  15

Pro Gly Ser Asp
            20

<210> SEQ ID NO 117
<211> LENGTH: 20
<212> TYPE: PRT
<213> ORGANISM: Artificial Sequence
<220> FEATURE:
<223> OTHER INFORMATION: Synthetic

<400> SEQUENCE: 117

Asp Ser Thr Asn Gly Gly Pro Gly Ser Asp Gly Leu Gly Gly Asp Ala
1               5                   10                  15

Phe Asn Gly Ser
            20

<210> SEQ ID NO 118
<211> LENGTH: 20
<212> TYPE: PRT
<213> ORGANISM: Artificial Sequence
<220> FEATURE:
<223> OTHER INFORMATION: Synthetic

<400> SEQUENCE: 118

Ser Asp Gly Leu Gly Gly Asp Ala Phe Asn Gly Ser Arg Gly Thr Asp
1               5                   10                  15

Gly Asn Pro Gly
            20

<210> SEQ ID NO 119
<211> LENGTH: 20
<212> TYPE: PRT
<213> ORGANISM: Artificial Sequence
<220> FEATURE:
<223> OTHER INFORMATION: Synthetic
```

```
<400> SEQUENCE: 119

Met Asn Gln Arg Arg Ala Ala Gly Ser Thr Gly Val Ala Tyr Ile Arg
1               5                   10                  15

Trp Leu Leu Arg
            20

<210> SEQ ID NO 120
<211> LENGTH: 20
<212> TYPE: PRT
<213> ORGANISM: Artificial Sequence
<220> FEATURE:
<223> OTHER INFORMATION: Synthetic

<400> SEQUENCE: 120

Gly Val Ala Tyr Ile Arg Trp Leu Leu Arg Ala Arg Pro Ala Asp Tyr
1               5                   10                  15

Met Leu Ala Leu
            20

<210> SEQ ID NO 121
<211> LENGTH: 20
<212> TYPE: PRT
<213> ORGANISM: Artificial Sequence
<220> FEATURE:
<223> OTHER INFORMATION: Synthetic

<400> SEQUENCE: 121

Ala Arg Pro Ala Asp Tyr Met Leu Ala Leu Ser Val Ala Gly Gly Ser
1               5                   10                  15

Leu Pro Val Val
            20

<210> SEQ ID NO 122
<211> LENGTH: 20
<212> TYPE: PRT
<213> ORGANISM: Artificial Sequence
<220> FEATURE:
<223> OTHER INFORMATION: Synthetic

<400> SEQUENCE: 122

Ser Val Ala Gly Gly Ser Leu Pro Val Val Gly Lys His Leu Lys Pro
1               5                   10                  15

Leu Gly Gly Val
            20

<210> SEQ ID NO 123
<211> LENGTH: 20
<212> TYPE: PRT
<213> ORGANISM: Artificial Sequence
<220> FEATURE:
<223> OTHER INFORMATION: Synthetic

<400> SEQUENCE: 123

Gly Lys His Leu Lys Pro Leu Gly Gly Val Thr Ala Ile Gly Val Trp
1               5                   10                  15

Gly Ala Arg His
            20

<210> SEQ ID NO 124
<211> LENGTH: 20
<212> TYPE: PRT
<213> ORGANISM: Artificial Sequence
<220> FEATURE:
<223> OTHER INFORMATION: Synthetic
```

```
<400> SEQUENCE: 124

Thr Ala Ile Gly Val Trp Gly Ala Arg His Ala Ser Asp Phe Leu Ser
1               5                   10                  15

Ala Thr Ala Lys
            20

<210> SEQ ID NO 125
<211> LENGTH: 20
<212> TYPE: PRT
<213> ORGANISM: Artificial Sequence
<220> FEATURE:
<223> OTHER INFORMATION: Synthetic

<400> SEQUENCE: 125

Ala Ser Asp Phe Leu Ser Ala Thr Ala Lys Asp Leu Leu Thr Pro Gly
1               5                   10                  15

Ile Asn Glu Val
            20

<210> SEQ ID NO 126
<211> LENGTH: 20
<212> TYPE: PRT
<213> ORGANISM: Artificial Sequence
<220> FEATURE:
<223> OTHER INFORMATION: Synthetic

<400> SEQUENCE: 126

Asp Leu Leu Thr Pro Gly Ile Asn Glu Val Arg Arg Arg Asp Arg Ala
1               5                   10                  15

Ser Thr Gln Glu
            20

<210> SEQ ID NO 127
<211> LENGTH: 20
<212> TYPE: PRT
<213> ORGANISM: Artificial Sequence
<220> FEATURE:
<223> OTHER INFORMATION: Synthetic

<400> SEQUENCE: 127

Arg Arg Arg Asp Arg Ala Ser Thr Gln Glu Val Ser Val Ala Ala Leu
1               5                   10                  15

Arg Gly Ile Val
            20

<210> SEQ ID NO 128
<211> LENGTH: 20
<212> TYPE: PRT
<213> ORGANISM: Artificial Sequence
<220> FEATURE:
<223> OTHER INFORMATION: Synthetic

<400> SEQUENCE: 128

Val Ser Val Ala Ala Leu Arg Gly Ile Val Ser Pro Asp Asp Leu Ala
1               5                   10                  15

Val Glu Trp Pro
            20

<210> SEQ ID NO 129
<211> LENGTH: 20
<212> TYPE: PRT
<213> ORGANISM: Artificial Sequence
<220> FEATURE:
```

```
<223> OTHER INFORMATION: Synthetic

<400> SEQUENCE: 129

Ser Pro Asp Asp Leu Ala Val Glu Trp Pro Ala Pro Glu Arg Thr Pro
1               5                   10                  15

Pro Val Cys Gly
            20

<210> SEQ ID NO 130
<211> LENGTH: 20
<212> TYPE: PRT
<213> ORGANISM: Artificial Sequence
<220> FEATURE:
<223> OTHER INFORMATION: Synthetic

<400> SEQUENCE: 130

Ala Pro Glu Arg Thr Pro Pro Val Cys Gly Ala Leu Arg His Arg Arg
1               5                   10                  15

Tyr Val His Arg
            20

<210> SEQ ID NO 131
<211> LENGTH: 20
<212> TYPE: PRT
<213> ORGANISM: Artificial Sequence
<220> FEATURE:
<223> OTHER INFORMATION: Synthetic

<400> SEQUENCE: 131

Ala Leu Arg His Arg Arg Tyr Val His Arg Arg Val Leu Tyr Gly
1               5                   10                  15

Asp Asp Pro Ala
            20

<210> SEQ ID NO 132
<211> LENGTH: 20
<212> TYPE: PRT
<213> ORGANISM: Artificial Sequence
<220> FEATURE:
<223> OTHER INFORMATION: Synthetic

<400> SEQUENCE: 132

Arg Arg Val Leu Tyr Gly Asp Asp Pro Ala Gln Leu Leu Asp Val Trp
1               5                   10                  15

Arg Arg Lys Asp
            20

<210> SEQ ID NO 133
<211> LENGTH: 20
<212> TYPE: PRT
<213> ORGANISM: Artificial Sequence
<220> FEATURE:
<223> OTHER INFORMATION: Synthetic

<400> SEQUENCE: 133

Gln Leu Leu Asp Val Trp Arg Arg Lys Asp Met Pro Thr Lys Pro Ala
1               5                   10                  15

Pro Val Leu Ile
            20

<210> SEQ ID NO 134
<211> LENGTH: 20
<212> TYPE: PRT
<213> ORGANISM: Artificial Sequence
```

```
<220> FEATURE:
<223> OTHER INFORMATION: Synthetic

<400> SEQUENCE: 134

Met Pro Thr Lys Pro Ala Pro Val Leu Ile Phe Val Pro Gly Gly Ala
1               5                   10                  15

Trp Val His Gly
            20

<210> SEQ ID NO 135
<211> LENGTH: 20
<212> TYPE: PRT
<213> ORGANISM: Artificial Sequence
<220> FEATURE:
<223> OTHER INFORMATION: Synthetic

<400> SEQUENCE: 135

Phe Val Pro Gly Gly Ala Trp Val His Gly Ser Arg Ala Ile Gln Gly
1               5                   10                  15

Tyr Ala Val Leu
            20

<210> SEQ ID NO 136
<211> LENGTH: 20
<212> TYPE: PRT
<213> ORGANISM: Artificial Sequence
<220> FEATURE:
<223> OTHER INFORMATION: Synthetic

<400> SEQUENCE: 136

Ser Arg Ala Ile Gln Gly Tyr Ala Val Leu Ser Arg Leu Ala Ala Gln
1               5                   10                  15

Gly Trp Val Cys
            20

<210> SEQ ID NO 137
<211> LENGTH: 20
<212> TYPE: PRT
<213> ORGANISM: Artificial Sequence
<220> FEATURE:
<223> OTHER INFORMATION: Synthetic

<400> SEQUENCE: 137

Ser Arg Leu Ala Ala Gln Gly Trp Val Cys Leu Ser Ile Asp Tyr Arg
1               5                   10                  15

Val Ala Pro His
            20

<210> SEQ ID NO 138
<211> LENGTH: 20
<212> TYPE: PRT
<213> ORGANISM: Artificial Sequence
<220> FEATURE:
<223> OTHER INFORMATION: Synthetic

<400> SEQUENCE: 138

Leu Ser Ile Asp Tyr Arg Val Ala Pro His His Arg Trp Pro Arg His
1               5                   10                  15

Ile Leu Asp Val
            20

<210> SEQ ID NO 139
<211> LENGTH: 20
<212> TYPE: PRT
```

-continued

<213> ORGANISM: Artificial Sequence
<220> FEATURE:
<223> OTHER INFORMATION: Synthetic

<400> SEQUENCE: 139

His Arg Trp Pro Arg His Ile Leu Asp Val Lys Thr Ala Ile Ala Trp
1               5                   10                  15

Ala Arg Ala Asn
            20

<210> SEQ ID NO 140
<211> LENGTH: 20
<212> TYPE: PRT
<213> ORGANISM: Artificial Sequence
<220> FEATURE:
<223> OTHER INFORMATION: Synthetic

<400> SEQUENCE: 140

Lys Thr Ala Ile Ala Trp Ala Arg Ala Asn Val Asp Lys Phe Gly Gly
1               5                   10                  15

Asp Arg Asn Phe
            20

<210> SEQ ID NO 141
<211> LENGTH: 20
<212> TYPE: PRT
<213> ORGANISM: Artificial Sequence
<220> FEATURE:
<223> OTHER INFORMATION: Synthetic

<400> SEQUENCE: 141

Val Asp Lys Phe Gly Gly Asp Arg Asn Phe Ile Ala Val Ala Gly Cys
1               5                   10                  15

Ser Ala Gly Gly
            20

<210> SEQ ID NO 142
<211> LENGTH: 20
<212> TYPE: PRT
<213> ORGANISM: Artificial Sequence
<220> FEATURE:
<223> OTHER INFORMATION: Synthetic

<400> SEQUENCE: 142

Ile Ala Val Ala Gly Cys Ser Ala Gly Gly His Leu Ser Ala Leu Ala
1               5                   10                  15

Gly Leu Thr Ala
            20

<210> SEQ ID NO 143
<211> LENGTH: 20
<212> TYPE: PRT
<213> ORGANISM: Artificial Sequence
<220> FEATURE:
<223> OTHER INFORMATION: Synthetic

<400> SEQUENCE: 143

His Leu Ser Ala Leu Ala Gly Leu Thr Ala Asn Asp Pro Gln Tyr Gln
1               5                   10                  15

Ala Glu Leu Pro
            20

<210> SEQ ID NO 144
<211> LENGTH: 20

```
<212> TYPE: PRT
<213> ORGANISM: Artificial Sequence
<220> FEATURE:
<223> OTHER INFORMATION: Synthetic

<400> SEQUENCE: 144

Asn Asp Pro Gln Tyr Gln Ala Glu Leu Pro Glu Gly Ser Asp Thr Ser
1               5                   10                  15

Val Asp Ala Val
            20

<210> SEQ ID NO 145
<211> LENGTH: 20
<212> TYPE: PRT
<213> ORGANISM: Artificial Sequence
<220> FEATURE:
<223> OTHER INFORMATION: Synthetic

<400> SEQUENCE: 145

Glu Gly Ser Asp Thr Ser Val Asp Ala Val Val Gly Ile Tyr Gly Arg
1               5                   10                  15

Tyr Asp Trp Glu
            20

<210> SEQ ID NO 146
<211> LENGTH: 20
<212> TYPE: PRT
<213> ORGANISM: Artificial Sequence
<220> FEATURE:
<223> OTHER INFORMATION: Synthetic

<400> SEQUENCE: 146

Val Gly Ile Tyr Gly Arg Tyr Asp Trp Glu Asp Arg Ser Thr Pro Glu
1               5                   10                  15

Arg Ala Arg Phe
            20

<210> SEQ ID NO 147
<211> LENGTH: 20
<212> TYPE: PRT
<213> ORGANISM: Artificial Sequence
<220> FEATURE:
<223> OTHER INFORMATION: Synthetic

<400> SEQUENCE: 147

Asp Arg Ser Thr Pro Glu Arg Ala Arg Phe Val Asp Phe Leu Glu Arg
1               5                   10                  15

Val Val Val Gln
            20

<210> SEQ ID NO 148
<211> LENGTH: 20
<212> TYPE: PRT
<213> ORGANISM: Artificial Sequence
<220> FEATURE:
<223> OTHER INFORMATION: Synthetic

<400> SEQUENCE: 148

Val Asp Phe Leu Glu Arg Val Val Val Gln Arg Thr Ile Asp Arg His
1               5                   10                  15

Pro Glu Val Phe
            20

<210> SEQ ID NO 149
```

```
<211> LENGTH: 20
<212> TYPE: PRT
<213> ORGANISM: Artificial Sequence
<220> FEATURE:
<223> OTHER INFORMATION: Synthetic

<400> SEQUENCE: 149

Arg Thr Ile Asp Arg His Pro Glu Val Phe Arg Asp Ala Ser Pro Ile
1               5                   10                  15

Gln Arg Val Thr
            20

<210> SEQ ID NO 150
<211> LENGTH: 20
<212> TYPE: PRT
<213> ORGANISM: Artificial Sequence
<220> FEATURE:
<223> OTHER INFORMATION: Synthetic

<400> SEQUENCE: 150

Arg Asp Ala Ser Pro Ile Gln Arg Val Thr Arg Asn Ala Pro Pro Phe
1               5                   10                  15

Leu Val Ile His
            20

<210> SEQ ID NO 151
<211> LENGTH: 20
<212> TYPE: PRT
<213> ORGANISM: Artificial Sequence
<220> FEATURE:
<223> OTHER INFORMATION: Synthetic

<400> SEQUENCE: 151

Arg Asn Ala Pro Pro Phe Leu Val Ile His Gly Ser Arg Asp Cys Val
1               5                   10                  15

Ile Pro Val Glu
            20

<210> SEQ ID NO 152
<211> LENGTH: 20
<212> TYPE: PRT
<213> ORGANISM: Artificial Sequence
<220> FEATURE:
<223> OTHER INFORMATION: Synthetic

<400> SEQUENCE: 152

Gly Ser Arg Asp Cys Val Ile Pro Val Glu Gln Ala Arg Ser Phe Val
1               5                   10                  15

Glu Arg Leu Arg
            20

<210> SEQ ID NO 153
<211> LENGTH: 20
<212> TYPE: PRT
<213> ORGANISM: Artificial Sequence
<220> FEATURE:
<223> OTHER INFORMATION: Synthetic

<400> SEQUENCE: 153

Gln Ala Arg Ser Phe Val Glu Arg Leu Arg Ala Val Ser Arg Ser Gln
1               5                   10                  15

Val Gly Tyr Leu
            20
```

-continued

<210> SEQ ID NO 154
<211> LENGTH: 20
<212> TYPE: PRT
<213> ORGANISM: Artificial Sequence
<220> FEATURE:
<223> OTHER INFORMATION: Synthetic

<400> SEQUENCE: 154

Ala Val Ser Arg Ser Gln Val Gly Tyr Leu Glu Leu Pro Gly Ala Gly
1               5                   10                  15

His Gly Phe Asp
            20

<210> SEQ ID NO 155
<211> LENGTH: 20
<212> TYPE: PRT
<213> ORGANISM: Artificial Sequence
<220> FEATURE:
<223> OTHER INFORMATION: Synthetic

<400> SEQUENCE: 155

Glu Leu Pro Gly Ala Gly His Gly Phe Asp Leu Leu Asp Gly Ala Arg
1               5                   10                  15

Thr Gly Pro Thr
            20

<210> SEQ ID NO 156
<211> LENGTH: 20
<212> TYPE: PRT
<213> ORGANISM: Artificial Sequence
<220> FEATURE:
<223> OTHER INFORMATION: Synthetic

<400> SEQUENCE: 156

Leu Leu Asp Gly Ala Arg Thr Gly Pro Thr Ala His Ala Ile Ala Leu
1               5                   10                  15

Phe Leu Asn Gln
            20

<210> SEQ ID NO 157
<211> LENGTH: 20
<212> TYPE: PRT
<213> ORGANISM: Artificial Sequence
<220> FEATURE:
<223> OTHER INFORMATION: Synthetic

<400> SEQUENCE: 157

Ala His Ala Ile Ala Leu Phe Leu Asn Gln Val His Arg Ser Arg Ala
1               5                   10                  15

Gln Phe Ala Lys
            20

<210> SEQ ID NO 158
<211> LENGTH: 20
<212> TYPE: PRT
<213> ORGANISM: Artificial Sequence
<220> FEATURE:
<223> OTHER INFORMATION: Synthetic

<400> SEQUENCE: 158

Ile Ala Leu Phe Leu Asn Gln Val His Arg Ser Arg Ala Gln Phe Ala
1               5                   10                  15

Lys Glu Val Ile
            20

<210> SEQ ID NO 159
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be Thr or Ala
<220> FEATURE:
<221> NAME/KEY: misc_feature
<222> LOCATION: (8)..(8)
<223> OTHER INFORMATION: Xaa can be Pro or Val
<220> FEATURE:
<221> NAME/KEY: misc_feature
<222> LOCATION: (11)..(11)
<223> OTHER INFORMATION: Xaa can be Pro or Ser
<220> FEATURE:
<221> NAME/KEY: misc_feature
<222> LOCATION: (12)..(12)
<223> OTHER INFORMATION: Xaa can be Val or Ala

<400> SEQUENCE: 159

Thr Xaa Pro Pro Thr Thr Pro Xaa Thr Thr Xaa Xaa
1               5                   10

<210> SEQ ID NO 160
<211> LENGTH: 20
<212> TYPE: DNA
<213> ORGANISM: Artificial Sequence
<220> FEATURE:
<223> OTHER INFORMATION: Synthetic

<400> SEQUENCE: 160
tgatcggttt cgcctcgctg                                               20

<210> SEQ ID NO 161
<211> LENGTH: 21
<212> TYPE: DNA
<213> ORGANISM: Artificial Sequence
<220> FEATURE:
<223> OTHER INFORMATION: Synthetic

<400> SEQUENCE: 161
ggaatggtgc cgccctggaa t                                             21

<210> SEQ ID NO 162
<211> LENGTH: 27
<212> TYPE: DNA
<213> ORGANISM: Artificial Sequence
<220> FEATURE:
<223> OTHER INFORMATION: Synthetic

<400> SEQUENCE: 162
agccagccga aggagagccc atatgga                                       27

<210> SEQ ID NO 163
<211> LENGTH: 27
<212> TYPE: DNA
<213> ORGANISM: Artificial Sequence
<220> FEATURE:
<223> OTHER INFORMATION: Synthetic

<400> SEQUENCE: 163
agtgaagccg cgaccgaagc ttgaacc                                       27

<210> SEQ ID NO 164

```
<211> LENGTH: 20
<212> TYPE: DNA
<213> ORGANISM: Artificial Sequence
<220> FEATURE:
<223> OTHER INFORMATION: Synthetic

<400> SEQUENCE: 164
tgccgggaca ttgctggttg                                             20

<210> SEQ ID NO 165
<211> LENGTH: 22
<212> TYPE: DNA
<213> ORGANISM: Artificial Sequence
<220> FEATURE:
<223> OTHER INFORMATION: Synthetic

<400> SEQUENCE: 165
tgatcagaac ccgccgaata ag                                          22

<210> SEQ ID NO 166
<211> LENGTH: 27
<212> TYPE: DNA
<213> ORGANISM: Artificial Sequence
<220> FEATURE:
<223> OTHER INFORMATION: Synthetic

<400> SEQUENCE: 166
ggatccatgg acgtcgcttt gggggtt                                     27

<210> SEQ ID NO 167
<211> LENGTH: 27
<212> TYPE: DNA
<213> ORGANISM: Artificial Sequence
<220> FEATURE:
<223> OTHER INFORMATION: Synthetic

<400> SEQUENCE: 167
ctcgagtcag aacccgccga atccgtc                                     27

<210> SEQ ID NO 168
<211> LENGTH: 25
<212> TYPE: DNA
<213> ORGANISM: Artificial Sequence
<220> FEATURE:
<223> OTHER INFORMATION: Synthetic

<400> SEQUENCE: 168
gggttcatat gtcgtttgtc gtagc                                       25

<210> SEQ ID NO 169
<211> LENGTH: 25
<212> TYPE: DNA
<213> ORGANISM: Artificial Sequence
<220> FEATURE:
<223> OTHER INFORMATION: Synthetic

<400> SEQUENCE: 169
actggaacgg ctggaagctt gccgg                                       25

<210> SEQ ID NO 170
<211> LENGTH: 22
<212> TYPE: DNA
<213> ORGANISM: Artificial Sequence
<220> FEATURE:
<223> OTHER INFORMATION: Synthetic

<400> SEQUENCE: 170
```

```
atgtcgtttg tcgtagcagt cc                                              22
```

<210> SEQ ID NO 171
<211> LENGTH: 23
<212> TYPE: DNA
<213> ORGANISM: Artificial Sequence
<220> FEATURE:
<223> OTHER INFORMATION: Synthetic

<400> SEQUENCE: 171

```
gcactggaac ggctggtaat tag                                             23
```

<210> SEQ ID NO 172
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be Val or Thr
<220> FEATURE:
<221> NAME/KEY: misc_feature
<222> LOCATION: (3)..(3)
<223> OTHER INFORMATION: Xaa can be Ala or Pro
<220> FEATURE:
<221> NAME/KEY: misc_feature
<222> LOCATION: (10)..(10)
<223> OTHER INFORMATION: Xaa can be Thr or no amino acid

<400> SEQUENCE: 172

```
Thr Xaa Xaa Pro Thr Thr Val Ala Pro Xaa
1               5                   10
```

<210> SEQ ID NO 173
<211> LENGTH: 6
<212> TYPE: PRT
<213> ORGANISM: Artificial Sequence
<220> FEATURE:
<223> OTHER INFORMATION: Synthetic

<400> SEQUENCE: 173

```
Val Pro Arg Gly Ser Asp
1               5
```

<210> SEQ ID NO 174
<211> LENGTH: 6
<212> TYPE: PRT
<213> ORGANISM: Artificial Sequence
<220> FEATURE:
<223> OTHER INFORMATION: Synthetic

<400> SEQUENCE: 174

```
Asp Asp Lys Asp Trp His
1               5
```

<210> SEQ ID NO 175
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be Val or Thr
<220> FEATURE:
<221> NAME/KEY: misc_feature -continued

```
<222> LOCATION: (3)..(3)
<223> OTHER INFORMATION: Xaa can be Ala or Pro
<220> FEATURE:
<221> NAME/KEY: misc_feature
<222> LOCATION: (11)..(11)
<223> OTHER INFORMATION: Xaa can be Pro or Ser
<220> FEATURE:
<221> NAME/KEY: misc_feature
<222> LOCATION: (10)..(10)
<223> OTHER INFORMATION: Xaa can be Thr or no amino acid

<400> SEQUENCE: 175

Thr Xaa Xaa Pro Thr Thr Val Ala Pro Xaa
1               5                   10
```